(12) United States Patent
Lin et al.

(10) Patent No.: US 9,408,923 B2
(45) Date of Patent: *Aug. 9, 2016

(54) HYDROPHILIC SELF-IMMOLATIVE LINKERS AND CONJUGATES THEREOF

(71) Applicants: AbGenomics International Inc., Dover, DE (US); BioAlliance C.V., Alkmaar (NL)

(72) Inventors: Rong-Hwa Lin, Palo Alto, CA (US); Shih-Yao Lin, Taipei (TW); Yu-Chi Hsieh, New Taipei (TW); Chiu-Chen Huang, Taipei (TW)

(73) Assignees: BioAlliance C.V., Alkmaar (NL); AbGenomics International Inc., Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,621

(22) Filed: Jun. 17, 2015

(65) Prior Publication Data

US 2016/0015830 A1     Jan. 21, 2016

Related U.S. Application Data

(63) Continuation of application No. 14/137,799, filed on Dec. 20, 2013, now Pat. No. 9,089,614.

(60) Provisional application No. 61/785,027, filed on Mar. 14, 2013, provisional application No. 61/745,448, filed on Dec. 21, 2012.

(51) Int. Cl.
| | |
|---|---|
| *A61K 47/48* | (2006.01) |
| *C07D 241/36* | (2006.01) |
| *A61K 38/06* | (2006.01) |
| *A61K 31/404* | (2006.01) |
| *A61K 31/407* | (2006.01) |
| *C07D 295/192* | (2006.01) |
| *C07K 7/02* | (2006.01) |

(52) U.S. Cl.
CPC ......... *A61K 47/48715* (2013.01); *A61K 31/404* (2013.01); *A61K 31/407* (2013.01); *A61K 38/06* (2013.01); *A61K 47/48215* (2013.01); *A61K 47/48338* (2013.01); *A61K 47/48384* (2013.01); *A61K 47/48438* (2013.01); *A61K 47/48569* (2013.01); *A61K 47/48615* (2013.01); *C07D 241/36* (2013.01); *C07D 295/192* (2013.01); *C07K 7/02* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,750,373 A | 5/1998 | Garrard et al. |
| 5,985,908 A | 11/1999 | Boger |
| 6,060,608 A | 5/2000 | Boger |
| 6,214,345 B1 | 4/2001 | Firestone et al. |
| 6,262,271 B1 | 7/2001 | Boger |
| 6,281,354 B1 | 8/2001 | Boger |
| 6,486,326 B2 | 11/2002 | Boger |
| 6,548,530 B2 | 4/2003 | Boger |
| 7,091,186 B2 | 8/2006 | Senter et al. |
| 7,223,837 B2 | 5/2007 | De Groot et al. |
| 7,553,816 B2 | 6/2009 | Senter et al. |
| 7,674,605 B2 | 3/2010 | Lin et al. |
| 7,754,681 B2 | 7/2010 | Feng |
| 7,982,017 B2 | 7/2011 | Lin et al. |
| 8,153,581 B2 | 4/2012 | Kratz |
| 8,309,093 B2 | 11/2012 | Gudas et al. |
| 8,394,607 B2 | 3/2013 | Ebens, Jr. et al. |
| 8,568,718 B2 | 10/2013 | Lin et al. |
| 9,089,614 B2 | 7/2015 | Lin et al. |
| 2006/0024317 A1 | 2/2006 | Boyd et al. |
| 2010/0124551 A1 | 5/2010 | Lin et al. |
| 2011/0301334 A1 | 12/2011 | Bhakta et al. |
| 2012/0282175 A1 | 11/2012 | Carrigan et al. |
| 2013/0177579 A1 | 7/2013 | Lin et al. |

(Continued)

FOREIGN PATENT DOCUMENTS

| | | |
|---|---|---|
| EP | 2357006 A2 | 8/2011 |
| WO | WO-99/58572 A1 | 11/1999 |

(Continued)

OTHER PUBLICATIONS

Blencowe et al, Polym. Chem (2011) 2 p. 773-785.*
Al-Lazikani, B. et al. (Nov. 7, 1997). "Standard Conformations for the Canonical Structures of Immunoglobulins," Journal of Molecular Biology 273(4):927-948.
Bandgar, B.P. et al. (2003). "Highly Rapid and Direct Synthesis of Monoacylated Piperazine Derivatives from Carboxylic Acids Under Mild Conditions," Tetrahedron Letters 44: 3855-3858.
Blencowe, C.A. et al. (2011). "Self-Immolative Linkers in Polymeric Delivery Systems," Polym. Chem. 2:773-790.
Boerner, P. et al. (Jul. 1, 1991). "Production of Antigen-Specific Human Monoclonal Antibodies from in Vitro-primed Human Splenocytes," Journal of Immunology 147(1):86-95.

(Continued)

*Primary Examiner* — Maury Audet
*Assistant Examiner* — Fred Reynolds
(74) *Attorney, Agent, or Firm* — Morrison & Foerster LLP

(57) ABSTRACT

The present disclosure provides compounds with a hydrophilic self-immolative linker, which is cleavable under appropriate conditions and incorporates a hydrophilic group to provide better solubility of the compound. The compounds of the present disclosure comprise a drug moiety, a targeting moiety capable of targeting a selected cell population, and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker.

20 Claims, 7 Drawing Sheets

(56) References Cited

U.S. PATENT DOCUMENTS

| | | |
|---|---|---|
| 2014/0105899 A1 | 4/2014 | Lin et al. |
| 2015/0352222 A1 | 12/2015 | Lin et al. |
| 2016/0015827 A1 | 1/2016 | Lin et al. |
| 2016/0015831 A1 | 1/2016 | Lin et al. |

FOREIGN PATENT DOCUMENTS

| | | | |
|---|---|---|---|
| WO | WO-2006/034488 A2 | 3/2006 | |
| WO | WO-2006/034488 A3 | 3/2006 | |
| WO | WO-2007/103288 A2 | 9/2007 | |
| WO | WO-2007/140371 A2 | 12/2007 | |
| WO | WO-2007/146172 A2 | 12/2007 | |
| WO | WO-2007/146172 A3 | 12/2007 | |
| WO | WO-2007/146172 A8 | 12/2007 | |
| WO | WO-2008/038024 A1 | 4/2008 | |
| WO | WO-2008/070593 A2 | 6/2008 | |
| WO | WO-2008/070593 A3 | 6/2008 | |
| WO | WO-2008/083312 A2 | 7/2008 | |
| WO | WO-2008/083312 A3 | 7/2008 | |
| WO | WO-2009/079649 A1 | 6/2009 | |
| WO | WO-2009/092011 A1 | 7/2009 | |
| WO | WO-2009/099741 A1 | 8/2009 | |
| WO | WO-2010/141902 A2 | 12/2010 | |
| WO | WO-2010/141902 A3 | 12/2010 | |
| WO | WO-2011/005481 A1 | 1/2011 | |
| WO | WO-2011/156328 A1 | 12/2011 | |
| WO | WO-2013/093809 A1 | 6/2013 | |
| WO | WO-2013/103800 A1 | 7/2013 | |
| WO | WO-2013/181597 A2 | 12/2013 | |
| WO | WO-2013/181597 A3 | 12/2013 | |
| WO | WO-2014/009774 A1 | 1/2014 | |
| WO | WO-2014/012479 A1 | 1/2014 | |
| WO | WO-2014/057118 A1 | 4/2014 | |
| WO | WO-2014/100762 A1 | 6/2014 | |
| WO | WO-2015/196089 A1 | 12/2015 | |
| WO | WO-2015/196167 A1 | 12/2015 | |

OTHER PUBLICATIONS

Cabilly, S. et al. (1984). "Generation of Antibody Activity from Immunoglobulin Polypeptide Chains Produced in *Escherichia coli*," Proceedings of the National Academy of Sciences of the United States of America 81(11):3273-3277.

Carpino, L.A. (1993). "1-Hydroxy-7Azabenzotriazole. An Efficient Peptide Coupling Additive," J. Am. Chem. Soc. 115(10):4397-4398.

Carpino, L.A. et al. (1995). "Tetramethylfluoroformamidinium Hexafluorophosphate: A Rapid-Acting Peptide Coupling Reagent for Solution and Solid Phase Peptide Synthesis," J. Am. Chem. Soc. 117(19): 5401-5402.

Carter, P. J. et. al. (May/Jun. 2008). "Antibody-Drug Conjugates for Cancer Therapy," The Cancer Journal 14(3):154-169.

Chothia, C. et al. (Aug. 1987). "Canonical Structures for the Hypervariable Regions of Immunoglobulins," J. Mol. Biol. 196(4):901-917.

Cole, S.P.C. et al. (1985). "The EBV-Hybridoma Technique and its Application to Human Lung Cancer," Monoclonal Antibodies and Cancer Therapy, Reisfeld, R.A. et al. ed., Alan R. Liss Inc., New York, NY, 77-96.

Ducry L. et al. (2010). "Antibody-Drug Conjugates: Linking Cytotoxic Payloads to Monoclonal Antibodies," Bioconjugate Chem 21:5-13.

Farber, S. et al. (1948). "Temporary Remissions in Acute Leukemia in Children Produced by Folic Acid Antagonist, 4-Aminopteroyl-Glutamic Acid (Aminopterin", New England Journal of Medicine 238(23):787-793.

GenBank Accession No. ABI74084, located at <http://www.ncbi.nlm.nih.gov/protein/ABI74084>, last visited on Oct. 21, 2014, 2 pages.

Holt, L.J. et al. (Nov. 2003). "Domain Antibodies: Proteins for Therapy," Trends Biotechnology 21(11):484-490.

Hoogenboom, H.R. et al. (Sep. 1991). "By-Passing Immunisation: Human Antibodies from Synthetic Repertoires of Germline VH Gene Segments Rearranged in vitro," Journal of Molecular Biology 227(2):381-388.

International Search Report mailed on Apr. 4, 2014, for PCT Application No. PCT/US2013/077306, filed Dec. 20, 2013, 7 pages.

International Search Report, mailed on Oct. 13, 2015, for PCT Application No. PCT/US2015/036721, filed Jun. 19, 2015, 11 pages.

International Search Report, mailed on Oct. 14, 2015, for PCT Application No. PCT/US2015/036824, filed Jun. 19, 2015, 5 pages.

Jeffrey S. C. et. al. (2005). "Design, Synthesis, and in Vitro Evaluation of Dipeptide-Based Antibody Minor Groove Binder Conjugates," J. Med. Chem. 48(5):1344-1358.

Jeffrey, S.C. et al. (Jul. 17, 2013, e-published Jun. 28, 2013). "A Potent Anti-CD70 Antibody-Drug Conjugate Combining a Dimeric Pyrrolobenzodiazepine Drug with Site-Specific Conjugation Technology," Bioconjug. Chem. 24(7):1256-1263.

Junutula, J.R. et al. (Aug. 2008, e-published Jul. 20, 2008). "Site-Specific Conjugation of a Cytotoxic Drug to an Antibody Improves the Therapeutic Index," Nat. Biotech. 26(8):925-932.

Kitson, S. et. al. "Antibody-drug conjugates (ADCs)—Biotherapeutic bullets", Monographic Supplement Series CROs/CMOs—Chimica Oggi—Chemistry Today, 2013, 31(4), 30-36p. 33, Table, Inotuzumab ozogamicin and RG7593/DCDT2980S.

Koblinski, J.E. et al. (Feb. 15, 2000). "Unraveling the Role of Proteases in Cancer," Clin. Chem. Acta 291(2):113-135.

Kohler, G. et al. (Aug. 7, 1975). "Continuous Cultures of Fused Cells Secreting Antibody of Predefined Specificity," Nature 256(5517):495-497.

Li, P. et al. (Aug. 2001). "The Development of Highly Efficient Onium-Type Peptide Coupling Reagents Based Upon Rational Molecular Design," J. Pept. Res. 58(2):129-139.

Li, D. et al. "DCDT2980S, an anti-CD22-monomethyl Auristatin E antibody-drug conjugate, is a potential treatment for non-Hodgkin lymphoma", Molecular Cancer Therapeutics, 2013, 12(7), 1255-1265p. 1259, Figure 1, A, Abstract.

Loudon, G.M. (2002). Organic Chemistry, Fourth Edition, Oxford University Press, New York, pp. 360-361, 1084-1085.

Lyons, A. et al. (Aug. 1990). "Site-Specific Attachment to Recombinant Antibodies via Introduced Surface Cysteine Residues," Protein Engineering 3(8):703-708.

McCafferty, J. et al. (Dec. 6, 1990). "Phage Antibodies: Filamentous Phage Displaying Antibody Variable Domains," Nature 348(6301):552-554.

Marks, J. D. et al. (Dec. 5, 1991). "By-Passing Immunization: Human Antibodies From V-Gene Libraries Displayed on Phage," Journal of Molecular Biology 222(3):581-597.

Muyldermans, S. et al. (Jun. 2001). "Single Domain Camel Antibodies: Current Status," Journal of Biotechnology 74(4):277-302.

Polson, A. G. et. al. "Antibody-drug conjugates for the treatment of non-Hodgkin's lymphoma: Target and linker-drug selection", Cancer Research, 2009, 69(6), 2358-2364.

Sheets, M.D. et al. (May 26, 1998). "Efficient Construction of a Large Nonimmune Phage Antibody Library: The Production of High-Affinity Human Single-Chain Antibodies to Protein Antigens," Proceedings of the National Academy of Sciences of the United States of America 95(11): 6157-6162.

Stimmel, J.B. et al. (Sep. 29, 2000, e-published Jul. 3, 2000). "Site-Specific Conjugation on Serine ☐ Cysteine Variant Monoclonal Antibodies," J. Biol. Chem. 275(39):30445-30450.

Sun, M.M.C. et al. (Sep./Oct. 2005). "Reduction-Alkylation Strategies for the Modification of Specific Monoclonal Antibody Disulfides," Bioconjug. Chem. 16(5):1282-1290.

Teicher, B.A. et al. (Dec. 2009). "Antibody-Drug Conjugate Targets," Current Cancer Drug Targets 9(8): 982-1004.

Trail, P. A. et al. (Jul. 9, 1993). "Cure of Xenografted Human Carcinomas by BR96-Doxorubicin Immunoconjugates," Science 261(5118):212-215.

Trail, P. A. et al. (Jan. 1, 1997). "Effect of Linker Variation on the Stability, Potency, and Efficacy of Carcinoma-Reactive BR64-Doxorubicin Immunoconjugates," Cancer Research 57(1):100-105.

(56) References Cited

OTHER PUBLICATIONS

Vaughan, T.J. et al. (Mar. 1996). "Human Antibodies with Sub-Nanomolar Affinities Isolated from a Large Non-Immunized Phage Display Library," Nature Biotechnology 14(3):309-314.
Vlahov, I.R. et al., "Engineering folate-drug conjugates to target cancer: From chemistry to clinic". Bioconjugate Chemistry, 2012, 23, 1357-1369.
Written Opinion mailed on Apr. 4, 2014, for PCT Application No. PCT/US2013/077306, filed Dec. 20, 2013, 10 pages.
Written Opinion mailed on Oct. 13, 2015, for PCT Application No. PCT/US2015/036721, filed Jun. 19, 2015, 9 pages.
Written Opinion mailed on Oct. 14, 2015, for PCT Application No. PCT/US2015/036824, filed on Jun. 20, 2014, 8 pages.
Yu Shang-Fan et. al. "A novel anti-CD22 anthracycline-based antibody-drug conjugate (ADC) that overcomes resistance to Auristatin-based ADC's", Clinical Cancer Research, 2015, 21(14), 3298-3306 [Published online, Apr. 3, 2015] The whole document, particularly Abstract, Figures 1, 5.
GenBank Accession No. CAA79298, located at <http:ncbi.nlm.nih.gov/protein/CAA79298>, last visited on Oct. 21, 2014, 2 pages.
U.S. Appl. No. 14/654,486, filed Jun. 19, 2015, by Lin et al.

* cited by examiner

SEQUENCE LISTING

<160> NUMBER OF SEQ ID NOS: 4

<210> SEQ ID NO 1
<211> LENGTH: 448
<212> TYPE: PRT
<213> ORGANISM: Artificial Sequence
<220> FEATURE:
<223> OTHER INFORMATION: Synthetic construct

<400> SEQUENCE: 1

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Ile Arg Gln Ala Pro Gly Gln Gly Leu Glu Trp Ile
        35                  40                  45

Gly Tyr Ile Asn Pro Tyr Asn Gly Gly Thr Gln Tyr Asn Glu Lys Phe
    50                  55                  60

Lys Gly Arg Ala Thr Leu Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Thr Phe Pro Tyr Tyr Phe Asp Tyr Trp Gly Gln Gly Thr
            100                 105                 110

Leu Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
```

```
                355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445

<210> SEQ ID NO 2
<211> LENGTH: 219
<212> TYPE: PRT
<213> ORGANISM: Artificial Sequence
<220> FEATURE:
<223> OTHER INFORMATION: Synthetic construct

<400> SEQUENCE: 2

Asp Val Val Met Thr Gln Thr Pro Leu Ser Leu Pro Val Thr Leu Gly
1               5                   10                  15
Glu Pro Ala Ser Ile Ser Cys Arg Ser Ser Gln Ser Ile Leu His Ser
            20                  25                  30
Asn Gly Asn Thr Tyr Leu Glu Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Ala Pro Leu Thr Phe Gly Gly Gly Thr Lys Leu Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215

<210> SEQ ID NO 3
<211> LENGTH: 449
<212> TYPE: PRT
<213> ORGANISM: Artificial Sequence
<220> FEATURE:
<223> OTHER INFORMATION: Synthetic construct

<400> SEQUENCE: 3
```

-continued

```
Glu Val Gln Leu Gln Gln Ser Gly Pro Glu Val Val Lys Pro Gly Ala
  1               5                  10                  15
Ser Met Lys Met Ser Cys Lys Thr Ser Gly Tyr Lys Phe Thr Gly Tyr
             20                  25                  30
Tyr Met Asp Trp Val Lys Gln Ser Leu Gly Ala Ser Phe Glu Trp Ile
         35                  40                  45
Gly Arg Val Ile Pro Ser Asn Gly Asp Thr Arg Tyr Asn Gln Lys Phe
     50                  55                  60
Glu Gly Lys Ala Thr Leu Thr Val Asp Arg Ser Ser Thr Ala Tyr
 65                  70                  75                  80
Met Glu Leu Asn Ser Leu Thr Ser Glu Asp Ser Ala Val Tyr Tyr Cys
                 85                  90                  95
Ala Arg Lys Pro Leu Ser Gly Asn Ala Ala Asp Tyr Trp Gly Gln Gly
            100                 105                 110
Thr Ser Val Thr Val Ser Thr Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
```

```
                         420                 425                 430
Ala Leu His Asn His Tyr Thr Gln Lys Ser Leu Ser Leu Ser Pro Gly
        435                 440                 445

Lys

<210> SEQ ID NO 4
<211> LENGTH: 214
<212> TYPE: PRT
<213> ORGANISM: Artificial Sequence
<220> FEATURE:
<223> OTHER INFORMATION: Synthetic construct

<400> SEQUENCE: 4

Glu Thr Thr Val Thr Gln Ser Pro Ala Ser Leu Ser Val Ala Thr Gly
 1               5                  10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Asp Gly Asn Thr Leu Arg Pro Gly Val Pro Ser Arg Phe Ser Ser
 50                  55                  60

Ser Gly Tyr Gly Thr Asp Phe Val Phe Thr Ile Glu Asn Thr Leu Ser
65                  70                  75                  80

Glu Asp Ile Thr Asp Tyr Tyr Cys Met Gln Ser Asp Asn Met Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

HYDROPHILIC SELF-IMMOLATIVE LINKERS AND CONJUGATES THEREOF

CROSS-REFERENCE TO RELATED APPLICATIONS

This application is a continuation of U.S. patent application Ser. No. 14/137,799, filed on Dec. 20, 2013, which claims the priority benefit of U.S. Provisional Patent Application No. 61/745,448, filed Dec. 21, 2012 and U.S. Provisional Patent Application No. 61/785,027, filed Mar. 14, 2013, the disclosures of which are incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 606592000801SeqList.txt, date recorded: Sep. 29, 2015, size: 12 KB).

FIELD OF INVENTION

The invention is in the field of pharmaceuticals, and provides drug conjugates for the delivery of drugs to cell populations, where the prodrugs are metabolized and activated by endogenous enzymes to provide active drugs.

BACKGROUND

Antibody-drug conjugates (ADCs) are a class of therapeutics that combines the specificity of monoclonal antibodies (mAbs) with the potency of cytotoxic molecules. ADCs take advantage of characteristics of both components and significantly expand the therapeutic index of cytotoxic molecules by minimizing systemic exposure and associated toxicity while at the same time maximizing delivery of the cytotoxic agents to the target lesion, thus increasing treatment efficacy. Brentuximab Vedotin (SGN-35), an anti-CD30 antibody conjugated with cytotoxic agent MMAE, is already approved to treat CD30-positive relapsing lymphoma.

Target antigen selection, internalization of ADCs by tumor cells, and potency of cytotoxic drugs are parameters for ADC development (Carter 2008, Teicher 2009). In additional, the design of chemical linkers to covalently bind these building blocks to form an ADC also plays a role in the development of the ADCs (Ducry 2010). For example, the linker should be stable in the bloodstream to limit the damage to healthy tissue. Decomposition or decay of ADCs can release the cytotoxic drug before its delivery to the target sites. However, once the ADCs reach the target sites, they have to release the cytotoxic drug efficiently in its active form. The balance between plasma stability and efficient drug release at the target cell has yet to be found, which can depend on the linker design.

At least three types of linkers are applied in ADC design, namely, chemically-labile linkers, enzyme-labile linkers, and non-cleavable linkers (Ducry 2010). For chemically labile linkers, such as hydrazone linker for Mylotarg and disulfide-bearing 4-mercaptopentanoate linker for DM1/DM4, selective cleavage of the linker and payload release for ADC is based upon the differential properties of the linker between the plasma and some cytoplasmic compartment. Linkers are relative stable in the blood's neutral pH environment but can get cleaved once the ADC enters the lower pH environment inside the cell. An in vivo trial demonstrated that chemically-labile linkers often suffer from limited plasma stability.

Enzyme-labile linkers take an alternative approach—the differential activities of proteases inside and outside of the cells—to achieve control of the drug release. Proteases normally are not active outside cells due to the unfavorable pH conditions and the presence of serum protease inhibitors. A drug can be conjugated to antibody via peptide bond. The drug can be specifically cleaved from the antibody by the action of lysosomal proteases present inside the cells, and at elevated levels in certain tumor types (Koblinsk et al). Compared to ADC with chemically-labile linker, enzyme-labile linkers can achieve better control of the drug release. However, the increased associated hydrophobicity of some enzyme-labile linkers can lead to aggregation of ADC, particularly with strongly hydrophobic drugs.

A third class of linkers is non-cleavable linkers. The release of the drug is believed to occur via the internalization of the ADC followed by the degradation of the antibody component in the lysosome, resulting in the release of the drug which is still attached to the linker. These non-cleavable linkers are stable in serum, but compared to enzyme-labile linkers, no bystander effect can result due to the fact that the released drugs are charged and are not able to diffuse into neighboring cells. Also, since internalization of the ADC is a factor for the release of the drug, the efficacy is antigen- (and thus antibody-) dependent.

Linker technology affects ADC potency, specificity, and safety. There is a need for linkers for ADCs which can provide serum stability as well as increased solubility, allowing efficient conjugation and intracellular delivery of hydrophobic drugs.

SUMMARY

The compounds of the present disclosure comprise a drug moiety, a targeting moiety capable of targeting a selected cell population, and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker.

The present disclosure provides a compound of Formula (I):

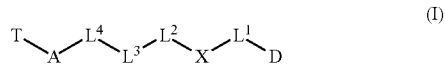

or a salt or solvate or stereoisomer thereof;
wherein:
D is drug moiety;
T is a targeting moiety;
X is a hydrophilic self-immolative linker;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is bond or a spacer; and
A is an acyl unit.

The present disclosure also provides a compound of Formula (II):

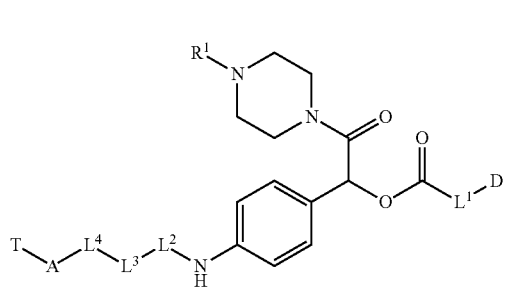

(II)

or a salt or solvate or stereoisomer thereof;

wherein:
D is drug moiety;
T is a targeting moiety;
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond, a second self-immolative linker;
 wherein if $L^1$ is a second self-immolative linker or a cyclization self-elimination linker, then $L^2$ is a bond;
 wherein if $L^2$ is a second self-immolative linker, then $L^1$ is a bond;
$L^3$ is a peptide linker;
$L^4$ is bond or a spacer; and
A is an acyl unit.

The present disclosure also provides a compound of Formula (III):

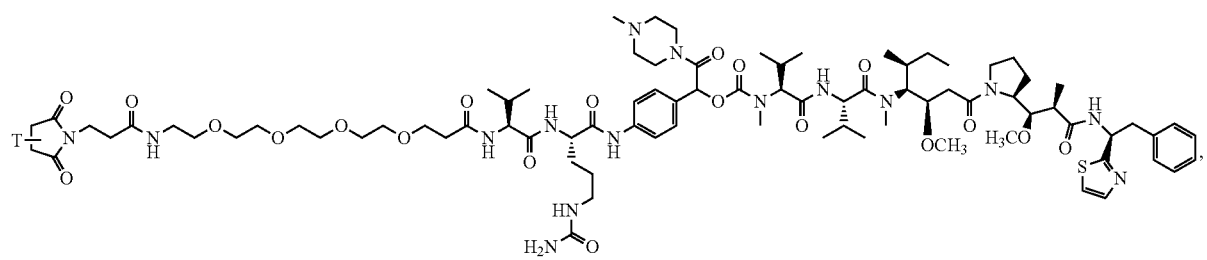

(III)

or a salt or solvate or stereoisomer thereof;
wherein T is a targeting moiety.

The present disclosure provides a compound of Formula (IV):

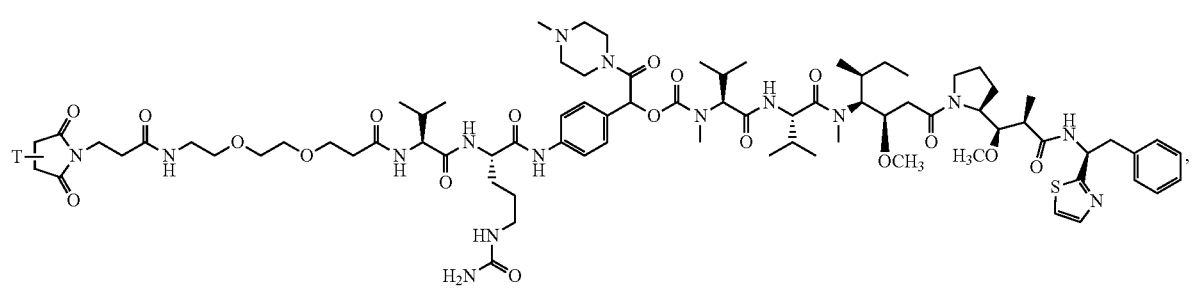

(IV)

or a salt or solvate or stereoisomer thereof;
wherein T is a targeting moiety.

The present disclosure provides a compound of Formula (V):

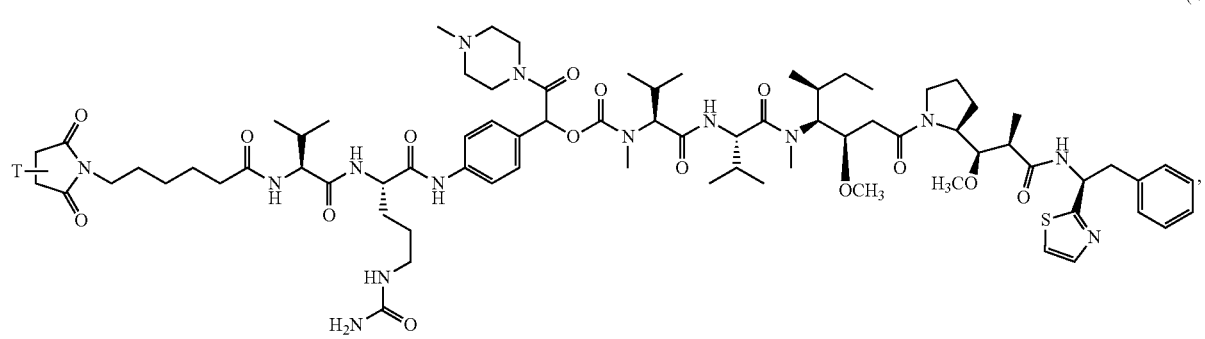

(V)

or a salt or solvate or stereoisomer thereof;
wherein T is a targeting moiety.

The present disclosure provides a compound of Formula (VI):

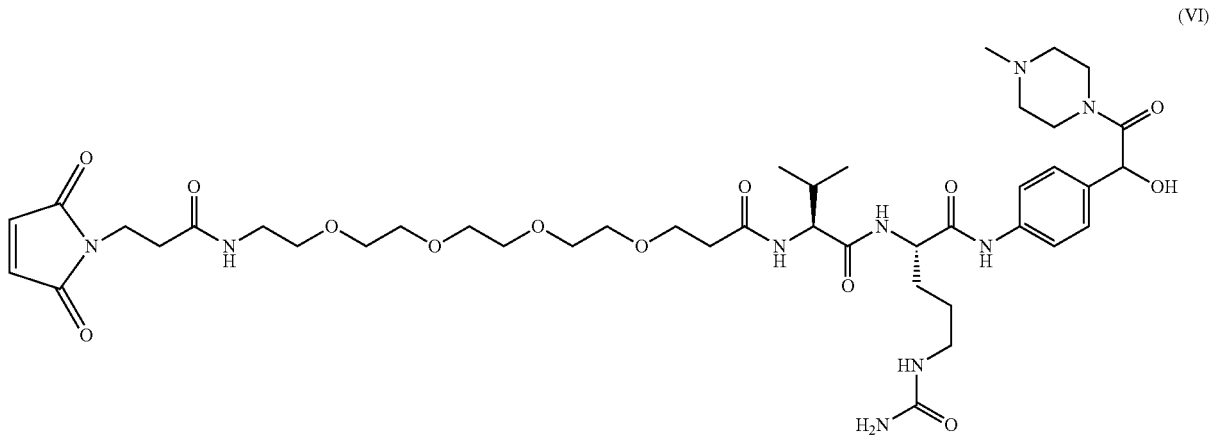 [SMILES: CC(C)[C@H](NC(=O)CCOCCOCCOCCOCCNC(=O)CCN1C(=O)C=CC1=O)C(=O)N[C@@H](CCCNC(N)=O)C(=O)Nc1ccc(C(O)C(=O)N2CCN(C)CC2)cc1]

(VI)

or a salt or solvate thereof.

The present disclosure provides a compound of Formula (VII):

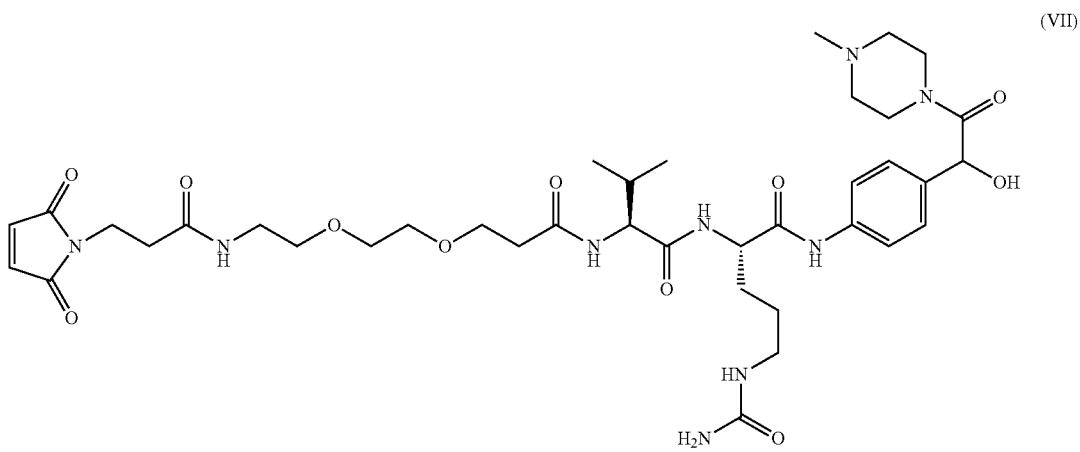 [SMILES: CC(C)[C@H](NC(=O)CCOCCOCCNC(=O)CCN1C(=O)C=CC1=O)C(=O)N[C@@H](CCCNC(N)=O)C(=O)Nc1ccc(C(O)C(=O)N2CCN(C)CC2)cc1]

(VII)

or a salt or solvate thereof.

The present disclosure provides a compound of Formula (VIII):

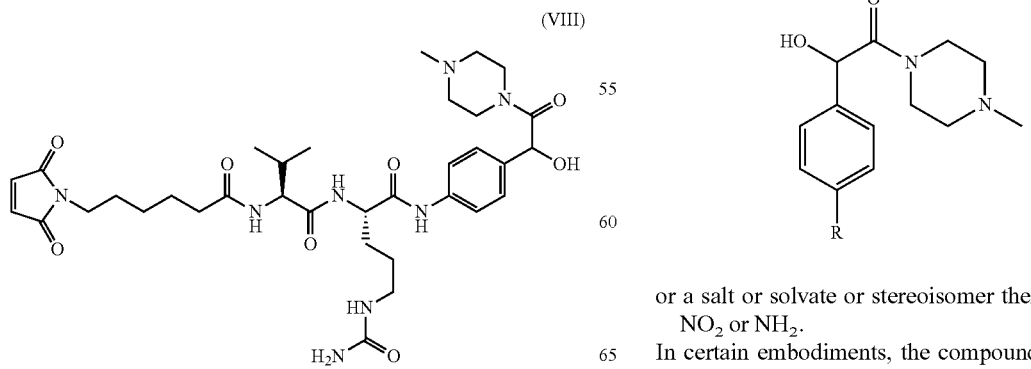

(VIII)

The present disclosure provides a compound of Formula (XII):

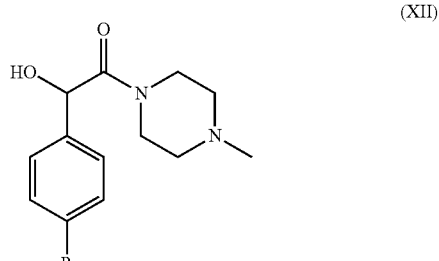

(XII)

or a salt or solvate or stereoisomer thereof; wherein R is $NO_2$ or $NH_2$.

In certain embodiments, the compound of Formulae (I)-(XII) is a compound selected from those species described or exemplified in the detailed description herein.

In a further aspect, the present disclosure provides a pharmaceutical composition comprising at least one compound of Formulae (I)-(V) or a pharmaceutically acceptable salt thereof. Pharmaceutical compositions according to the embodiments may further comprise a pharmaceutically acceptable excipient. The present disclosure also provides a compound of Formulae (I)-(V) or a pharmaceutically acceptable salt thereof for use as a medicament.

In another aspect, the present disclosure provides a method of killing a cell, comprising administering to the cell an amount of the compound of Formulae (I)-(V) sufficient to kill the cell.

In another aspect, the present disclosure provides a method of treating cancer in an individual in need thereof comprising administering to the individual an effective amount of a compound of Formulae (I)-(V).

Additional embodiments, features, and advantages of the invention will be apparent from the following detailed description and through practice of the invention.

DEFINITIONS

Figure 1:
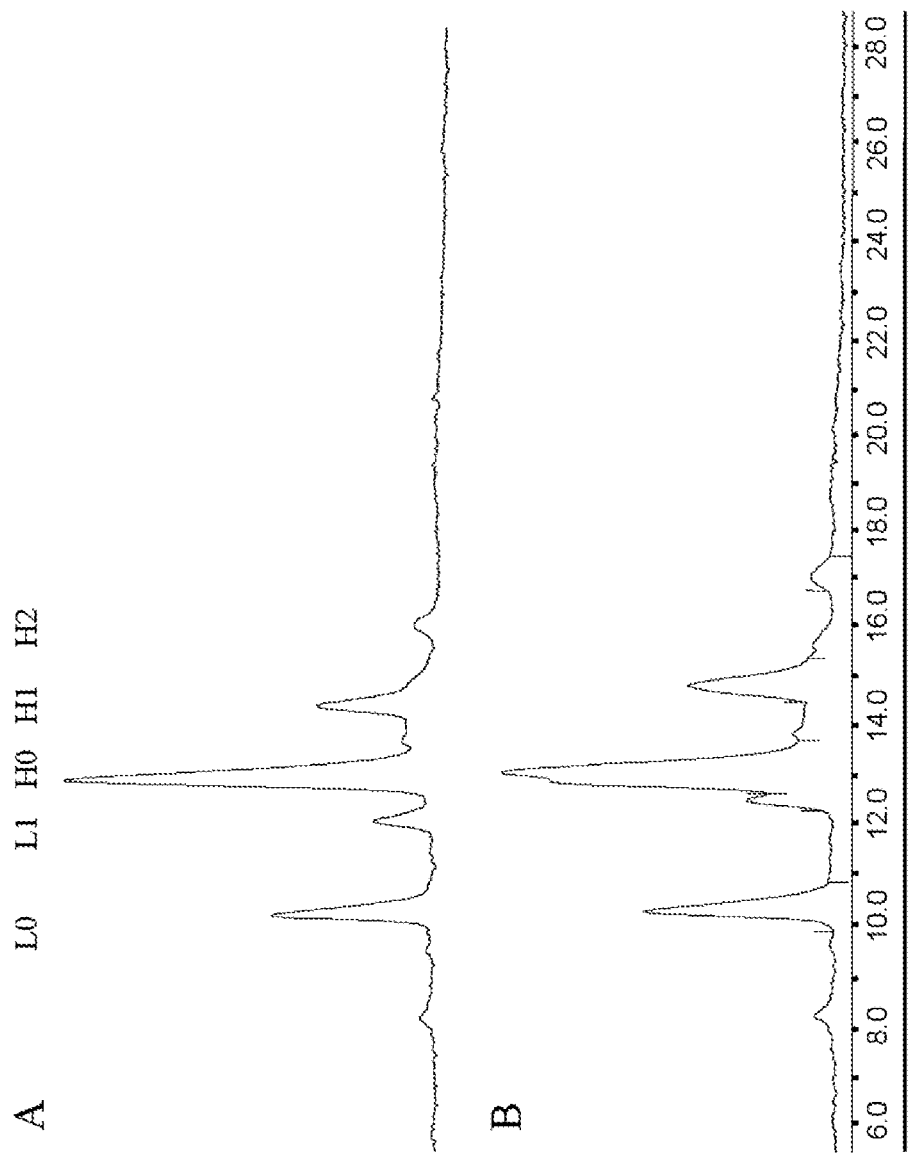
FIG. 1 shows reversed-phase HPLC characterization of certain ADCs of the present embodiments.

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), neopentyl (($CH_3)_3CCH_2$—), and n-hexyl ($CH_3(CH_2)_5$—).

"Alkylene" refers to divalent aliphatic hydrocarbylene groups preferably having from 1 to 10 and more preferably 1 to 3 carbon atoms that are either straight-chained or branched. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like.

"Alkenyl" refers to straight chain or branched hydrocarbyl groups having from 2 to 10 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

"Alkenylene" refers to straight chain or branched hydrocarbylene groups having from 2 to 10 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

"Alkynyl" refers to straight or branched hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2$C≡CH).

"Alkynylene" refers to straight or branched hydrocarbylene groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—$CH_2$C≡CH).

"Amino" refers to the group —$NH_2$.

"Substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aryl" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO— heteroaryl, —SO$_2$-alkyl, —SO$_2$-substituted alkyl, —SO$_2$-aryl and —SO$_2$-heteroaryl, and trihalomethyl.

Examples of heteroaryls include, but are not limited to, pyrrole, imidazole, pyrazole, pyridine, pyrazine, pyrimidine, pyridazine, indolizine, isoindole, indole, purine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, piperidine, piperazine, phthalimide, 4,5,6,7-tetrahydrobenzo[b]thiophene, thiazole, thiophene, benzo[b]thiophene, and the like.

"Heterocycle," "heterocyclic," "heterocycloalkyl" or "heterocyclyl" refers to a saturated or partially unsaturated group having a single ring or multiple condensed rings, including fused, bridged, or spiro ring systems, and having from 3 to 20 ring atoms, including 1 to 10 hetero atoms. These ring atoms are selected from the group consisting of carbon, nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for N-oxide, —S(O)—, or —SO$_2$— moieties.

Examples of heterocycles include, but are not limited to, azetidine, dihydroindole, indazole, quinolizine, imidazolidine, imidazoline, piperidine, piperazine, indoline, 1,2,3,4-tetrahydroisoquinoline, thiazolidine, morpholinyl, thiomorpholinyl (also referred to as thiamorpholinyl), 1,1-dioxothiomorpholinyl, piperidinyl, pyrrolidine, tetrahydrofuranyl, and the like.

Where a heteroaryl or heterocyclyl group is "substituted," unless otherwise constrained by the definition for the heteroaryl or heterocyclic substituent, such heteroaryl or heterocyclic groups can be substituted with 1 to 5, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, azido, cyano, halogen, hydroxyl, oxo, thioketo, carboxyl, carboxyl ester, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, sulfonylamino, —SO-alkyl, —SO-substituted alkyl, —SO-aryl, —SO-heteroaryl, —SO— heterocyclyl, —SO$_2$-alkyl, —SO$_2$-substituted alkyl, —SO$_2$-aryl, —SO$_2$-heteroaryl, and —SO$_2$-heterocyclyl.

"Polyalkylene glycol" refers to straight or branched polyalkylene glycol polymers such as polyethylene glycol, polypropylene glycol, and polybutylene glycol. A polyalkylene glycol subunit is a single polyalkylene glycol unit. For example, an example of a polyethylene glycol subunit would be an ethylene glycol, —O—CH$_2$—CH$_2$—O—, or propylene glycol, —O—CH$_2$—CH$_2$—CH$_2$—O—, capped with a hydrogen at the chain termination point. Other examples of poly(alkylene glycol) include, but are not limited to, PEG, PEG derivatives such as methoxypoly(ethylene glycol) (mPEG), poly(ethylene oxide), PPG, poly(tetramethylene glycol), poly(ethylene oxide-co-propylene oxide), or copolymers and combinations thereof.

"Polyamine" refers to polymers having an amine functionality in the monomer unit, either incorporated into the backbone, as in polyalkyleneimines, or in a pendant group as in polyvinyl amines.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —S(O)R$^{70}$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O—OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$ M$^+$, —NR$^{70}$CO$_2$R$^{70}$, —NR$^{70}$C(S)OR$^{70}$, —NR$^{70}$C(O)NR$^{80}$R$^{80}$, —NR and —NR$^{70}$C(NR$^{70}$)NR$^{80}$R$^{80}$, where R$^{60}$ is selected from the group consisting of optionally substituted alkyl, cycloalkyl, heterocycloalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 3-, 4-, 5-, 6-, or 7-membered heterocycloalkyl which may optionally include from 1 to 4 of the same or different additional heteroatoms selected from the group consisting of O, N and S, of which N may have —H, C$_1$-C$_4$ alkyl, —C(O)C$_{1-4}$alkyl, —CO$_2$C$_{1-4}$ alkyl, or —SO$_2$C$_{1-4}$alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{+2}$]$_{0.5}$, or [Ba$^{2+}$]$_{0.5}$ ("subscript 0.5 means that one of the counter ions for such divalent alkali earth ions can be an ionized form of a compound of the embodiments and the other a typical counter ion such as chloride, or two ionized compounds disclosed herein can serve as counter ions for such divalent alkali earth ions, or a doubly ionized compound of the embodiments can serve as the counter ion for such divalent alkali earth ions).

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —S(O)R$^{70}$, —SO$_2$R$^{70}$, —SO$_3$$^-$ M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the substituent groups disclosed with respect to the individual terms herein, substituent groups for hydrogens on nitrogen atoms in "substituted" heterocycloalkyl and cycloalkyl groups are, unless otherwise specified, —R$^{60}$, —O$^-$M$^+$, —OR$^{70}$, —SR$^{70}$, —S$^-$M$^+$, —NR$^{80}$R$^{80}$ trihalomethyl, —CF$_3$, —CN, —NO, —NO$_2$, —S(O)R$^{70}$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

As used herein, an "effective dosage" or "effective amount" of drug, compound, conjugate, drug conjugate, antibody drug conjugate, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of the present disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

As used herein, "treatment" or "treating" is an approach for obtaining beneficial or desired results including and preferably clinical results. For purposes of the present disclosure, beneficial or desired clinical results include, but are not limited to, one or more of the following: reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "individual" or a "subject" is a mammal, more preferably a human. Mammals also include, but are not limited to, farm animals, sport animals, pets (such as cats, dogs, horses), primates, mice and rats.

As used herein, the term "specifically recognizes" or "specifically binds" refers to measurable and reproducible interactions such as attraction or binding between a target and an antibody (or a molecule or a moiety), that is determinative of the presence of the target in the presence of a heterogeneous population of molecules including biological molecules. For example, an antibody that specifically or preferentially binds to an epitope is an antibody that binds this epitope with greater affinity, avidity, more readily, and/or with greater duration than it binds to other epitopes of the target or non-target epitopes. It is also understood that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, the terms "cancer," "tumor," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, and sarcoma. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, prostate cancer, thyroid cancer, testicular cancer, esophageal cancer, gallbladder cancer, and various types of head and neck cancer.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, $4^{th}$ edition, New York: Oxford University Press, 2002, pp. 360-361, 1084-1085; Smith and March, March's Advanced Organic Chemistry: Reactions, Mechanisms, and Structure, $5^{th}$ edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by

DETAILED DESCRIPTION

The present disclosure provides compounds with a hydrophilic self-immolative linker, which may be cleavable under appropriate conditions and incorporates a hydrophilic group to provide better solubility of the compound. The hydrophilic self immolative linker may provide increased solubility of drug conjugates for cytotoxic drugs which are often hydrophobic. Other advantages of using a hydrophilic self-immolative linker in a drug conjugate include increased stability of the drug conjugate and decreased aggregation of the drug conjugate.

The present disclosure provides drug conjugates may have superior serum stability. For example, in contrast to drug conjugates wherein a hydroxyl group of a drug is linked to a spacer via a labile carbonate linkage that is susceptible to rapid hydrolysis in aqueous buffer or human serum, the drug conjugates of the present embodiments utilizing a benzyloxycarbonyl linkage may be relatively more stable under the same conditions, and may selectively undergo fragmentation to release the drug upon treatment with protease, e.g., cathepsin B. Serum stability is a desirable property for drug conjugates where it is desired to administer inactive drug to the patient's serum, have that inactive drug concentrate at a target by way of the ligand, and then have that drug conjugate converted to an active form only in the vicinity of the target.

The present disclosure provides drug conjugates which may have decreased aggregation. Increased associated hydrophobicity of some enzyme-labile linkers may lead to aggregation of drug conjugates, particularly with strongly hydrophobic drugs. With incorporation of a hydrophilic group into the linker, there may be decreased aggregation of the drug conjugate.

The compounds of the present disclosure comprise a drug moiety, a targeting moiety capable of targeting a selected cell population, and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker. Each of the features is discussed below.

The present disclosure provides a compound of Formula (I):

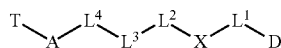

(I)

or a salt or solvate or stereoisomer thereof;
wherein:
D is drug moiety;
T is a targeting moiety;
X is a hydrophilic self-immolative linker;
$L^1$ is a bond, a second self-immolative linker, or a cyclization self-elimination linker;
$L^2$ is a bond or a second self-immolative linker;
 wherein if $L^1$ is a second self-immolative linker or a cyclization self-elimination linker, then $L^2$ is a bond;
 wherein if $L^2$ is a second self-immolative linker, then $L^1$ is a bond;
$L^3$ is a peptide linker;
$L^4$ is bond or a spacer; and
A is an acyl unit.

Peptide Linker

In Formula (I), $L^3$ is a peptide linker. In certain embodiments, $L^3$ is a peptide linker of 1 to 10 amino acid residues. In certain embodiments, $L^3$ is a peptide linker of 2 to 4 amino acid residues. In certain instances, $L^3$ is a dipeptide linker.

An amino acid residue can be a naturally-occurring or non-natural amino acid residue. The terms "natural amino acid" and "naturally-occurring amino acid" refer to Ala, Asp, Cys, Glu, Phe, Gly, His, Ile, Lys, Leu, Met, Asn, Pro, Gln, Arg, Ser, Thr, Val, Trp, and Tyr. "Non-natural amino acids" (i.e., amino acids do not occur naturally) include, by way of non-limiting example, homoserine, homoarginine, citrulline, phenylglycine, taurine, iodotyrosine, seleno-cysteine, norleucine ("Nle"), norvaline ("Nva"), beta-alanine, L- or D-naphthalanine, ornithine ("Orn"), and the like.

Amino acids also include the D-forms of natural and non-natural amino acids. "D-" designates an amino acid having the "D" (dextrorotary) configuration, as opposed to the configuration in the naturally occurring ("L-") amino acids. Where no specific configuration is indicated, one skilled in the art would understand the amino acid to be an L-amino acid. The amino acids can, however, also be in racemic mixtures of the D- and L-configuration. Natural and non-natural amino acids can be purchased commercially (Sigma Chemical Co.; Advanced Chemtech) or synthesized using methods known in the art. Amino acid substitutions may be made on the basis of similarity in polarity, charge, solubility, hydrophobicity, hydrophilicity, and/or the amphipathic nature of the residues as long as their biological activity is retained.

The amino acid residue sequence can be specifically tailored so that it will be selectively enzymatically cleaved from the resulting peptidyl derivative drug-conjugate by one or more of the tumor-associated proteases.

In certain embodiments, $L^3$ is a peptide linker comprising at least one lysine or arginine residue.

In certain embodiments, $L^3$ is a peptide linker comprising an amino acid residue selected from lysine, D-lysine, citrulline, arginine, proline, histidine, ornithine and glutamine.

In certain embodiments, $L^3$ is a peptide linker comprising an amino acid residue selected from valine, isoleucine, phenylalanine, methionine, asparagine, proline, alanine, leucine, tryptophan, and tyrosine.

In certain embodiments, $L^3$ is a dipeptide linker selected from valine-citrulline, proline-lysine, methionine-D-lysine, asparagine-D-lysine, isoleucine-proline, phenylalanine-lysine, and valine-lysine. In certain embodiments, $L^3$ is valine-citrulline.

Numerous specific peptide linker molecules suitable for use in the present disclosure can be designed and optimized in their selectivity for enzymatic cleavage by a particular tumor-associated protease. Certain peptide linkers for use in the present disclosure are those which are optimized toward the proteases, cathepsin B and D.

Hydrophilic Self-Immolative Linker

In Formula (I), X is a hydrophilic self-immolative linker.

The compound of the present disclosure employs a hydrophilic self-immolative spacer moiety which spaces and covalently links together the drug moiety and the targeting moiety and incorporates a hydrophilic group, which provides better solubility of the compound. Increased associated hydrophobicity of some enzyme-labile linkers can lead to aggregation of drug conjugates, particularly with strongly hydrophobic drugs. With incorporation of a hydrophilic group into the linker, there may be a decreased aggregation of the drug conjugate.

A self-immolative spacer may be defined as a bifunctional chemical moiety which is capable of covalently linking together two spaced chemical moieties into a normally stable tripartite molecule, can release one of the spaced chemical moieties from the tripartite molecule by means of enzymatic cleavage; and following enzymatic cleavage, can spontaneously cleave from the remainder of the molecule to release the other of the spaced chemical moieties.

In certain embodiments, X is a benzyloxycarbonyl group. In certain embodiments, X is

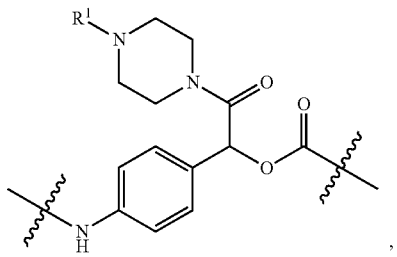

, wherein $R^1$ is hydrogen, unsubstituted or substituted $C_{1-3}$ alkyl, or unsubstituted or substituted heterocyclyl.

In such instance, the present disclosure provides a compound of Formula (II):

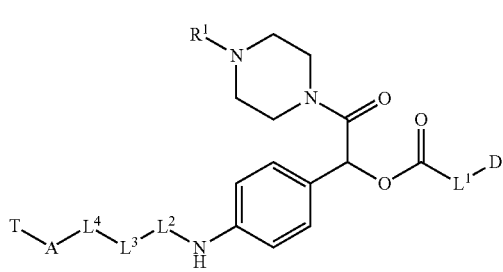

(II)

or a salt or solvate or stereoisomer thereof;
wherein:
D is drug moiety;
T is a targeting moiety;
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond, a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is bond or a spacer; and
A is an acyl unit.

In certain embodiments of Formula (II), $R^1$ is hydrogen. In certain instances, $R^1$ is methyl.

The release of the drug moiety is based on the self-elimination reaction of aminobenzyloxycarbonyl group. For illustration purposes, a reaction scheme with an aminobenzyloxycarbonyl group with a drug and peptide attached is shown below.

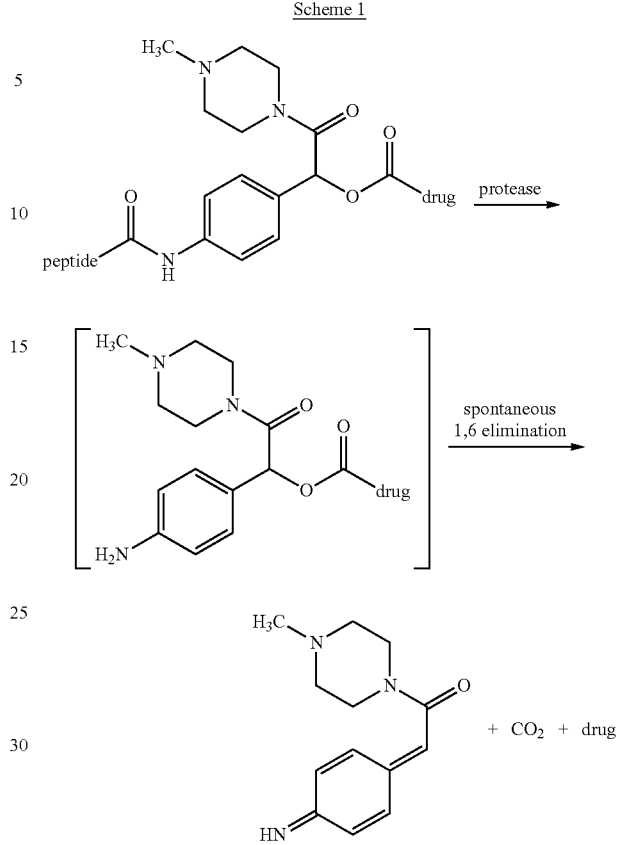

Referring to Scheme 1, upon cleavage from a peptide, an aminobenzyloxycarbonyl is formed and is able to undergo a spontaneous 1,6 elimination to form a cyclohexa-2,5-dien-imine derivative and carbon dioxide and release the drug.

Optional Second Self-Immolative Linker or Cyclization Self-Elimination Linker

A second self-immolative linker or cyclization self-elimination linker provides an additional linker for allowance of fine-tuning the cleavage of the compound to release the drug moiety.

In Formula (I), $L^1$ is a bond, a second self-immolative linker, or a cyclization self-elimination linker; $L^2$ is a bond or a second self-immolative linker; wherein if $L^1$ is a second self-immolative linker or a cyclization self-elimination linker, then $L^2$ is a bond; and wherein if $L^2$ is a second self-immolative linker, then $L^1$ is a bond. Thus, there is an optional second self-immolative linker or a cyclization self-elimination linker adjacent the hydrophilic self-immolative linker.

In certain embodiments, $L^1$ is a bond and $L^2$ is a bond. In certain embodiments, $L^1$ is a second self-immolative linker or a cyclization self-elimination linker and $L^2$ is a bond. In certain embodiments, $L^1$ is a bond and $L^2$ is a second self-immolative linker.

In Formula (I), in certain embodiments, $L^1$ is a bond. In certain embodiments, $L^1$ is a second self-immolative spacer or a cyclization self-elimination linker, which separates the hydrophilic self-immolative linker and the drug moiety. In certain embodiments, $L^1$ is an aminobenzyloxycarbonyl linker.

In certain embodiments, L¹ is selected from:

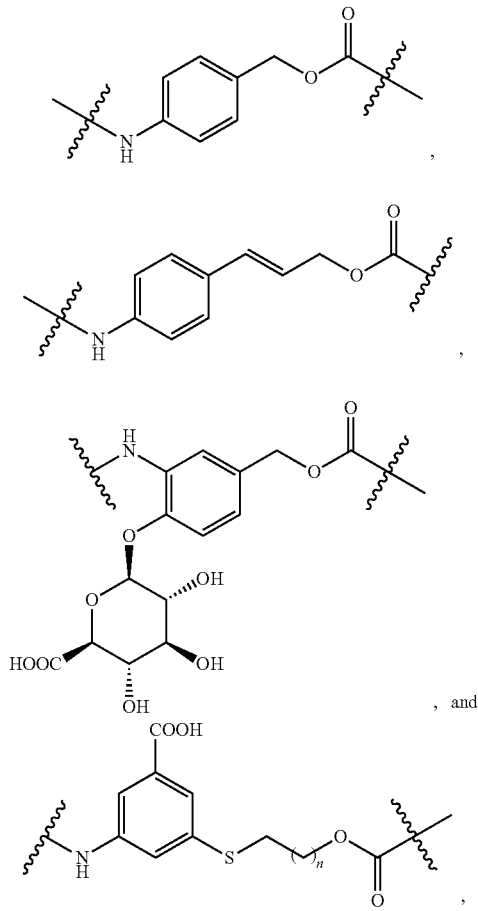

wherein n is 1 or 2.

In certain instances, the second self-immolative linker or cyclization self-elimination linker provides design potential for a wider variety of moieties that can be used. For example, in Formula (II), a carbamate linkage (—O—C(O)—N(H)—) linkage between the hydrophilic self-immolative linker and the drug moiety would provide a stable drug conjugate and would readily cleave to provide a free drug moiety. The hydrophilic self-immolative linker will typically terminate with an oxycarbonyl group (—O—C(O)—). If the drug moiety has an amino-reactive group that may be used to react to form a carbamate group, then the second self-immolative unit or cyclization self-elimination linker is not necessary; although it may still be employed. However, if the drug does not contain an amino group, but instead contains some other reactive functional group, then such drugs may still be incorporated into an aminobenzyloxycarbonyl-containing compound of the present embodiments by including a second, intermediate self-immolative spacer or cyclization self-elimination linker between the drug moiety and the aminobenzyloxycarbonyl group.

The cyclization self-elimination linkers of L¹ below provide linkage of hydroxyl-containing or thiol-containing drug moieties to the aminobenzyloxycarbonyl group of the hydrophilic self-immolative linker:

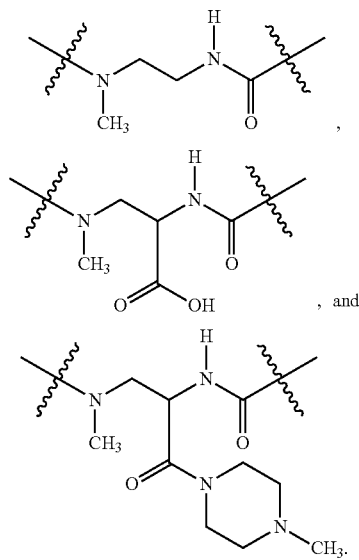

The cyclization self-elimination linkers in the compounds of the embodiments provide for cleavage of the compound to release the drug moiety. The elimination mechanism of the adjacent hydrophilic self-immolative linker would reveal an amino group of L¹. The amino group can then react with the carbamate group or thiocarbamate linkage of L¹ and the drug moiety in a cyclization reaction to release the hydroxyl-containing or thiol-containing drug moiety.

In Formula (I), in certain embodiments, L² is a bond. In certain embodiments, L² is a second self-immolative spacer which separates the hydrophilic self-immolative linker and the peptide linker. In certain embodiments, L² is an aminobenzyloxycarbonyl linker.

In certain embodiments, L² is selected from

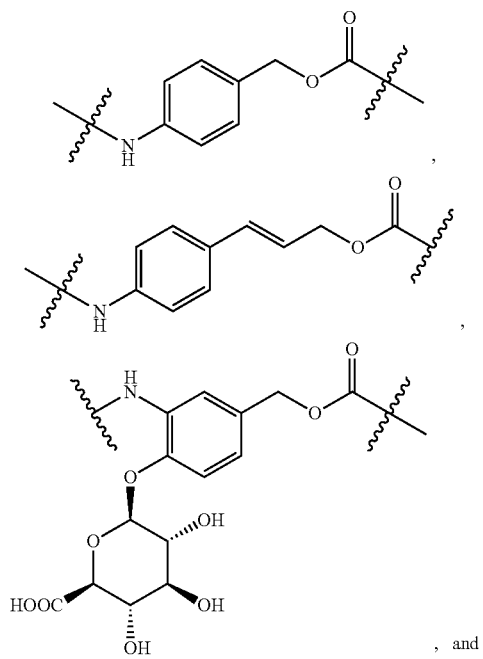

-continued

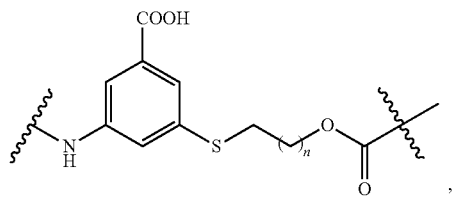

wherein n is 1 or 2.

Optional Spacer

In Formula (I), $L^4$ is a bond or a spacer. In certain embodiments, $L^4$ is a bond. In certain embodiments, $L^4$ is a spacer, which can provide distance between the drug moiety and the targeting moiety.

In certain embodiments, a spacer is selected from alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, and heteroatoms, and combinations thereof. The spacer can be homogenous or heterogeneous in its atom content (e.g., spacers containing only carbon atoms or spacers containing carbon atoms as well as one or more heteroatoms present on the spacer. Preferably, the spacer contains 1 to 50 carbon atoms and 0 to 30 heteroatoms selected from oxygen, nitrogen and sulfur. The spacer may also be chiral or achiral, linear, branched or cyclic.

In certain embodiments, $L^4$ is a spacer selected from polyalkylene glycol, alkylene, alkenylene, alkynylene, and polyamine.

In certain embodiments, $L^4$ is a spacer that comprises a functional group that can provide linkage to the terminal end of the peptide linkage. Functional groups, such as C(O), C(O)—NH, S(O)$_2$, and S(O)$_2$—NH, can provide linkage to the terminal end of the peptide linkage. In certain instances, $L^4$ is $L^{4a}$-C(O), $L^{4a}$-C(O)—NH, $L^{4a}$-S(O)$_2$, $L^{4a}$-S(O)$_2$—NH, wherein $L^{4a}$ is selected from polyalkylene glycol, alkylene, alkenylene, alkynylene, and polyamine. In certain instances, $L^4$ is $L^{4a}$-C(O), wherein $L^{4a}$ is selected from polyalkylene glycol, alkylene, alkenylene, alkynylene, and polyamine.

In certain embodiments, $L^4$ is $L^{4a}$-C(O), wherein $L^{4a}$ is a polyalkylene glycol. In certain embodiments, $L^4$ is $L^{4a}$-C(O), wherein $L^{4a}$ is a polyethylene glycol. In certain embodiments, the spacer is of the formula —CH$_2$—(CH$_2$—O—CH$_2$)$_m$—CH$_2$—C(O)—, wherein m is an integer from 0 to 30.

In certain embodiments, $L^4$ is $L^{4a}$-C(O), wherein $L^{4a}$ is alkylene. In certain embodiments, $L^4$ is $L^{4a}$-C(O), wherein $L^{4a}$ is C$_{1-10}$alkylene, C$_{1-8}$alkylene, or C$_{1-6}$alkylene. In certain embodiments, $L^4$ is $L^{4a}$-C(O), wherein $L^{4a}$ is C$_4$alkylene, C$_5$alkylene, or C$_6$alkylene. In certain embodiments, $L^4$ is $L^{4a}$-C(O), wherein $L^{4a}$ is C$_5$alkylene.

Acyl Unit

In Formula (I), A is an acyl unit. In certain embodiments, the acyl unit "A" comprises a sulfur atom and is linked to the targeting moiety via a sulfur atom derived from the targeting moiety. In such instance, a dithio bond is formed between the acyl unit and the targeting moiety.

In certain embodiments, A is selected from

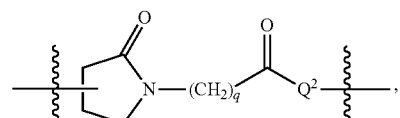

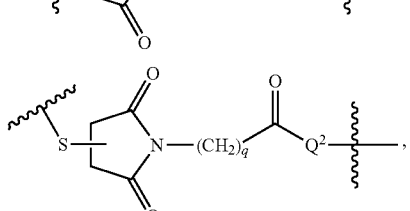

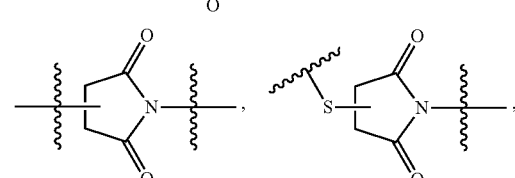

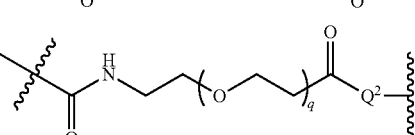

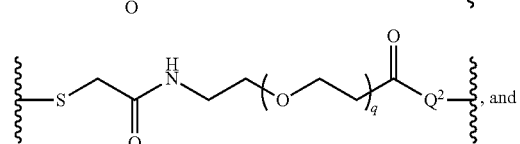

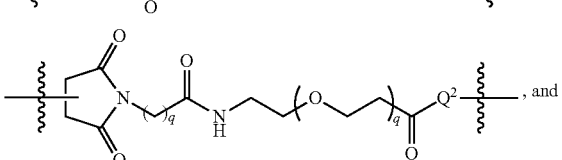

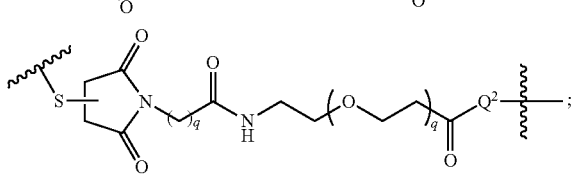

wherein $Q^2$ is NH or O and each q is independently an integer from 1 to 10.

In certain embodiments, A is

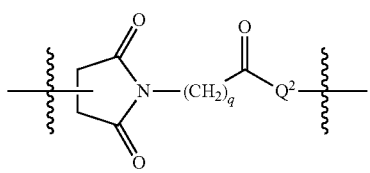

wherein $Q^2$ is NH or O and q is an integer from 1 to 10. In certain instance, q is a number from 2 to 5, such as 2, 3, 4, or 5.

In certain embodiments, A is

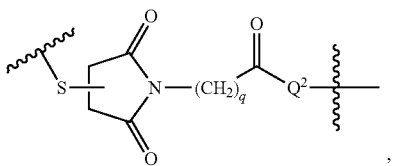

wherein $Q^2$ is NH or O and q is an integer from 1 to 10. In certain instance, q is a number from 2 to 5, such as 2, 3, 4, or 5.

In certain embodiments, A is selected from

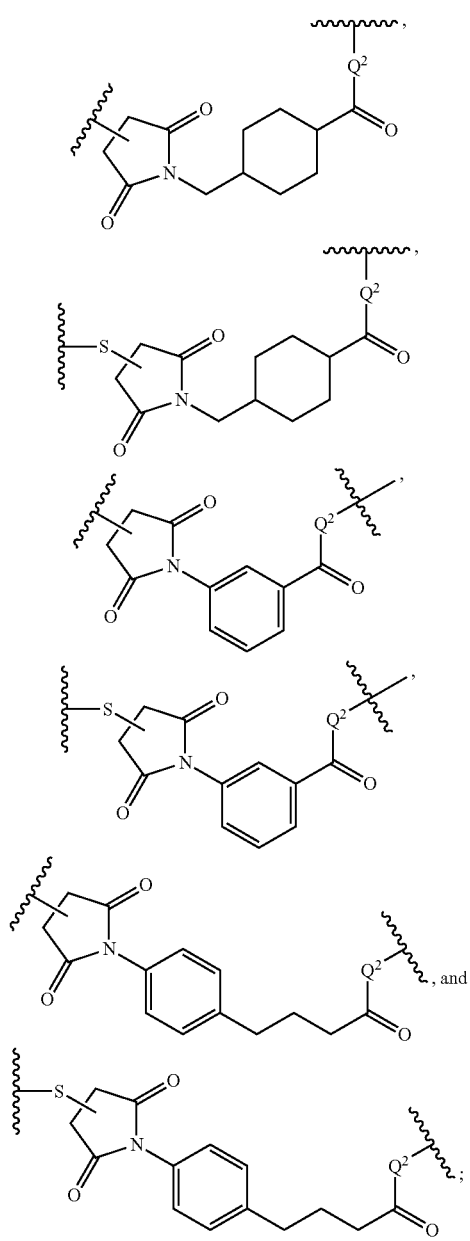

wherein $Q^2$ is NH or O.

Drug Moiety

The drug conjugates of the present embodiments are effective for the usual purposes for which the corresponding drugs are effective, and have superior efficacy because of the ability, inherent in the targeting moiety, to transport the drug to the desired cell where it is of particular benefit.

The preferred drugs for use in the present embodiments are cytotoxic drugs, such as those which are used for cancer therapy. Such drugs include, in general, DNA damaging agents, anti-metabolites, natural products and their analogs. Certain classes of cytotoxic agents include, for example, the enzyme inhibitors such as dihydrofolate reductase inhibitors, thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, differentiation inducers, and taxols. Certain useful members of those classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, carminomycin, aminopterin, tallysomycin, podophyllotoxin and podophyllotoxin derivatives such as etoposide or etoposide phosphate, vinblastine, vincristine, vindesine, taxol, taxotere retinoic acid, butyric acid, $N^8$-acetyl spermidine, camptothecin, and their analogues. Other drugs include dolastatin and duocarmycin.

One skilled in the art may make chemical modifications to the desired compound in order to make reactions of that compound more convenient for purposes of preparing conjugates of the invention.

In certain embodiments, D is a drug moiety having a chemically reactive functional group by means of which the drug is bonded to $L^1$ or X. In certain instances, the functional group is selected from a primary amine, a secondary amine, hydroxyl, and sulfhydryl. In certain instances, the functional group is a primary amine or a secondary amine. In certain instances, the functional group is hydroxyl. In certain instances, the functional group is sulfhydryl.

As discussed above, the hydrophilic self-immolative linker will typically terminate with an oxycarbonyl group (—O—C(O)—). Thus, an amino-containing drug moiety would readily react with the oxycarbonyl group to form a carbamate group. In certain embodiments, D is an amino-containing drug moiety, wherein the drug is connected to $L^1$ or X through the amino group.

However, if the drug moiety does not contain an amino group, the second self-immolative linker or cyclization self-elimination linker of $L^1$ can provide design potential for a wider variety of moieties that can be used. In certain embodiments, D is a hydroxyl-containing or sulhydryl-containing drug moiety, wherein the drug is connected to $L^1$ through the hydroxyl or sulfhydryl group.

Representative amino-containing drugs include mitomycin-C, mitomycin-A, daunorubicin, doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, cytarabine, dolastatin and derivatives thereof. Amino-containing drugs also include amino derivatives of drugs that do not naturally contain an amino group. In certain embodiments, D is duocarmycin, dolastatin, tubulysin, doxorubicin (DOX), paclitaxel, or mitomycin C (MMC), or amino derivatives thereof.

Representative hydroxyl-containing drugs include etoposide, camptothecin, taxol, esperamicin, 1,8-dihydroxy-bicyclo[7.3.1]trideca-4-9-diene-2,6-diyne-13-one, (U.S. Pat. No.

5,198,560), podophyllotoxin, anguidine, vincristine, vinblastine, morpholine-doxorubicin, n-(5,5-diacetoxy-pentyl) doxorubicin, duocarmycin, and derivatives thereof.

Representative sulfhydryl-containing drugs include esperamicin and 6-mercaptopurine, and derivatives thereof.

A certain group of cytotoxic agents for use as drugs in the present embodiments include drugs of the following formulae:

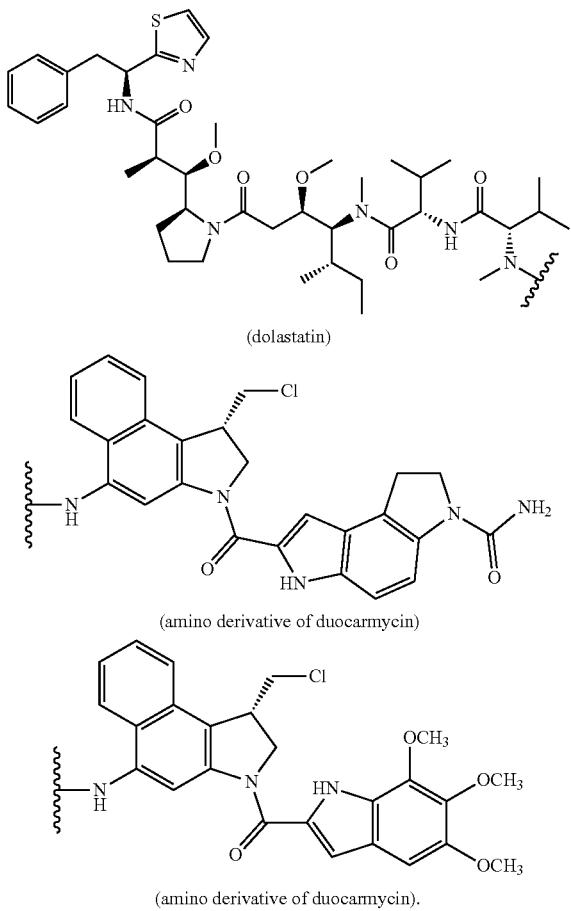

(dolastatin)

(amino derivative of duocarmycin)

(amino derivative of duocarmycin).

Targeting Moiety

A targeting moiety as described in the present disclosure refers to a moiety or molecule that specifically binds, complexes with, reacts with, or associates with a given cell population. For example, a targeting moiety may specifically bind, complex with, react with, or associate with a receptive moiety or receptor associated with a given cell population (e.g., a given cell population sought to be therapeutically treated or otherwise biologically modified). In a conjugate described herein, a targeting moiety described herein is linked via a linker to a drug moiety in the conjugate. In some embodiments, the targeting moiety is capable of delivering a drug moiety (e.g., a drug moiety used for therapeutic purpose) to a particular target cell population which the targeting moiety binds, complexes with, reacts with, or associates with.

The targeting moiety may include, for example, large molecular weight proteins such as, for example, antibodies, smaller molecular weight proteins, polypeptide or peptide, and non-peptidyl moiety. A protein, polypeptide, or peptide moiety described herein may include, for example, transferrin, serum albumin, epidermal growth factors ("EGF"), bombesin, gastrin, gastrin-releasing peptide, platelet-derived growth factor, IL-2, IL-6, tumor growth factors ("TGF"), such as TGF-α, and TGF-β, vaccinia growth factor ("VGF"), insulin and insulin-like growth factors I and II. Non-peptidyl moiety may include, for example, carbohydrates, lectins, and apoprotein from low density lipoprotein. A protein, an antibody, a polypeptide, or a peptide in certain embodiments may refer to its unmodified form, a form that has been modified for being used in a conjugate described herein such as being used to bond to a linker, or a moiety that is in a conjugate described herein.

In some embodiments, the targeting moiety is an antibody (or an antibody moiety or an antibody targeting moiety). In some embodiments, the targeting moiety comprises an antibody. In some embodiments, the targeting moiety comprises sulfhydryl (—SH) group (e.g., a free reactive sulfhydryl (—SH) group) or can be modified to contain such a sulfhydryl group. In some embodiments, the targeting moiety comprises an antibody with a sulfhydryl group (e.g., a free reactive sulfhydryl group). In some embodiments, the targeting moiety comprises a free thiol group such as an antibody with a free thiol group or can be modified to contain such a thio group. In some embodiments, the targeting moiety comprising a sulfhydryl group or thiol group bonds to a linker via the sulfur atom in the sulfhydryl group.

In some embodiments, the targeting moiety is an antibody or an antibody targeting moiety. An antibody described herein refers to an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact polyclonal or monoclonal antibodies, but also antigen-binding fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An antibody included or used in a targeting moiety described herein (or an antibody targeting moiety) can encompass monoclonal antibodies, polyclonal antibodies, antibody fragments (e.g., Fab, Fab', F(ab')$_2$, Fv, Fc, etc.), chimeric antibodies, humanized antibodies, human antibodies (e.g., fully human antibodies), single chain (ScFv), bispecific antibodies, multispecific antibodies, mutants thereof, fusion proteins comprising an antibody portion, and any other modified configuration of the immunoglobulin molecule that comprises an antigen recognition site of the required specificity. The antibodies may be murine, rat, camel, human, or any other origin (including humanized antibodies). In some embodiments, an antibody used in a targeting moiety described herein (or an antibody targeting moiety) is any one of the following: bispecific antibody, multispecific, single-chain, bifunctional, and chimeric and humanized molecules having affinity for a polypeptide conferred by at least one hypervariable region (HVR) or complementarity determining region (CDR) of the antibody. Antibodies used in the present disclosure also include single domain antibodies which are either the variable domain of an antibody heavy chain or the variable domain of an antibody light chain. Holt et al., *Trends Biotechnol.* 21:484-490, 2003. Methods of making domain antibodies comprising either the variable domain of an antibody heavy chain or the variable domain of an antibody light chain, containing three of the six naturally occurring HVRs or CDRs from an antibody, are also known in the art. See, e.g., Muyldermans, *Rev. Mol. Biotechnol.* 74:277-302, 2001.

In some embodiments, an antibody included or used in a targeting moiety described herein (or an antibody targeting moiety) is a monoclonal antibody. As used herein, a monoclonal antibody refers to an antibody of substantially homogeneous antibodies, i.e., the individual antibodies comprising the population are identical except for possible naturally-occurring mutations that may be present in minor amounts. Furthermore, in contrast to polyclonal antibody preparations, which typically include different antibodies directed against different determinants (epitopes), monoclonal antibody is not a mixture of discrete antibodies. The modifier "monoclonal" indicates the character of the antibody as being obtained from a substantially homogeneous population of antibodies, and is not to be construed as requiring production of the antibody by any particular method. For example, the monoclonal antibodies used in the present disclosure may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

In some embodiments, an antibody included or used in a targeting moiety described herein (or an antibody targeting moiety) is a chimeric antibody. As used herein, a chimeric antibody refers to an antibody having a variable region or part of variable region from a first species and a constant region from a second species. An intact chimeric antibody comprises two copies of a chimeric light chain and two copies of a chimeric heavy chain. The production of chimeric antibodies is known in the art (Cabilly et al. (1984), *Proc. Natl. Acad. Sci. USA*, 81:3273-3277; Harlow and Lane (1988), *Antibodies: a Laboratory Manual*, Cold Spring Harbor Laboratory). Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human is less likely to elicit an immune response from a human subject when the antibodies are injected than would the constant region from a non-human source. However, the definition is not limited to this particular example.

In some embodiments, an antibody included or used in a targeting moiety described herein (or an antibody targeting moiety) is a humanized antibody. As used herein, humanized antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a HVR or CDR of the recipient are replaced by residues from a HVR or CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported HVR or CDR or framework sequences, but are included to further refine and optimize antibody performance. In general, the humanized antibody will comprise substantially all of at least one, and typically two, variable domains, in which all or substantially all of the HVR or CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more HVRs or CDRs (one, two, three, four, five, six) which are altered with respect to the original antibody, which are also termed one or more HVRs or CDRs "derived from" one or more HVRs or CDRs from the original antibody.

In some embodiments, an antibody included or used in a targeting moiety described herein (or an antibody targeting moiety) is a human antibody. As used herein, a human antibody means an antibody having an amino acid sequence corresponding to that of an antibody produced by a human and/or has been made using any of the techniques for making human antibodies known in the art. A human antibody used herein includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

In some embodiments, an antibody included or used in a targeting moiety described herein (or an antibody targeting moiety) specifically binds to an antigen on a cancer cell such as a nonhematopoietic cancer cell (e.g., colorectal, pancreatic, or gastric cancer cell). In some embodiments, the antibody specifically binds to a carbohydrate-containing epitope on CD43, for example, an antibody described in U.S. Pat. No.

7,674,605, U.S. Pat. No. 7,982,017, PCT/US2007/013587 (Publication No. WO 2007/146172), or PCT/US2008/087515 (Publication No. WO 2009/079649), the contents of each of which are incorporated herein by reference. In some embodiments, the antibody is h5F1Ca.1 antibody.

Table 1 below shows the amino acid sequence of humanized 5F1Ca.1 (h5F1Ca.1) heavy and light chain.

HVRs (or CDRs) from SEQ ID NO:1 and/or a light chain variable region comprising one, two or three HVRs (or CDRs) from SEQ ID NO:2. In some embodiments, the antibody comprises a heavy chain variable region comprising the three HVRs (or CDRs) from SEQ ID NO:1 and/or a light chain variable region comprising the three HVRs (or CDRs) from SEQ ID NO:2. In some embodiments, the antibody Table 1(A)

h5F1Ca.1 heavy chain amino acid sequence (SEQ ID NO: 1)
(Kabat CDRs in some embodiments are underlined; the sequence in constant region is italicized)

```
  1 QVQLVQSGAEVKKPGASVKMSCKASGYTFTSYVMHWIRQAPGQGLEWIGYINPYNGGTQY

61 NEKFKGRATLTSDTSASTAYMELSSLRSEDTAVYYCARRTFPYYFDYWGQGTLLTVSSAS

121 TKGPSVFPLAPSSKSTSGGTAALGCLVKDYFPEPVTVSWNSGALTSGVHTFPAVLQSSGL

181 YSLSSVVTVPSSSLGTQTYICNVNHKPSNTKVDKKVEPKSCDKTHTCPPCPAPELLGGPS

241 VFLFPPKPKDTLMISRTPEVTCVVVDVSHEDPEVKFNWYVDGVEVHNAKTKPREEQYNST

301 YRVVSVLTVLHQDWLNGKEYKCKVSNKALPAPIEKTISKAKGQPREPQVYTLPPSRDELT

361 KNQVSLTCLVKGFYPSDIAVEWESNGQPENNYKTTPPVLDSDGSFFLYSKLTVDKSRWQQ

421 GNVFSCSVMHEALHNHYTQKSLSLSPGK (SEQ ID NO: 1)
```

Table 1(B)

h5F1Ca.1 light chain amino acid sequence (SEQ ID NO: 2)
(Kabat CDRs in some embodiments are underlined; the sequence in constant region is italicized)

```
  1 DVVMTQTPLSLPVTLGEPASISCRSSQSILHSNGNTYLEWYLQKPGQSPKLLIYKVSNRF

61 SGVPDRFSGSGSGTDFTLKISRVEAEDVGVYYCFQGSHAPLTFGGGTKLEIKRTVAAPSV

121 FIFPPSDEQLKSGTASVVCLLNNFYPREAKVQWKVDNALQSGNSQESVTEQDSKDSTYSL

181 SSTLTLSKADYEKHKVYACEVTHQGLSSPVTKSFNRGEC (SEQ ID NO: 2)
```

In some embodiments, the antibody is antibody h5F1Ca.1 or an antibody derived from antibody h5F1Ca.1. The heavy chain and light chain sequences of h5F1Ca.1 are set forth in SEQ ID NO:1 and SEQ ID NO:2, respectively. In some embodiments, the antibody comprises one, two, or three HVRs (or CDRs) from a light chain and/or a heavy chain of the antibody h5F1Ca.1 (or an antibody derived from antibody h5F1Ca.1). In some embodiments, the antibody comprises a fragment or a region of the antibody h5F1Ca.1. In one embodiment, the fragment is a light chain of the antibody h5F1Ca.1. In another embodiment, the fragment is a heavy chain of the antibody h5F1Ca.1. In yet another embodiment, the fragment comprises one or more variable regions from a light chain and/or a heavy chain of the antibody h5F1Ca.1 (or an antibody derived from h5F1Ca.1). In yet another embodiment, the fragment comprises one, two, or three HVRs (or CDRs) from a light chain and/or a heavy chain of the antibody h5F1Ca.1 (or an antibody derived from h5F1Ca.1). In some embodiments, the one or more HVRs (or CDRs) derived from antibody h5F1Ca.1 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six HVRs (or CDRs) of h5F1Ca.1. In some embodiments, the antibody comprises a heavy chain variable region comprising one, two or three comprises a heavy chain variable region comprising amino acids 1-118 of SEQ ID NO: 1 and/or a light chain variable region comprising amino acids 1-113 of SEQ ID NO: 2. In some embodiments, the antibody is chimeric antibody. In some embodiments, the antibody is humanized antibody.

In some embodiments, an antibody included or used in a targeting moiety described herein (or an antibody targeting moiety) specifically binds to a transferrin receptor (such as human transferrin receptor) expressed by nonhematopoietic cancer cells (e.g., lung, ovarian, breast, prostate, liver, endometrial, colorectal, pancreatic, or gastric cancer cell). The antibody may specifically bind to a modification (such as a carbohydrate) on a transferrin receptor expressed by nonhematopoietic cancer cells. In some embodiments, the antibody specifically binds to a carbohydrate on a transferrin receptor expressed by nonhematopoietic cancer cells. In some embodiments, the antibody specifically binds to a carbohydrate-containing epitope on a transferrin receptor, for example, an antibody described in U.S. Provisional Patent Application No. 61/584,125, filed Jan. 6, 2012, the contents of which are incorporated by reference in their entirety. In some embodiments, the antibody is chimeric 5D7-54.17 antibody (c5D7), 5D7-54.17, or an antibody derived from 5D7-54.17 antibody (e.g., as described in U.S. Provisional Patent Application No. 61/584,125). In some embodiments, the antibody is c5D7 antibody.

Table 2 below shows the amino acid sequences of the heavy chain sequence and light chain sequence of c5D7 antibody.

Table 2(A)

c5D7 Heavy chain sequence (SEQ ID NO: 3)
(Kabat CDRs in some embodiments are underlined; the sequence
in constant region is italicized)

1 EVQLQQSGPEVVKPGASMKMSCKTSGYKFT<u>GYYMD</u>WVKQSLGASFEWIG<u>RVIPSNGDTRY</u>

61 <u>NQKFEG</u>KATLTVDRSSSTAYMELNSLTSEDSAVYYCAR<u>KPLSGNAADY</u>WGQGTSVTVSTA

121 *STKGPSVFPLAPSSKSTSGGTAALGCLVKDYFPEPVTVSWNSGALTSGVHTFPAVLQSSG*

181 *LYSLSSVVTVPSSSLGTQTYICNVNHKPSNTKVDKKVEPKSCDKTHTCPPCPAPELLGGP*

241 *SVFLFPPKPKDTLMISRTPEVTCVVVDVSHEDPEVKFNWYVDGVEVHNAKTKPREEQYNS*

301 *TYRVVSVLTVLHQDWLNGKEYKCKVSNKALPAPIEKTISKAKGQPREPQVYTLPPSRDEL*

361 *TKNQVSLTCLVKGFYPSDIAVEWESNGQPENNYKTTPPVLDSDGSFFLYSKLTVDKSRWQ*

421 *QGNVFSCSVMHEALHNHYTQKSLSLSPGK* (SEQ ID NO: 3)

Table 2(B)

c5D7 Light chain sequence (SEQ ID NO: 4)
(Kabat CDRs in some embodiments are underlined; the sequence
in constant region is italicized)

1 ETTVTQSPASLSVATGEKVTIRC<u>ITSTDIDDDMN</u>WYQQKPGEPPKLLIS<u>DGNTLRP</u>GVPS

61 RFSSSGYGTDFVFTIENTLSEDITDYYC<u>MQSDNMPFT</u>FGSGTKLEIKRT*VAAPSVFIFPP*

121 *SDEQLKSGTASVVCLLNNFYPREAKVQWKVDNALQSGNSQESVTEQDSKDSTYSLSSTLT*

181 *LSKADYEKHKVYACEVTHQGLSSPVTKSFNRGEC* (SEQ ID NO: 4)

In some embodiments, the antibody is c5D7 antibody or an antibody derived from c5D7 antibody. The heavy chain and light chain sequences of c5D7 antibody are set forth in SEQ ID NO:3 and SEQ ID NO:4, respectively (see Table 2). In some embodiments, the antibody comprises one, two, or three HVRs (or CDRs) from a light chain and/or a heavy chain of the c5D7 antibody (or an antibody derived from c5D7 antibody). In some embodiments, the antibody comprises a fragment or a region of the antibody c5D7 antibody. In one embodiment, the fragment is a light chain of the c5D7 antibody. In another embodiment, the fragment is a heavy chain of the c5D7 antibody. In yet another embodiment, the fragment comprises one or more variable regions from a light chain and/or a heavy chain of the c5D7 antibody (or an antibody derived from c5D7 antibody). In yet another embodiment, the fragment comprises one, two, or three HVRs (or CDRs) from a light chain and/or a heavy chain of the c5D7 antibody (or an antibody derived from c5D7). In some embodiments, the one or more HVRs (or CDRs) derived from c5D7 antibody are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six HVRs (or CDRs) of c5D7 antibody. In some embodiments, the antibody comprises a heavy chain variable region comprising one, two or three HVRs (or CDRs) from SEQ ID NO:3 and/or a light chain variable region comprising one, two or three HVRs (or CDRs) from SEQ ID NO:4. In some embodiments, the antibody comprises a heavy chain variable region comprising the three HVRs (or CDRs) from SEQ ID NO:3 and/or a light chain variable region comprising the three HVRs (or CDRs) from SEQ ID NO:4. In some embodiments, the antibody comprises a heavy chain variable region comprising amino acids 1-119 of SEQ ID NO: 3 and/or a light chain variable region comprising amino acids 1-108 of SEQ ID NO: 4. In some embodiments, the antibody is chimeric antibody. In some embodiments, the antibody is humanized antibody.

As used herein, "percent (%) amino acid sequence identity" and "homology" with respect to a sequence refers to the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

In some embodiments, a CDR described herein is Kabat CDR, Chothia CDR, or contact CDR. In some embodiments, the CDR is a Kabat CDR. In some embodiments, the CDR is a Chothia CDR. In other embodiments, the CDR is a combination of a Kabat and a Chothia CDR (also termed "combined CDR" or "extended CDR"). In other words, for any given embodiment containing more than one CDR, the CDRs may be any of Kabat, Chothia, and/or combined. Methods of determining CDRs are known in the field.

A variable region of an antibody refers to the variable region of the antibody light chain or the variable region of the antibody heavy chain, either alone or in combination. Generally, the variable region(s) mediate antigen binding and define specificity of a particular antibody for its particular antigen. The variable regions may have relatively invariant stretches called framework regions (FRs) (e.g., FR of 15-30 amino acids) separated by shorter regions of extreme variability called "hypervariable regions" ("HVR") (e.g., HVRs that are each 9-12 amino acids long). In some embodiments, the variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain may be held together in close proximity by the FRs and, with the hypervariable regions from the other chain, contribute to the formation of the antigen-binding site of antibodies (see Kabat et al., Sequences of Proteins of Immunological Interest. 5th Ed. Public Health Service, National Institutes of Health, Bethesda, Md. (1991)). The constant domains may not be involved directly in binding an antibody to an antigen, but may exhibit various effector functions, such as participation of the antibody in antibody dependent cellular cytotoxicity (ADCC). A constant region of an antibody refers to the constant region of the antibody light chain or the constant region of the antibody heavy chain, either alone or in combination. A constant region of an antibody generally provides structural stability and other biological functions such as antibody chain association, secretion, transplacental mobility, and complement binding, but is not involved with binding to the antigen. The amino acid sequence and corresponding exon sequences in the genes of the constant region will be dependent upon the species from which it is derived; however, variations in the amino acid sequence leading to allotypes will be relatively limited for particular constant regions within a species. The variable region of each chain is joined to the constant region by a linking polypeptide sequence. The linkage sequence is coded by a "J" sequence in the light chain gene, and a combination of a "D" sequence and a "J" sequence in the heavy chain gene.

The term "hypervariable region" ("HVR") when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the VL, and around about 31-35B (H1), 50-65 (H2) and 95-102 (H3) in the VH (in one embodiment, H1 is around about 31-35); Kabat et al., Sequences of Proteins of Immunological Interest. 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the VL, and 26-32 (H1), 53-55 (H2) and 96-101 (H3) in the VH; Chothia and Lesk J. Mol. Biol. 196:901-917 (1987)). There are multiple ways for determining CDRs, for example, an approach based on cross-species sequence variability (i.e., Kabat et al. Sequences of Proteins of Immunological Interest, (5th ed., 1991, National Institutes of Health, Bethesda Md.)); and an approach based on crystallographic studies of antigen-antibody complexes (Al-lazikani et al. (1997) J. Molec. Biol. 273:927-948)). The HVRs that are Kabat complementarity-determining regions (CDRs) are based on sequence variability and are the most commonly used (Kabat et al., supra). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. As used herein, a CDR may be a CDR defined by any of the approaches or by a combination of any two or three of the approaches. The CDR may be Kabat CDR, Chothia CDR, or contact CDR. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

In some embodiments, the antibody is isolated. An isolated antibody refers to an antibody which has been identified and separated and/or recovered from a component of its natural environment. In some embodiments, the antibody is substantially pure. The term "substantially pure" may refer to material which is at least 50% pure (i.e., free from contaminants), more preferably at least 90% pure, more preferably at least 95% pure, more preferably at least 98% pure, more preferably at least 99% pure. In some embodiments, the antibody is a monoclonal antibody. In some embodiments, the antibody is a humanized antibody. In some embodiments, the antibody is a chimeric antibody. In some embodiments, the antibody is a human antibody. In some embodiments, the antibody is IgG (such as $IgG_1$, $IgG_2$, or $IgG_4$). In some embodiments, the antibody is human IgG such as human $IgG_1$.

The antibodies described herein may further include analogs and derivatives that are either modified, i.e., by the covalent attachment of any type of molecule as long as such covalent attachment permits the antibody to retain its antigen binding immunospecificity. For example, the derivatives and analogs of the antibodies include those that have been further modified, e.g., by glycosylation, acetylation, pegylation, phosphylation, amidation, derivatization by known protecting/blocking groups, proteolytic cleavage, linkage to a cellular ligand or other protein, etc. Chemical modifications can be carried out by known techniques, including, but not limited to specific chemical cleavage, acetylation, formulation, etc. Additionally, the analog or derivative can contain one or more unnatural amino acids.

The antibodies described herein may include antibodies immunospecific for a cancer cell antigen or an antibody for treatment of cancer. Methods of making antibodies immunospecific for a cancer cell antigen are known in the art. The antibodies may include any of the following: anti-HER2 antibody such as a humanized anti-HER2 monoclonal antibody (e.g., HERCEPTIN (Trastuzumab; Genentech, CA)), anti-CD20 antibody such as a chimeric anti-CD20 monoclonal antibody (e.g., RITUXAN (rituximab; Genentech)), OvaRex (AltaRex Corporation, MA), Panorex (Glaxo Wellcome, NC), BEC2 (ImClone Systems Inc., NY), IMC-C225 (Imclone Systems Inc., NY), Vitaxin (MedImmune, Inc., MD), Campath I/H (Leukosite, MA), Smart MI95 (Protein Design Labs, Inc., CA), LymphoCide (Immunomedics, Inc., NJ), Smart ID10 (Protein Design Labs, Inc., CA), Oncolym (Techniclone, Inc., CA), anti-CD2 antibody such as humanized anti-CD2 mAb (e.g., Allomune (BioTransplant, CA)), anti-VEGF antibody such as humanized anti-VEGF antibody (e.g., bevacizumab (Genentech, Inc., CA)), CEAcide (Immunomedics, NJ), anti-KDR antibody such as an anti-KDR chimeric antibody (e.g., IMC-1C11 (ImClone Systems, NJ)), anti-EGFR antibody such as anti-EGFR chimeric antibody (e.g., Cetuximab (ImClone, NJ)), BR96 mAb (Trail, P. A. et al., Science 1993, 261, 212-215), BR64 (Trail, P A et al., Cancer Research 1997, 57, 100-105), anti-CD30 antibody, and mAbs against the CD 40 antigen such as S2C6 mAb. The antibodies may further include antibodies against any of the following antigens: CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, CEA, gp100, MART1, PSA, IL-2 receptor, CD20, CD52, CD33, CD22, human chorionic gonadotropin, CD38, CD40, mucin, P21, MPG and Neu oncogene product.

The antibodies described herein may further include antibodies that can bind to both a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFα-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin. The antibodies described herein may further include antibodies that are immunospecific for a viral or a microbial antigen. A viral antigen may include any of the following: a viral peptide, polypeptide protein (e.g., HIV gp120, HIV nef, RSV F glycoprotein, influenza virus neuramimidase, influenza virus hemagglutinin, HTLV tax, herpes simplex virus glycoprotein (e.g., gB, gC, gD, and gE) and hepatitis B surface antigen) that is capable of eliciting an immune response. A microbial antigen may include any of the following: a microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Methods of making a targeting moiety (e.g., an antibody, a polypeptide, a peptide, or non-peptidyl moiety) are known in the art, such as the methods described in U.S. Pat. No. 7,674,605, U.S. Pat. No. 7,982,017, PCT/US2007/013587 (Publication No. WO 2007/146172), or PCT/US2008/087515 (Publication No. WO 2009/079649).

Representative Linkers

In certain instances, the "-A-L$^4$-L$^3$-L$^2$-" or "-A-L$^4$-L$^3$-" portion in the compound of Formula (I) or (II) is:

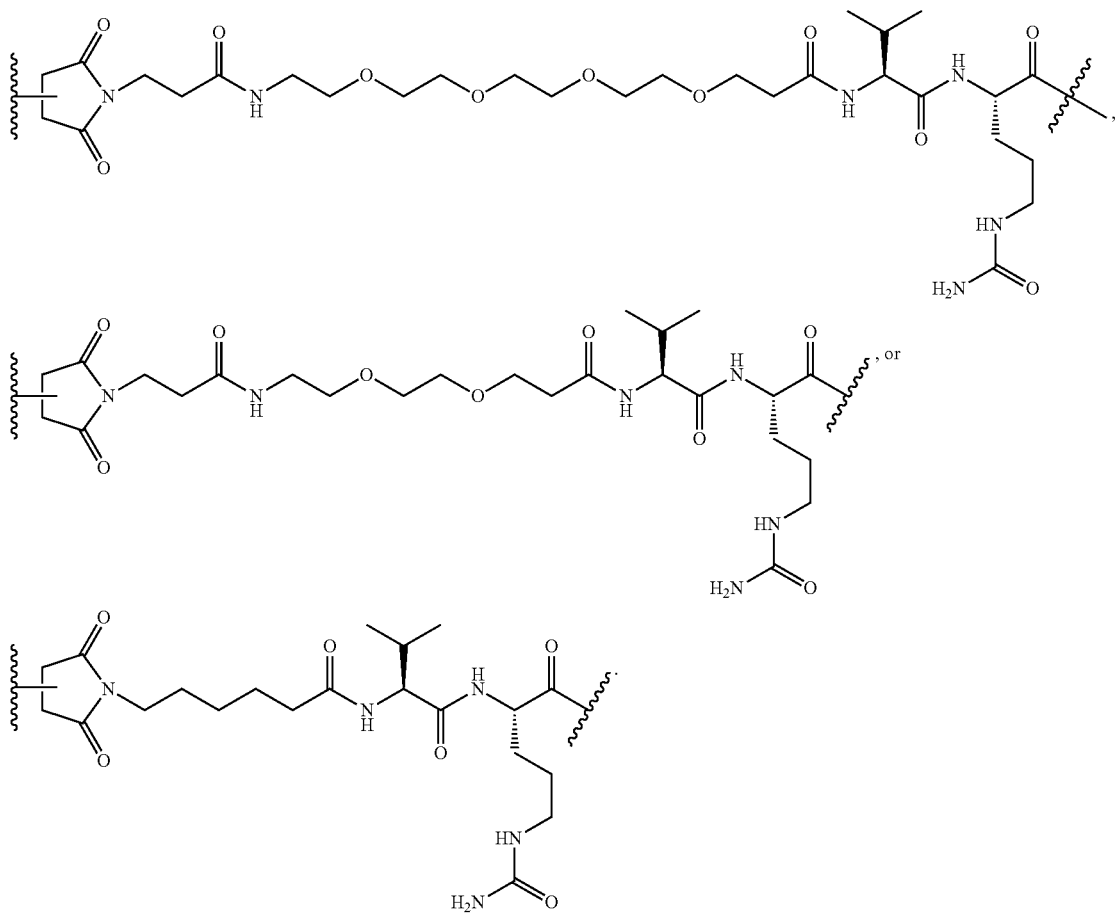

In certain instances, the "-A-L$^4$-L$^3$-L$^2$-" or "-A-L$^4$-L$^3$-" portion in the compound of Formula (I) or (II) is:
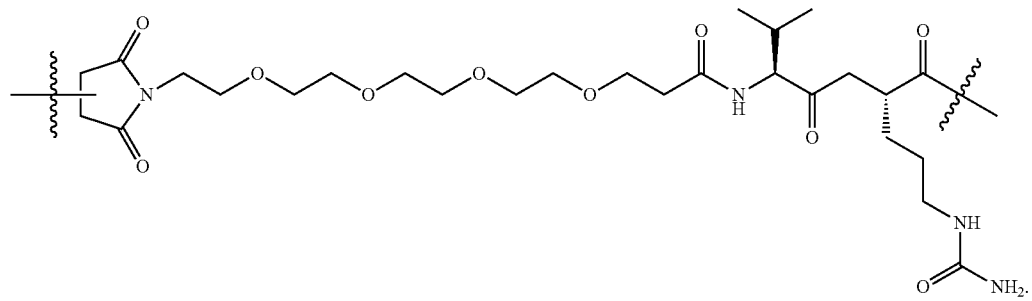
In certain instances, the "-A-L$^4$-L$^3$-L$^2$-" or "-A-L$^4$-L$^3$-" portion in the compound of Formula (I) or (II) is:
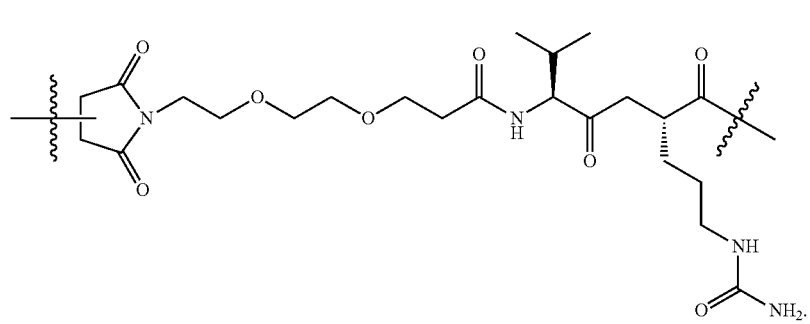
In certain instances, the "-A-L$^4$-L$^3$-L$^2$-X-L$^1$-D" portion in the compound of Formula (I) or (II) is:

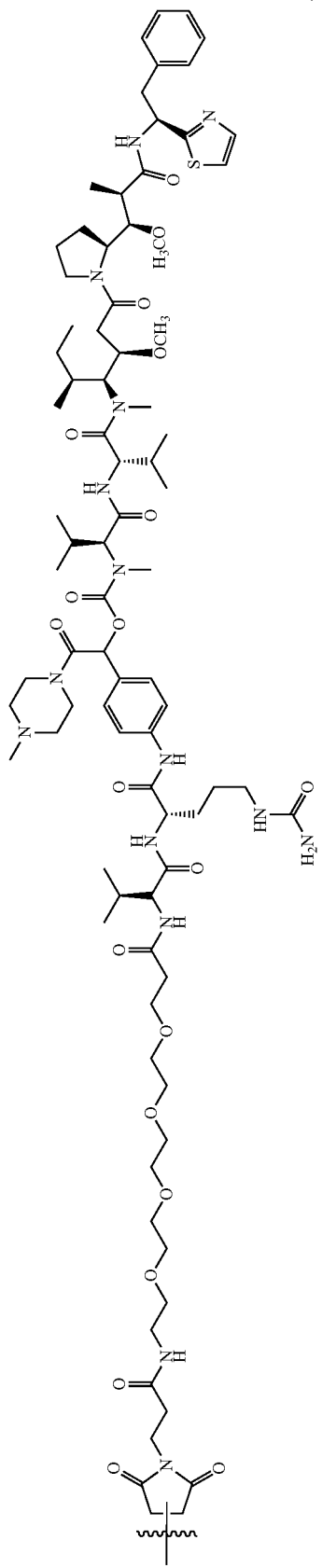

In such instance, the present disclosure provides a compound of Formula (III):

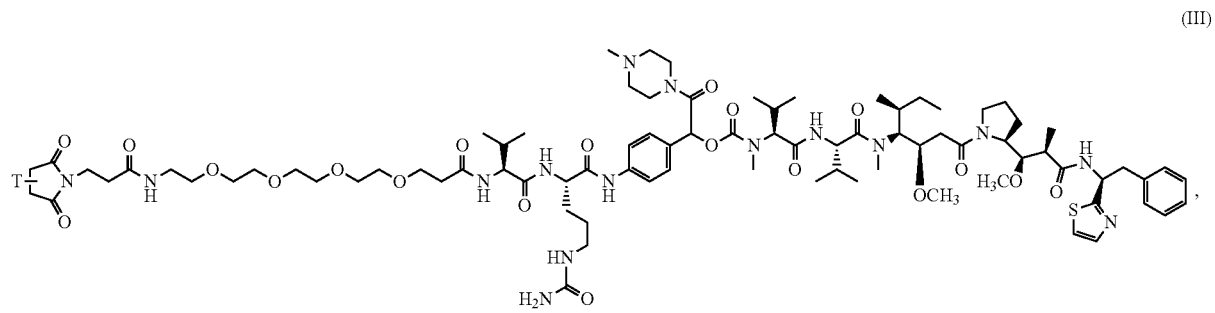

(III)

or a salt or solvate or stereoisomer thereof; wherein T is a targeting moiety. In certain instances, in Formula (III), T is an antibody. In certain embodiments, the antibody is h5F1Ca.1 or c5D7.

In certain embodiments, the present disclosure provides intermediates for synthesis of compounds of Formula (I). The present disclosure provides a compound of Formula (VI):

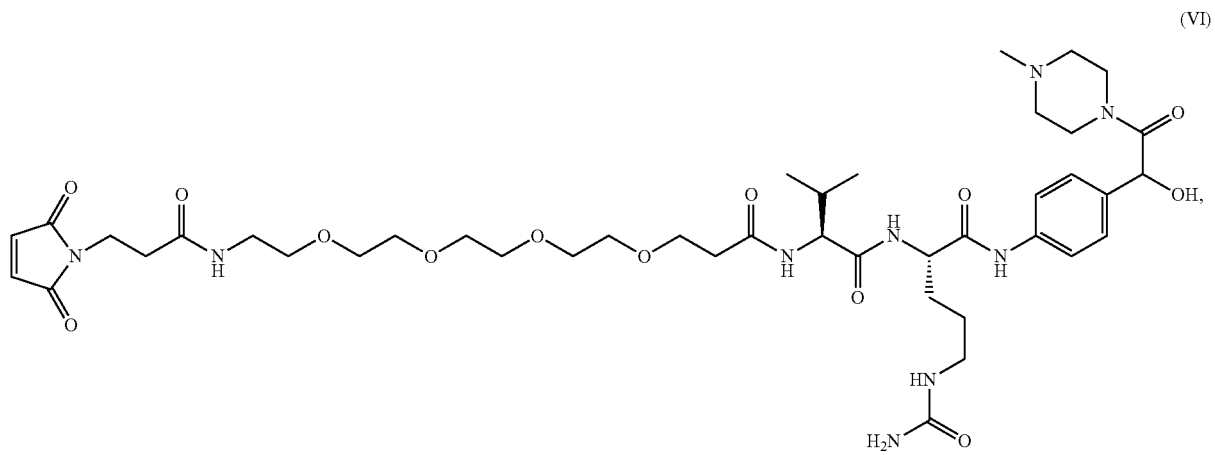 [SMILES: CC(C)[C@H](NC(=O)CCOCCOCCOCCOCCNC(=O)CCN1C(=O)C=CC1=O)C(=O)N[C@@H](CCCNC(N)=O)C(=O)Nc1ccc(C(O)C(=O)N2CCN(C)CC2)cc1]

(VI)

or a salt or solvate thereof

The present disclosure provides a compound of Formula (IX):

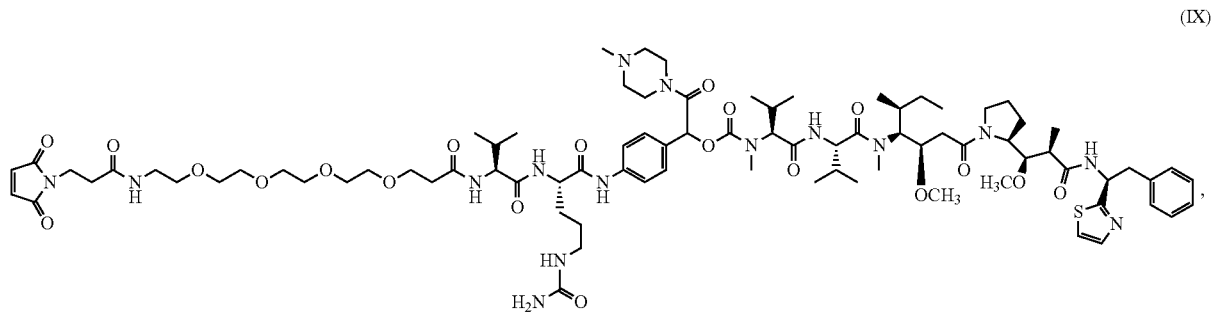 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OC(C(=O)N1CCN(C)CC1)c1ccc(NC(=O)[C@H](CCCNC(N)=O)NC(=O)[C@@H](NC(=O)CCOCCOCCOCCOCCNC(=O)CCN2C(=O)C=CC2=O)C(C)C)cc1)C(C)C]

(IX)

or a salt or solvate thereof.

In certain instances, the "-A-L⁴-L³-L²-X-L¹-D" portion in the compound of Formula (I) or (II) is:

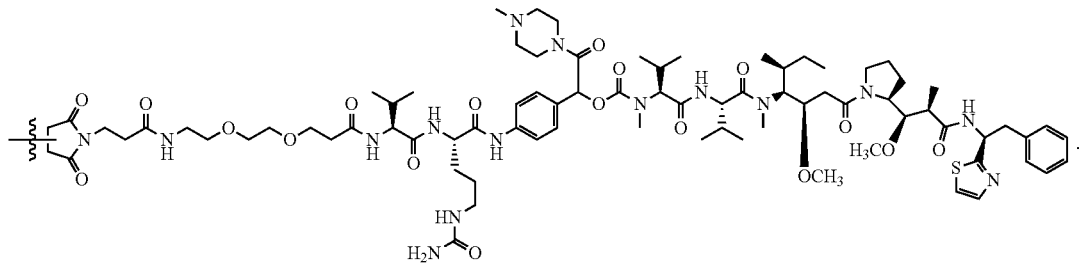

In such instance, the present disclosure provides a compound of Formula (IV):

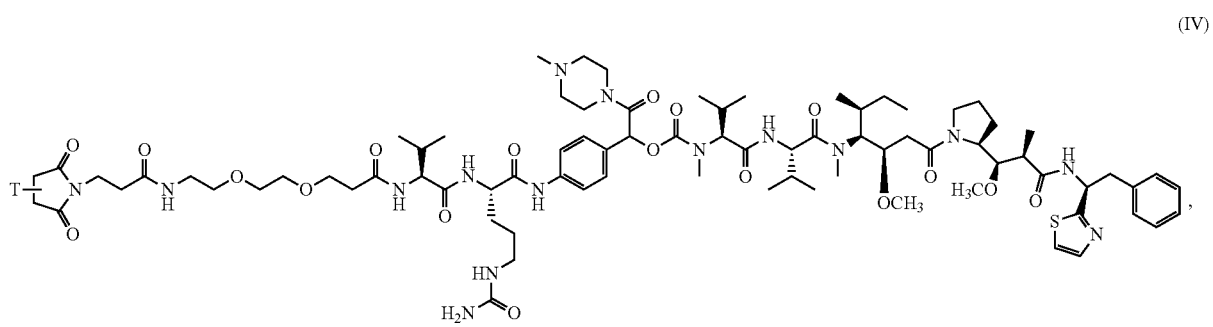

(IV)

or a salt or solvate or stereoisomer thereof; wherein T is a targeting moiety. In certain instances, in Formula (IV), T is an antibody. In certain embodiments, the antibody is h5F1Ca.1 or c5D7.

In certain embodiments, the present disclosure provides intermediates for synthesis of compounds of Formula (I). The present disclosure provides a compound of Formula (VII):

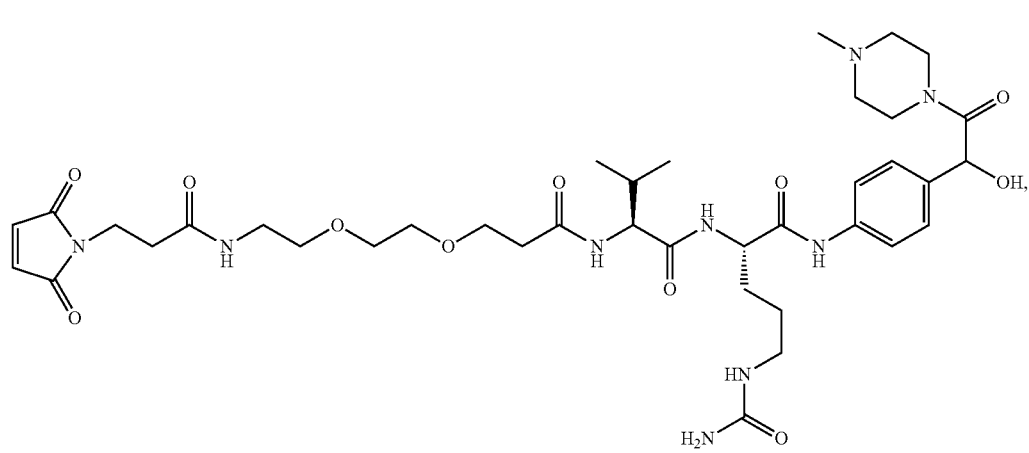

(VII)

or a salt or solvate thereof.

The present disclosure provides a compound of Formula (X):

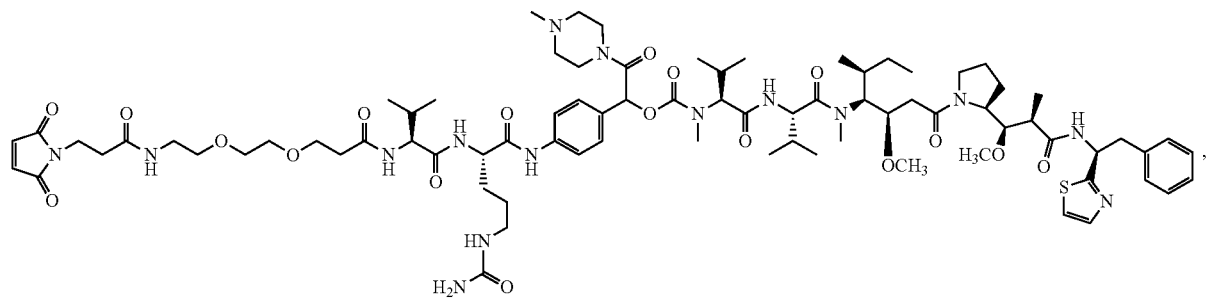

(X)

or a salt or solvate thereof.

In certain instances, the "-A-L$^4$-L$^3$-L$^2$-X-L$^1$-D" portion in the compound of Formula (I) or (II) is:

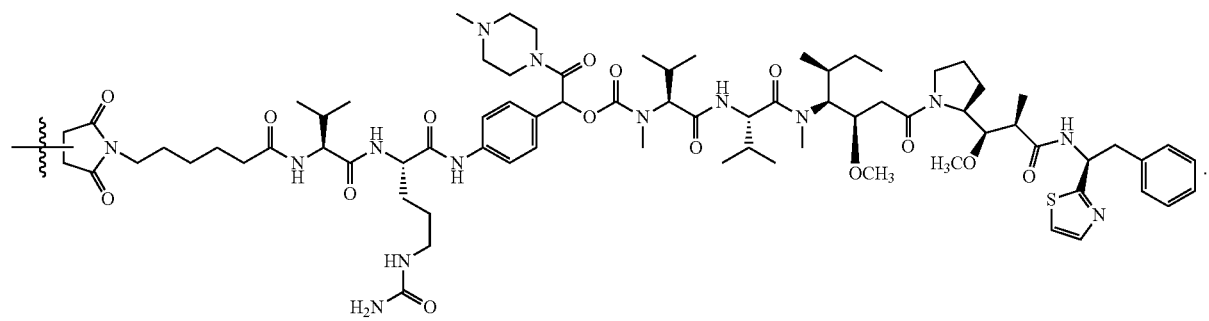

In such instance, the present disclosure provides a compound of Formula (V):

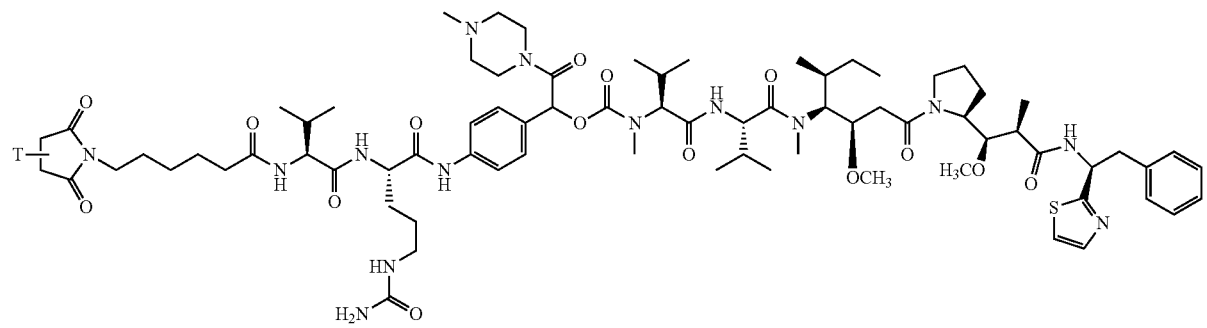

or a salt or solvate or stereoisomer thereof; wherein T is a targeting moiety. In certain instances, in Formula (V), T is an antibody. In certain embodiments, the antibody is h5F1Ca.1 or c5D7.

In certain embodiments, the present disclosure provides intermediates for synthesis of compounds of Formula (I). The present disclosure provides a compound of Formula (VIII):

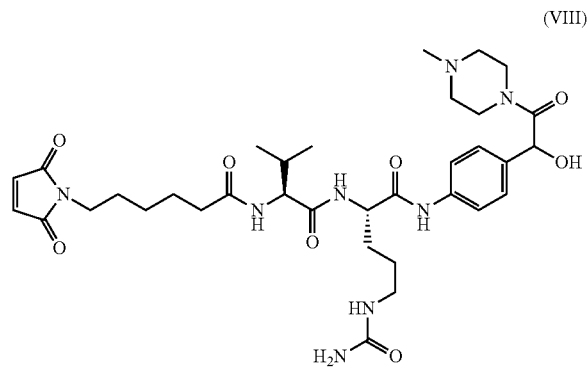 [SMILES: CC(C)[C@H](NC(=O)CCCCCN1C(=O)C=CC1=O)C(=O)N[C@@H](CCCNC(N)=O)C(=O)Nc1ccc(C(O)C(=O)N2CCN(C)CC2)cc1]

(VIII)

or a salt or solvate thereof.

The present disclosure provides a compound of Formula (XI):

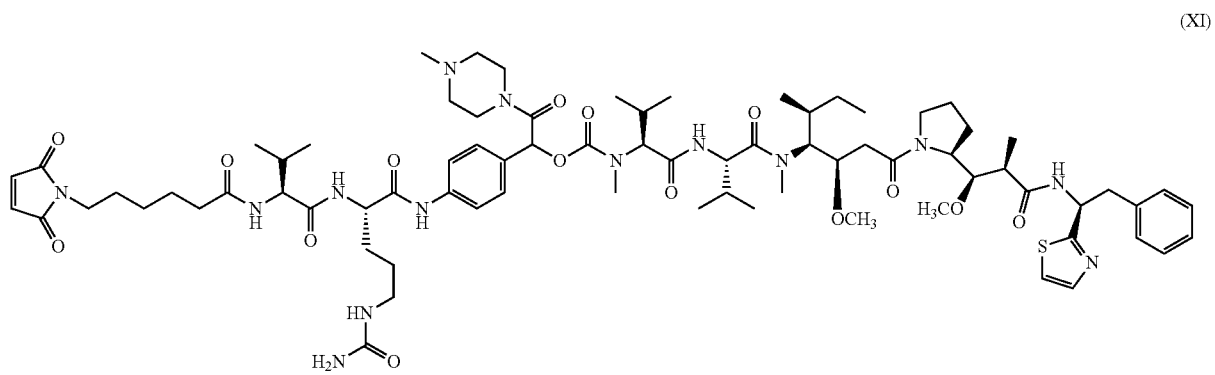 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OC(C(=O)N1CCN(C)CC1)c1ccc(NC(=O)[C@H](CCCNC(N)=O)NC(=O)[C@@H](NC(=O)CCCCCN2C(=O)C=CC2=O)C(C)C)cc1)C(C)C]

(XI)

or a salt or solvate thereof.

The present disclosure provides a compound of Formula (XII)

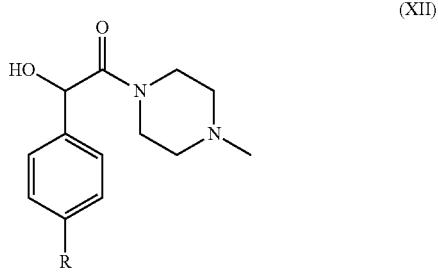

(XII)

or a salt or solvate or stereoisomer thereof; wherein R is $NO_2$ or $NH_2$.

The compounds of Formulae (I)-(V) may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of any one of Formulae (I)-(V) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

Pharmaceutical Compositions

For treatment purposes, a pharmaceutical composition of the embodiments comprises at least one compound of Formulae (I)-(V), or a pharmaceutically acceptable salt thereof. The pharmaceutical compositions may further comprise one or more pharmaceutically-acceptable excipients or pharmaceutically-acceptable carrier. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the embodiments are sterile compositions. Pharmaceutical compositions may be prepared using compounding techniques known or that become available to those skilled in the art.

Sterile compositions are also contemplated by the embodiments, including compositions that are in accord with national and local regulations governing such compositions.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compounds the embodiments may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions of the embodiments may be formulated for rectal administration as a suppository. For parenteral use, including intravenous, intramuscular, intraperitoneal, intranasal, or subcutaneous routes, the agents of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the pharmaceutical compositions of the embodiments may be administered using, for example, a spray formulation also containing a suitable carrier.

For topical applications, the compounds of the embodiments are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the embodiments may utilize a patch formulation to effect transdermal delivery.

The present disclosure provides a method of killing a cell, comprising administering to the cell an amount of the compound of Formulae (I)-(V) sufficient to kill the cell. In certain embodiments, the cell is a cancer cell. In certain embodiments, the cancer cell is a gastric cancer cell, pancreatic cancer cell, colorectal cancer cell, lung cancer cell or ovarian cancer cell.

In another aspect, the present disclosure provides a method of treating cancer in an individual in need thereof comprising administering to the individual an effective amount of a compound of Formulae (I)-(V). In certain embodiments, the cancer cell is a gastric cancer cell, pancreatic cancer cell, colorectal cancer cell, lung cancer cell or ovarian cancer cell.

Kits

The present disclosure provides a pharmaceutical pack or kit comprising one or more containers comprising a compound of Formulae (I)-(V) useful for the treatment or prevention of cancer. The kit can further comprise instructions for use in the treatment of cancer.

The present disclosure also provides a pharmaceutical pack or kit comprising one or more containers comprising one or more of the ingredients of the pharmaceutical compositions of the present embodiments. Optionally associated with such container(s) can be a notice in the form prescribed by a governmental agency regulating the manufacture, use or sale of pharmaceuticals or biological products, which notice reflects approval by the agency of manufacture, use or sale for human administration.

Synthesis of Drug Conjugates

The embodiments are also directed to processes and intermediates useful for preparing subject compounds or a salt or solvate or stereoisomer thereof.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I).

The conjugates of the present embodiments may be constructed by attaching the drug moiety to the antibody through a linker comprising a hydrophilic self-immolative spacer.

Representative syntheses for the linker portion of compounds of Formula (I) are described in schemes below, and the particular examples that follow.

Scheme 2

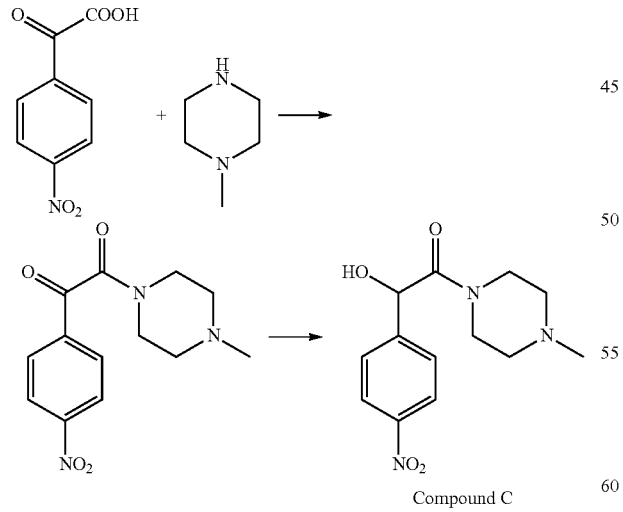

Synthesis of Compound C from 4-nitrobenzaldehyde is shown below in Scheme 2. 4-Nitrophenylglycolic acid is converted to the corresponding acid chloride using a chlorinating reagent, such as SOCl$_2$, PCl$_3$, or PCl$_5$. The acid chloride is then reacted with 1-methylpiperazine to give the ketoamide intermediate. Alternatively, the 4-nitrophenylglycolic acid can be coupled to the 1-methylpiperazine with use of coupling agent, such as EDCI. The ketoamide intermediate contains a keto group, which is then reduced with a reducing reagent, such as DIBAL-H, BH$_3$, LiAlH$_4$—AlCl$_3$, LiAlH$_4$—BF$_3$-Et$_2$O, or sodium borohydride, to produce Compound C.

Scheme 3

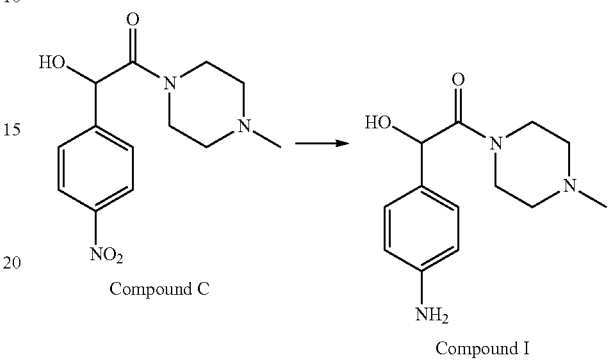

Referring to Scheme 3, the nitro group of Compound C is reduced to yield an aniline group in Compound I by catalytic hydrogenation with catalysts, such as palladium, nickel, or platinum. Examples of suitable hydrogenation catalysts include Pd/C and Raney nickel.

Scheme 4

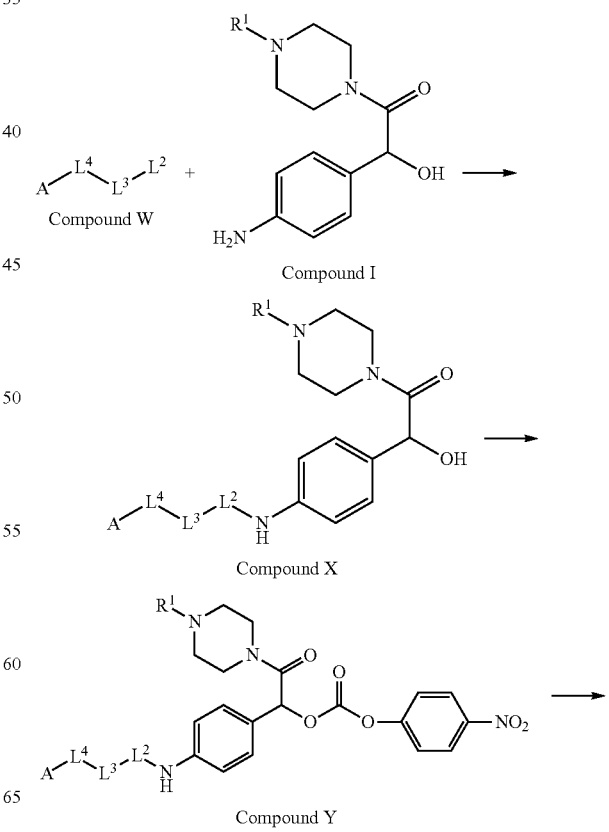

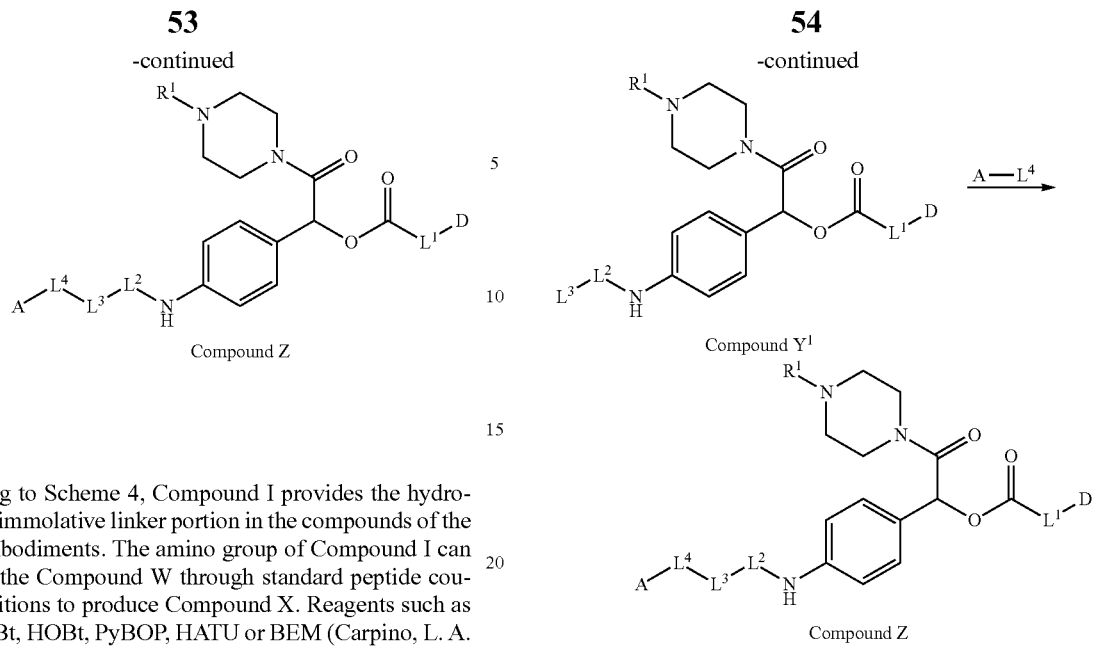

Referring to Scheme 4, Compound I provides the hydrophilic self-immolative linker portion in the compounds of the present embodiments. The amino group of Compound I can react with the Compound W through standard peptide coupling conditions to produce Compound X. Reagents such as EDCI/HOBt, HOBt, PyBOP, HATU or BEM (Carpino, L. A. J. Am. Chem. Soc. 1993, 115, 4397. Carpino, L. A.; El-Faham, A. J. Am. Chem. Soc. 1995, 117, 5401. Li, P.; Xu, J. C. J. Pept. Res. 2001, 58, 129) in the presence of a base such as DIEA or other bases familiar to one skilled in the art and in an appropriate solvent can be used.

With continued reference to Scheme 4, the hydroxyl group of Compound X is converted to an activated carbonate using 4-nitrophenyl chloroformate. With Compound Y, reaction with a drug with an amino group can produce Compound Z. If the drug does not contain an amino group, a second, intermediate self-immolative spacer or a cyclization self-elimination linker can be situated between the drug moiety and the aminobenzyloxycarbonyl group, as discussed above.

In certain embodiments, referring to Scheme 5 below, the -L³-L²- portion of the linker is attached to Compound I. Then the -A-L⁴- portion is attached.

A process for preparing the compound of the present embodiments includes preparing a solution of the antibody in a buffer and treating with a solution of reducing agent, such as TCEP. The amount of free thiols is determined. When the amount of free thiols reaches a predetermined amount, the partially reduced antibody is alkylated with the linker-drug portion.

The present disclosure provides for the process for the preparation of the compounds and intermediates in Schemes 4 and 5. The compounds represented in Schemes 4 and 5 are meant to have full valencies or properly capped with optional protecting groups or leaving groups when appropriate. For example, as shown in the scheme "Synthesis of Compound TAP-18H," L³-L² can be

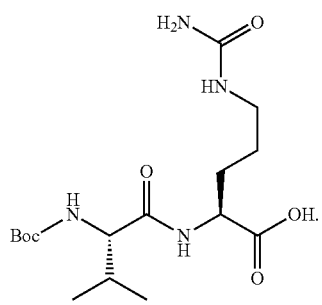 [SMILES: CC(C)[C@H](NC(=O)OC(C)(C)C)C(=O)N[C@@H](CCCNC(N)=O)C(=O)O]

The present disclosure provides for a method of preparing Compound X:

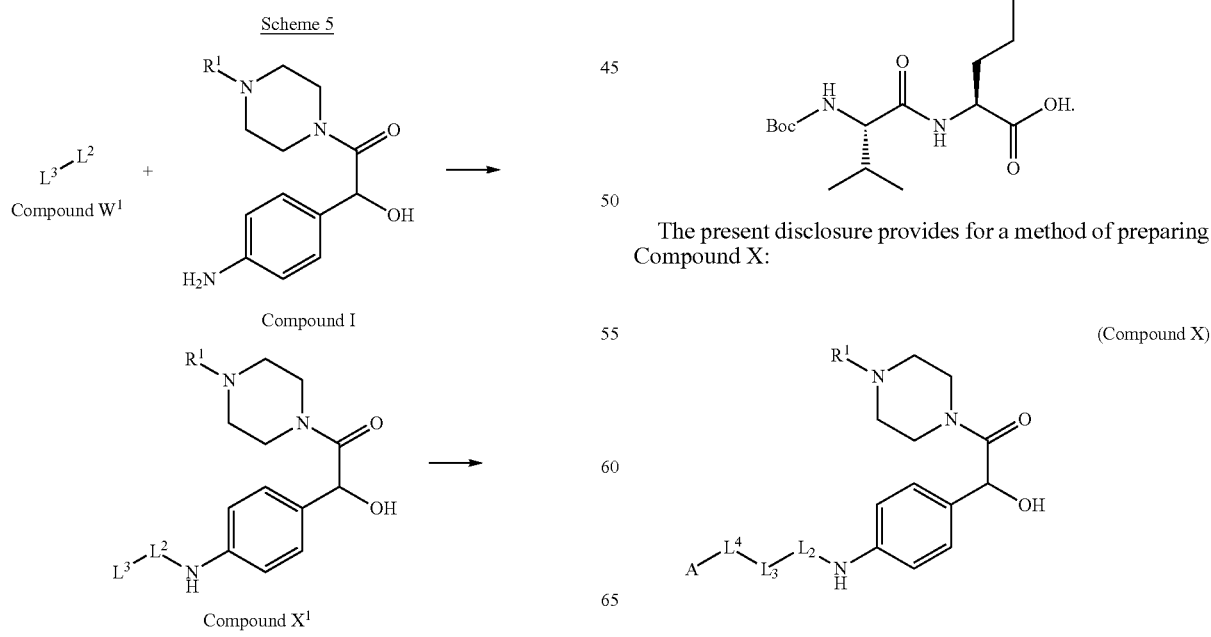

or a salt or solvate or stereoisomer thereof;

wherein:
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker;
L⁴ is bond or a spacer; and
A is an acyl unit; and
R¹ is NO₂ or NH₂;
comprising: reacting Compound W: A-L⁴-L³-L², and Compound I:

and p-nitrophenylchloroformate to form Compound Y:

reacting Compound Y with a compound comprising L¹-D.

The present disclosure provides for a method of preparing Compound X¹:

(Compound X¹)

or a salt or solvate or stereoisomer thereof;
wherein:
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker; and
R¹ is NO₂ or NH₂;
comprising: reacting Compound W': L³-L², and Compound I:

The present disclosure provides for a method of preparing Compound Z:

(Compound Z)

or a salt or solvate or stereoisomer thereof;
wherein:
D is drug moiety;
L¹ is a bond, a second self-immolative linker, or a cyclization self-elimination linker;
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker;
L⁴ is bond or a spacer; and
A is an acyl unit; and
R¹ is NO₂ or NH₂;
comprising: reacting Compound X:

The present disclosure provides for A method of preparing Compound Y¹:

(Compound Y¹)

or a salt or solvate or stereoisomer thereof;

wherein:
D is drug moiety;
L¹ is a bond, a second self-immolative linker, or a cyclization self-elimination linker;
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker; and
R¹ is NO₂ or NH₂;
comprising: reacting Compound X¹:

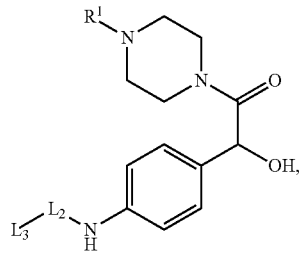

and a compound comprising L¹-D.

The present disclosure provides for a method of preparing Compound Z:

(Compound Z)

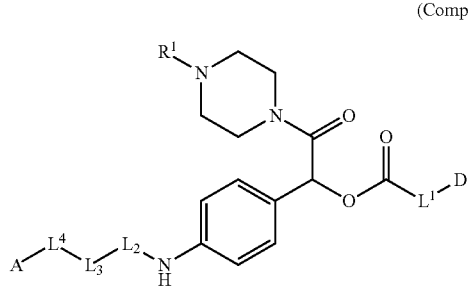

or a salt or solvate or stereoisomer thereof;
wherein:
D is drug moiety;
L¹ is a bond, a second self-immolative linker, or a cyclization self-elimination linker;
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker;
L⁴ is bond or a spacer;
A is an acyl unit; and
R¹ is NO₂ or NH₂;
comprising: reacting Compound Y¹:

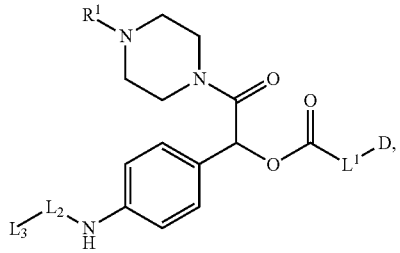

and a compound comprising A-L⁴.

The present disclosure provides for a compound of formula:

(Compound X)

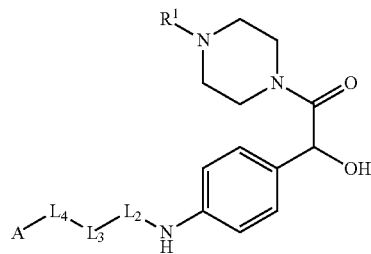

or a salt or solvate or stereoisomer thereof;
wherein:
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker;
L⁴ is bond or a spacer; and
A is an acyl unit; and
R¹ is NO₂ or NH₂.

The present disclosure provides for a compound of formula:

(Compound Z)

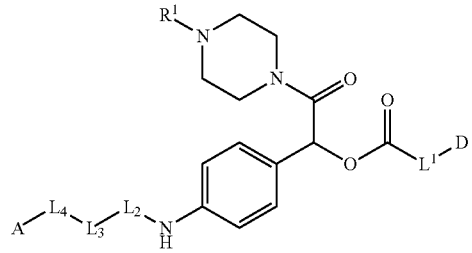

or a salt or solvate or stereoisomer thereof;
wherein:
D is drug moiety;
L¹ is a bond, a second self-immolative linker, or a cyclization self-elimination linker;
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker;
L⁴ is bond or a spacer; and
A is an acyl unit; and
R¹ is NO₂ or NH₂.

The present disclosure provides for a compound of formula:

(Compound X¹)

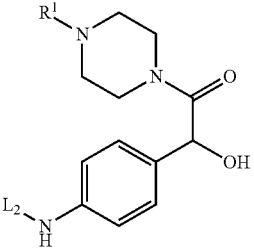

or a salt or solvate or stereoisomer thereof;

wherein:
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker; and
R¹ is NO₂ or NH₂.

The present disclosure provides for a compound of formula:

(Compound Y¹)

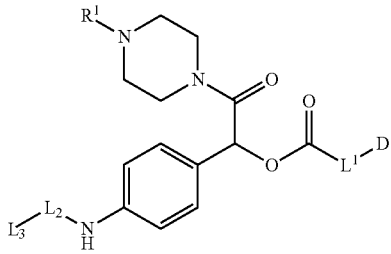

or a salt or solvate or stereoisomer thereof;
wherein:
D is drug moiety;
L¹ is a bond, a second self-immolative linker, or a cyclization self-elimination linker;
L² is a bond or a second self-immolative linker;
wherein if L¹ is a second self-immolative linker or a cyclization self-elimination linker, then L² is a bond;
wherein if L² is a second self-immolative linker, then L¹ is a bond;
L³ is a peptide linker; and
R¹ is NO₂ or NH₂.

The following examples are offered to illustrate but not to limit the invention.

Example 1

Materials and Methods

Humanization of 5F1 Antibody

Complementarity-determining region (CDR) grafting was used to generate the variable region of humanized 5F1Ca.1 (h5F1Ca.1). Briefly, the CDRs of murine 5F1 variable regions were incorporated into the framework of human variable regions (the acceptor antibodies) by recombinant DNA technology. Selection of human framework acceptors were done by BLASTP searches against the entire non-redundant Genebank database. The VH of human antibody CAA79298 (Genebank no. CAA79298), which was 67.8% identical to the murine 5F1 heavy chain variable region, and the VL of human antibody ABI74084 (Genebank no. ABI74084), which was 80.4% identical to the murine 5F1 light chain variable region, were used as the acceptor antibodies. Some residues of the acceptor antibodies were mutated to the murine counterpart residues to avoid conformation changes of the variable regions. The final amino acid sequence of h5F1Ca.1 heavy and light chain are shown in Table 1.

The VH and VL fragments were then inserted into pcDNA5-FRT-hIgG1κ vector via NheI site and AvrII site for heavy chain and light chain, respectively. The completely assembled plasmid h5F1Ca.1/pcDNA5-FRT-hIgG1, containing both the heavy chain and light chain genes of h5F1Ca.1, was used to express h5F1Ca.1 antibody.

Synthesis of Linker-Drug

Synthesis of Compound Tap-18H is shown below in the scheme. Synthesis of intermediate Compounds M and O are also shown below in the schemes.

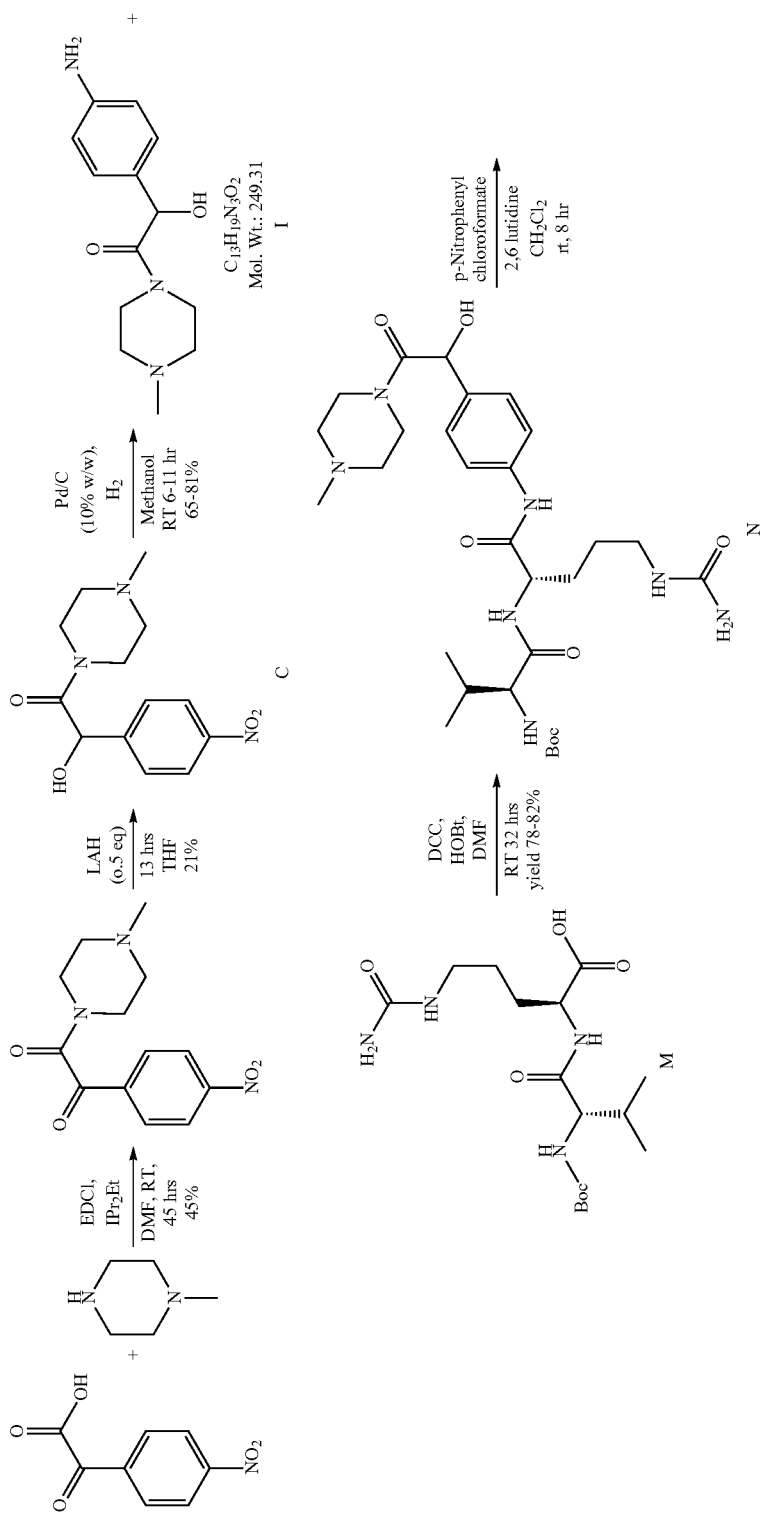

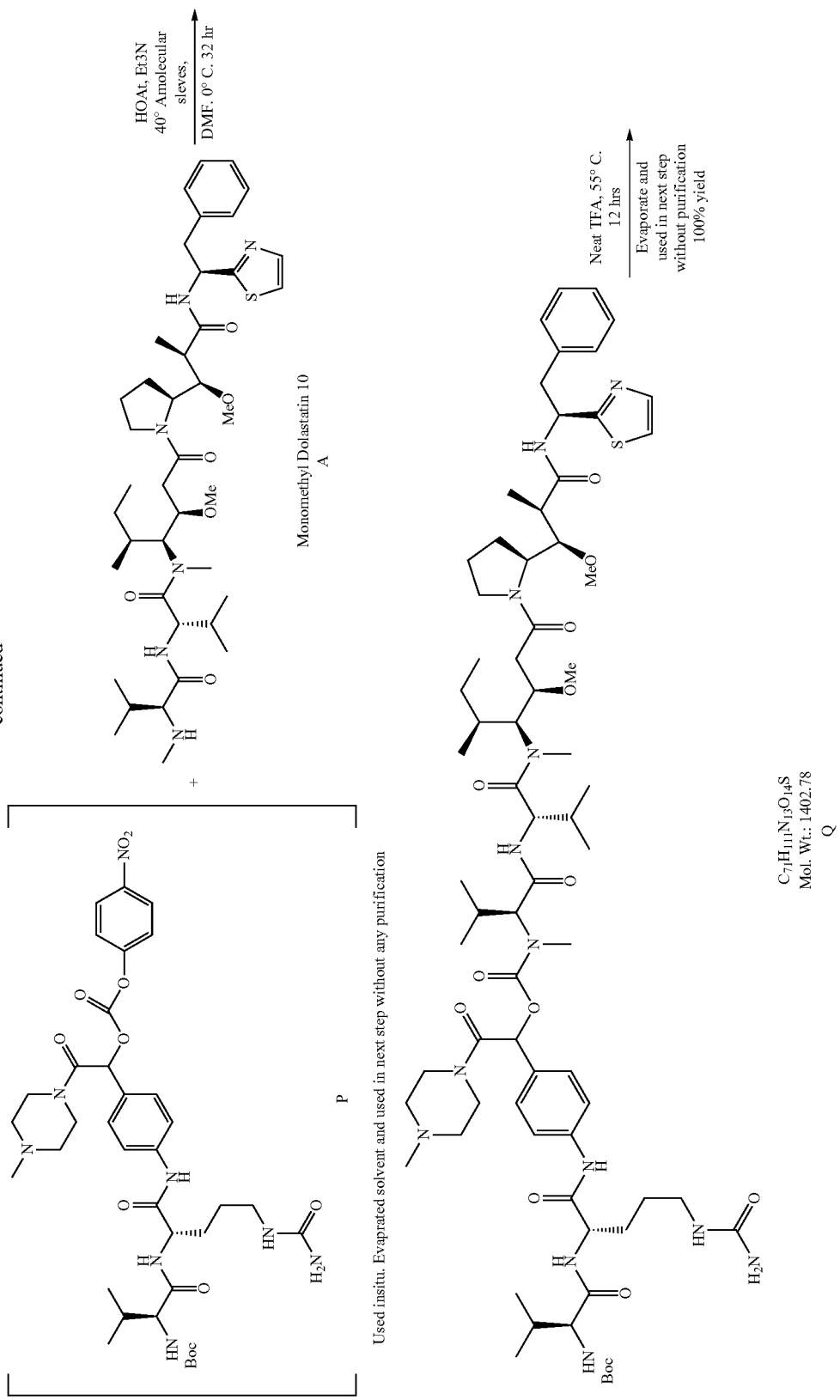

-continued
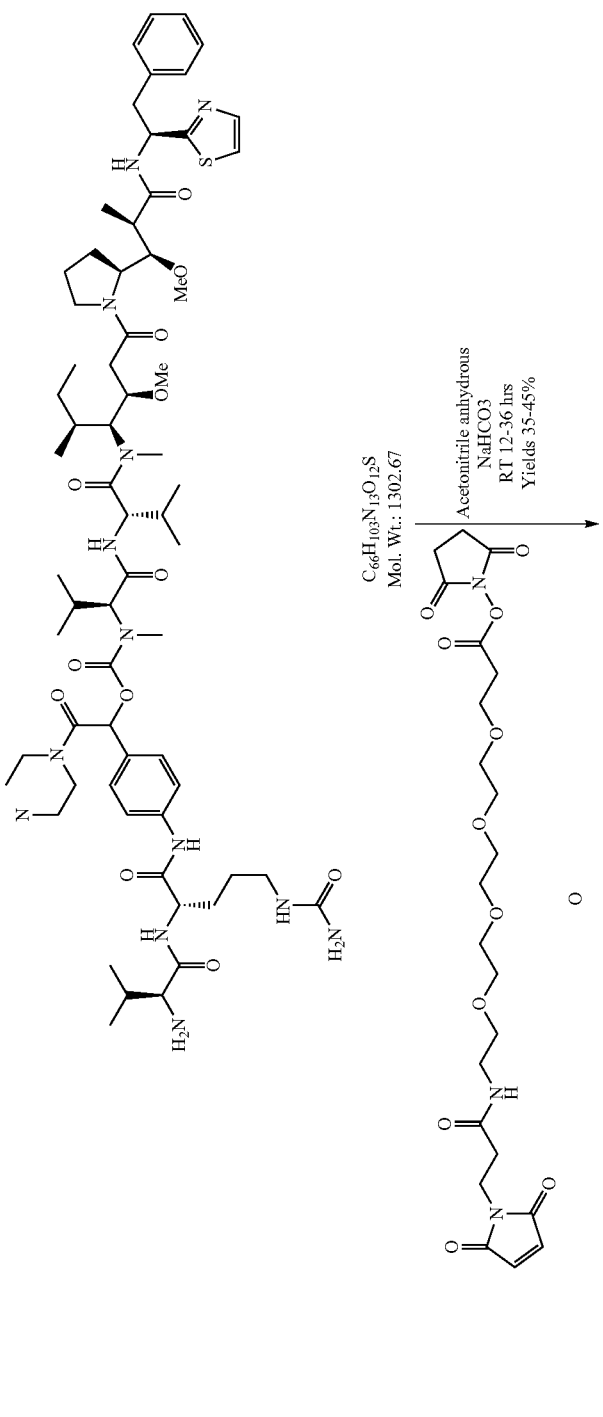
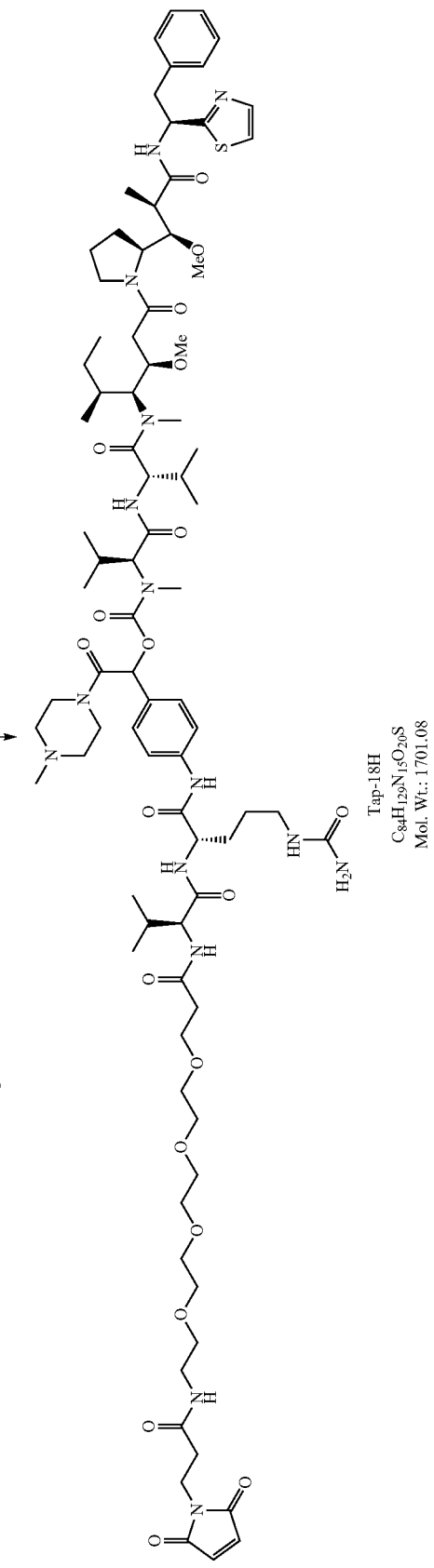

Synthesis of M
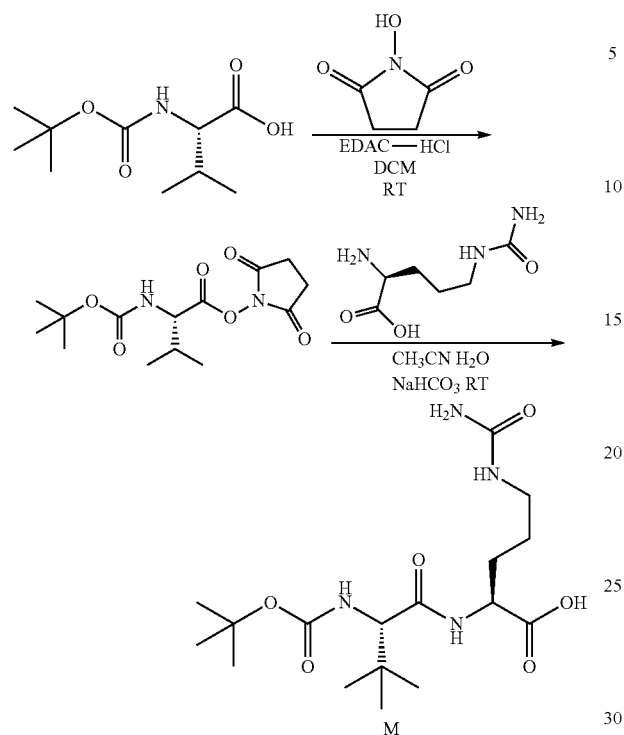
Synthesis of O

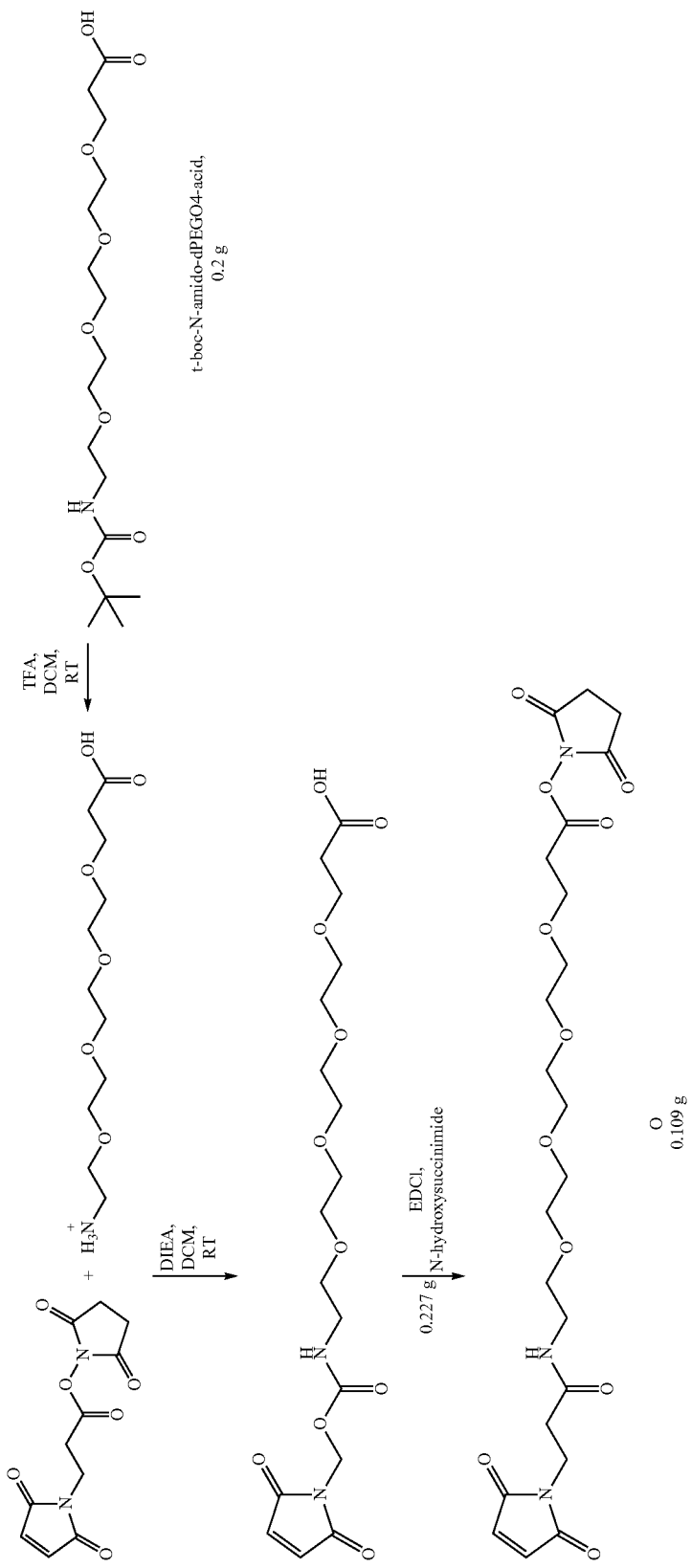

Referring to the scheme of synthesis of Compound Tap-18H, commercially available 4-nitrophenylglycolic acid was condensed with N-methylpiperazine using either PCl$_5$, or EDCI and IPr$_2$Et in DMF, or 2-chloro-4,6-dimethoxy-1,3,5-triazine in CH$_2$Cl$_2$ and N-methylmorpholine as coupling agent to produce the desired ketoamide. In a typical procedure, a solution of 2-chloro-4,6-dimethoxy-1,3,5-triazine (5 mmol) in CH$_2$Cl$_2$ (20 ml), N-methylmorpholine (15 mmol) was added at 0-5° C. under continuous stirring. A white suspension was formed after 30-40 minutes and to this mixture 4-nitrophenylglycolic acid in CH$_2$Cl$_2$ (10 ml) was added, resulting in the formation of a clear solution. After stirring the mixture for 1 hour, N-methylpiperazine (5 mmol) was added at room temperature. After completion of the reaction (TLC, 10 minutes), the mixture was washed with 10% aqueous NaHCO$_3$ solution (2×10 ml) followed by H$_2$O (3×10 ml). The organic layer was dried over anhydrous sodium sulfate and removal of the solvent under reduced pressure furnished a crude product which was further purified by recrystallization or column chromatography (pet. ether:ethyl acetate=8:2).

The ketoamide compound was further reduced by 0.5 equivalent amounts of LiAlH$_4$ in the presence of THF or DIBAL-H or sodium borohydride to produce the nitro Compound C. [B. P. Bandgar and S. S. Pandit, Tetrahedron Letters 44 (2003) 3855-3858]

Nitro Compound C was reduced to aniline Compound I by either treatment with SnCl$_2$ or catalytic hydrogenation with Pd/C (10% w/w) as catalyst in methanol at room temperature for about 6-11 hours with yield from 65-81%. It could be obtained through the following procedures using Multi-MaxIR system with an RB04-50 Reactor B. The reactor was filled initially with 35 ml of methanol, 0.03 mg of 10% Pd/C and 0.0252 mol of nitro Compound C and the hydrogen was add in the reactor up to pressure at 6.3 bar (H$_2$, const.).

Referring to the scheme of synthesis of Compound M, Boc-protected L-valine was treated with N-hydroxysuccinimide and EDAC-HCl in DCM or N-hydroxysuccinimide and EDC in DCM to give the succinimide ester. This activated ester was reacted with L-Citrulline and CH$_3$CN, H$_2$O, NaHCO$_3$ to furnish Boc-protected Compound M.

Referring to the scheme of synthesis of Compound Tap-18H, aniline Compound I was coupled with Boc-protected Compound M by means of either DCC/HOBt in DMF at room temperature for 32 hours to give Compound N (yield 78-82%), or with PS-carbodiimide, in which reaction the synthesis of Compound N was carried out starting from 100 mg of Compound M with 1.5 equivalents of aniline Compound I in the presence of two equivalents of PS-carbodiimide and 1.7 equivalents of HOBt in DCM for 24 hours. Analysis by LC/MS showed the peak with the desired mass and approximately 50-60% conversion.

The coupled product Compound N was then reacted with 4-nitrophenyl chloroformate in the presence of 2,6-lutidine in DCM at RT for 8 hours to yield carbonate Compound P, LC/MS showed the peak with the desired mass.

Treatment of carbonate Compound P with monomethyl Dolastatin 10 in the presence of HOAt and Et$_3$N in DMF resulted in the formation of Compound Q.

Referring to the scheme of synthesis of Compound O, β-alanine was treated with maleic anhydride in DMF and the acid so obtained was reacted with N-hydroxysuccinimide (NHS) under DCC coupling to give NHS-ester. The BOC protective group in commercially available t-blc-N-amido-dPEG4-acid was removed by treatment with TFA to give the TFA salt of the amine, which was reacted with previously synthesized NHS ester. The carboxylic acid so obtained was isolated and was coupled with N-hydroxysuccinimide using EDCI to furnish NHS ester Compound O.

Referring to the scheme of synthesis of Compound Tap-18H, the Boc-group in Compound Q was removed with TFA and the free amine was coupled with NHS ester Compound O in anhydrous acetonitrile and NaHCO$_3$ at room temperature for 12-36 hours to produce the final product Tap-18H with yield of 35-45%.

Figure 5:
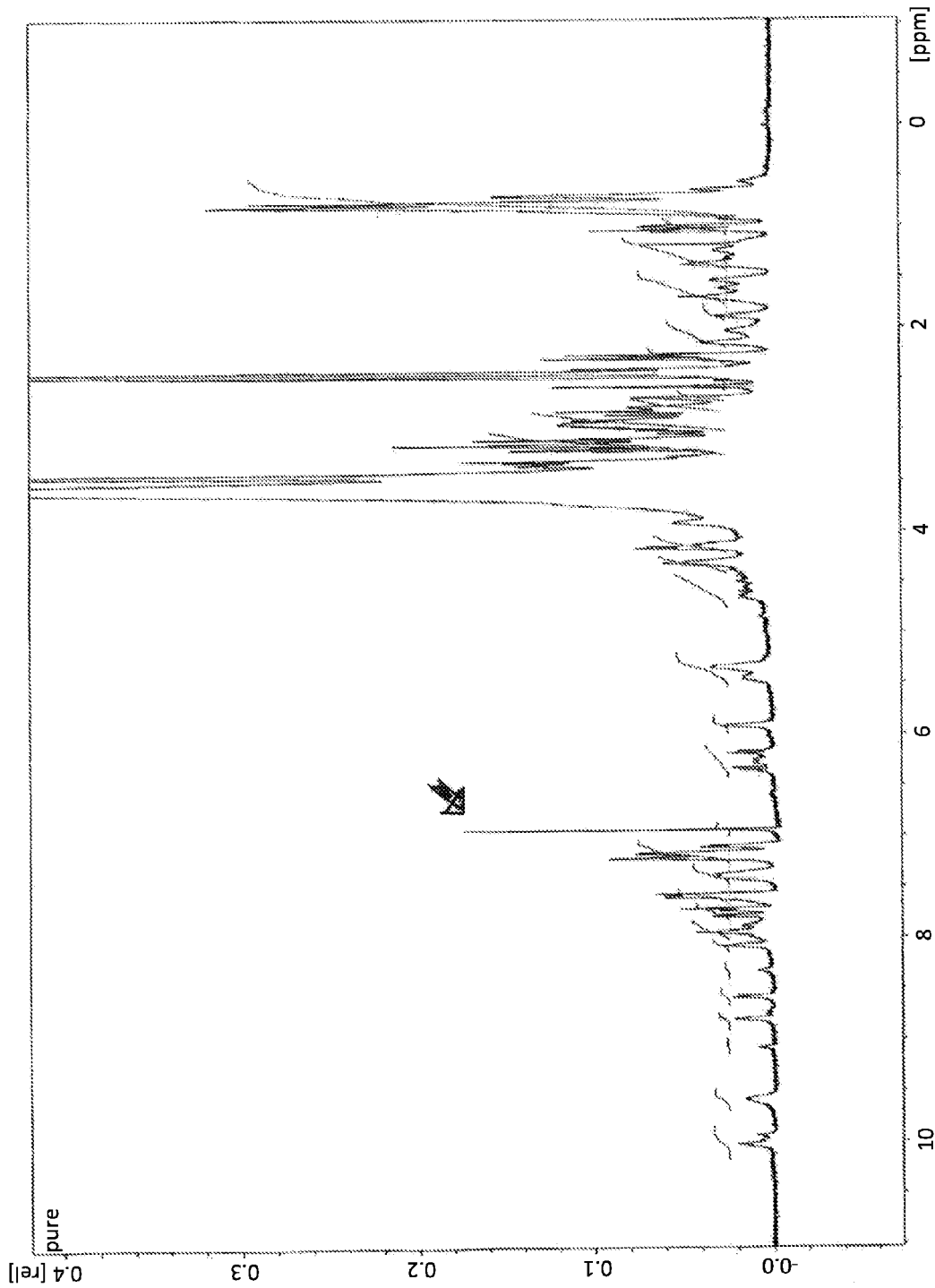
FIG. 5 shows an NMR spectrum of Tap-18H.

FIG. 5 shows an NMR spectrum of Tap-18H.

Synthesis of Compound TAP-18Hr1

Figure 6:
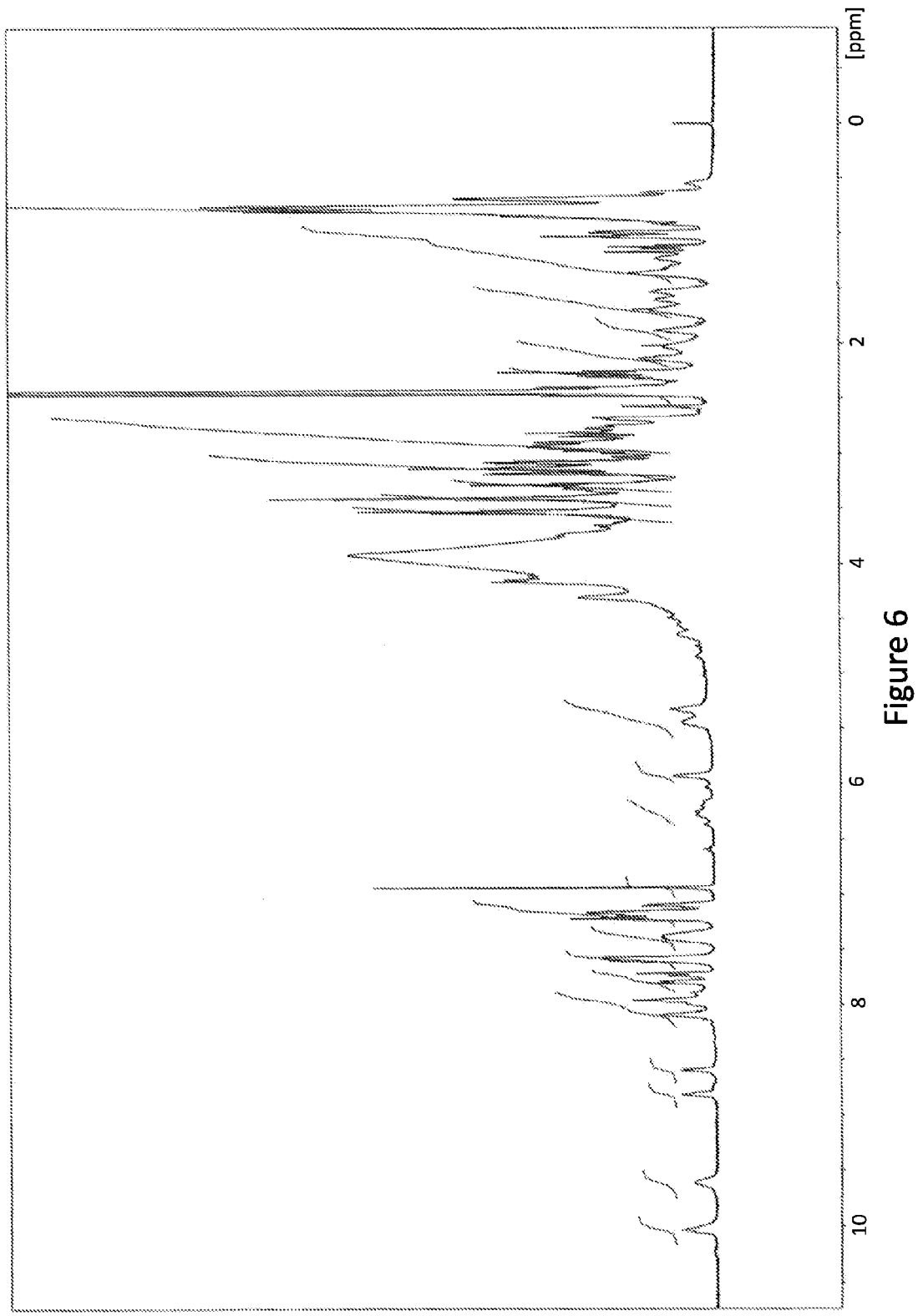
FIG. 6 shows an NMR spectrum of Tap-18Hr1.

Tap-18Hr1 was synthesized with the formula shown below. FIG. 6 shows NMR spectrum of Tap-18Hr1.

(Tap-18Hr1)

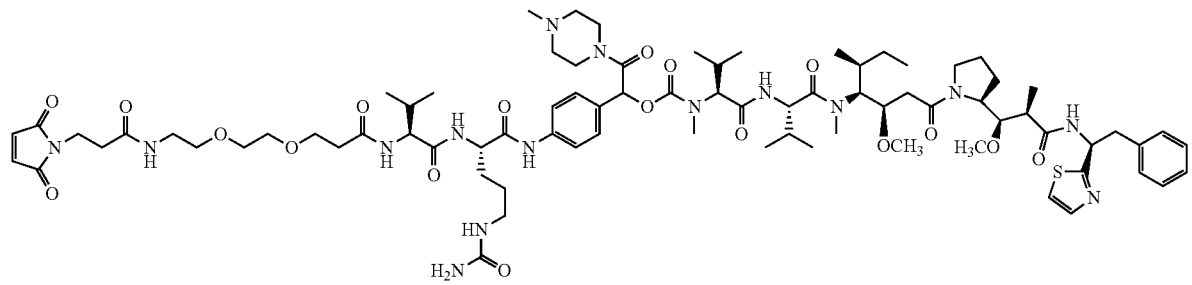

$C_{80}H_{121}N_{15}O_{18}S$
Mol. Wt.: 1612.97

Figure 7:
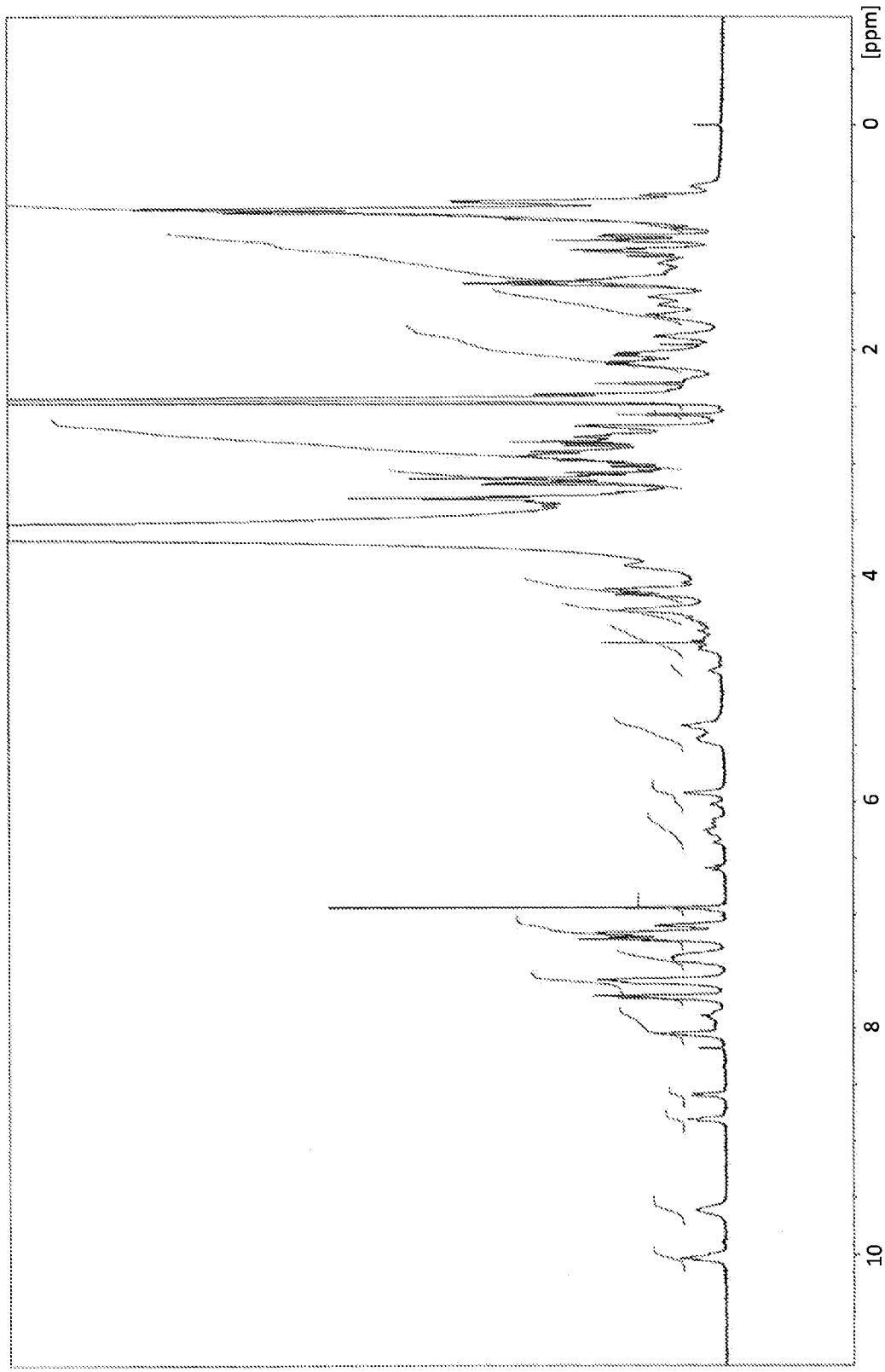
FIG. 7 shows an NMR spectrum of Tap-18Hr2.

Synthesis of Compound TAP-18Hr2
Tap-18Hr2 was synthesized with the formula shown below. FIG. 7 shows NMR spectrum of Tap-18Hr2.

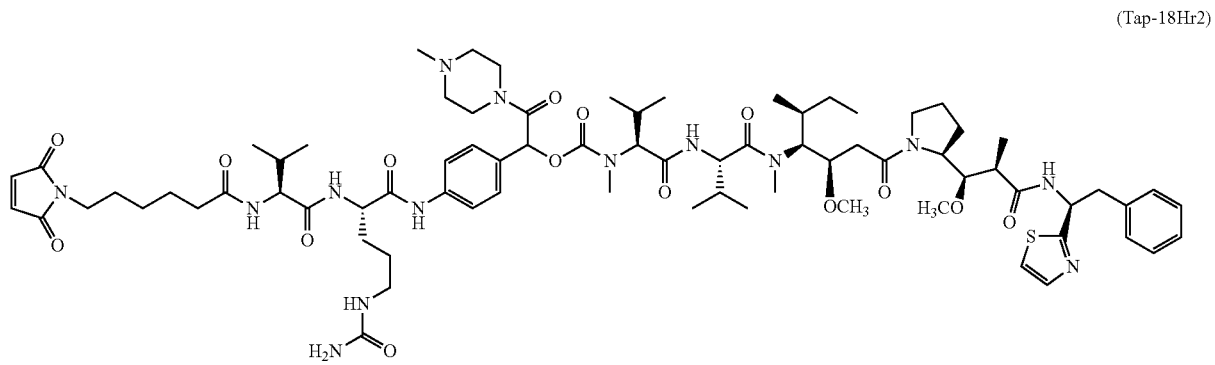 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C(=O)OC(C(=O)N1CCN(C)CC1)c1ccc(NC(=O)[C@H](CCCNC(N)=O)NC(=O)[C@@H](NC(=O)CCCCCN2C(=O)C=CC2=O)C(C)C)cc1)C(C)C]

(Tap-18Hr2)

Preparation of Antibody Drug Conjugates (ADCs)

h5F1Ca.1 was prepared by traditional method. DTT and DTPA were obtained from Sigma-Aldrich (St. Louis, Mo.). TCEP was obtained from Acros (Morris Plains, N.J.). DTNB was obtained from Thermo Scientific (Rockford, Ill.). Sodium phosphate, sodium borate, and sodium chloride were obtained from J. T. Baker (Center Valley, Pa.). Cysteine was obtained from Alfa Aesar (Ward Hill, Mass.).

h5F1Ca.1 was reduced with about 1.3 equivalents of TCEP in 0.025 M sodium borate pH 8, 0.025 M NaCl, 1 mM DTPA for 2 hours at 37° C. The protein concentration was quantified using an absorbance value of 1.42 at 280 nm for a 1.0 mg/mL solution, and the molar concentration determined using a molecular weight of 150,000 g/mol. The concentration of mAb-cysteine thiols produced was determined by titrating with DTNB. Typically resulting in about 2.0 to 2.5 thiols/mAb when 1.3 molar equivalents of TCEP were used.

Partially reduced h5F1Ca.1 was alkylated with 1.2 molar of maleimidocaproyl-drugs/mAb-cysteine thiol or maleimido-drugs/mAb-cysteine thiol. The alkylation reaction was performed at 10° C. for 60 minutes. Cysteine (1 mM final) was used to quench any unreacted, excess maleimidocaproyl-drugs or maleimido-drugs. The ADCs were first adjusted to pH 5 with 1 M acetic acid and applied to a HiTrap™ SP FF column (GE Healthcare) at a flow rate of 1 mL/min. The column size was 1 mL per 10 mg of ADC. The column was previously equilibrated with 5 column volumes of binding buffer, 25 mM sodium acetate with 15% DMSO pH 5. Following application, the column was washed with 10 column volume of binding buffer and then eluted with elution buffer, 25 mM sodium acetate pH 5, 0-15% DMSO, 300 mM NaCl. The purified ADCs were changed to phosphate buffered saline by dialysis overnight at 4° C.

Cell Lines

The gastric cancer cells SNU-16 (BCRC, Cat. No. 60212), the colorectal cancer cells COLO 205 (ATCC, Cat. No. CCL-222), DLD-1 (ATCC, Cat. No. CCL-221) and SW480 (ATCC, Cat. No. CCL-228) were cultured in RPMI Medium 1640 (GIBCO, Cat. No. 22400) supplemented with 10% FBS (GIBCO, Cat. No. 26140) and 100 U/mL penicillin/100 µg/mL streptomycin (GIBCO, Cat. No. 15140).

The colorectal cancer cell line DLD-1 (BCRC, Cat. No. 60132) was cultured in RPMI Medium 1640 supplemented with 10% FBS, 1 mM sodium pyruvate (GIBCO, Cat. No. 11360), and 100 U/mL penicillin/100 µg/mL streptomycin.

The pancreatic cancer cell line PANC-1 (BCRC, Cat. No. 60284) was cultured in Dulbecco's modified Eagle's medium (GIBCO, Cat. No. 11965) supplemented with 10% FBS and 100 U/mL penicillin/100 µg/mL streptomycin.

The pancreatic cancer cells Panc 02.03B were adapted from Panc 02.03 (ATCC, Cat. No. CRL-2553), and cultured without insulin in RPMI Medium 1640 supplemented with 15% FBS, 100 U/mL penicillin/100 µg/mL streptomycin and 1 mM sodium pyruvate (GIBCO, Cat. No. 11360).

Analysis of ADCs by Reversed-Phase HPLC

ADCs were analyzed under denaturing and reducing conditions by heating with 25 mM DTT, 3M guanidine hydrochloride at 80° C. for 10 minutes. The 50 µg denatured ADCs were applied to PLRP-S column (2.1×150 mm, 8 µm, 1000 Å, Aligent (Santa Clara, Calif.)). The flow rate was 0.8 mL/min and the column temperature was 80° C. Solvent A was 0.05% trifluoroacetic acid in water and solvent B was 0.04% trifluoroacetic acid in acetonitrile. The method included the following: Isocratic 25% B for 3 minutes; a 25-minute linear gradient to 50% B; a 2-minute linear gradient to 95% B; a 1-minute linear gradient to 25% B; and isocratic 25% B for 2 minutes. Peak assignments were made with unconjugated h5F1Ca.1 (L0 and H0). L1, H1, H2, and H3 were assigned by their elution time, UV spectra (the A248/280 ratio increases with drug loading), and SDS-PAGE profile (light chain and heavy chain).

In-Vitro Cytotoxicity by WST-1 Assay

Cancer cells SNU-16, Panc 02.03B, COLO 205 and SW480 were seeded $1\times10^4$, $3\times10^3$, $2\times10^4$ and $1.2\times10^4$ cells/well, respectively, on 96-well microtiter plates. Cancer cells DLD-1 and PANC-1 were seeded $1\times10^4$ cells/well on 96-well microtiter plates. h5F1Ca.1/Tap18H ADC, h5F1Ca.1/Tap18Hr1 or naked antibody h5F1Ca.1 were added in triplicate at final concentration of 3 μg/mL and 1 μg/mL or final indicated concentrations and a final volume 200 μL/well. Cells were then incubated at 37° C. and 5% $CO_2$, and cell viability was detected at 72 hours or 96 hours by cell proliferation reagent WST-1 (Roche (Nutley, N.J.), Cat. No. 11644807001) following manufacturer's instructions. In brief, at the end of incubation 100 μL of medium was withdrawn and 10 μL/well of WST-1 was added to the tested cell line. After optimal color development (when $OD_{450}$ of untreated control ≥1.00), absorbance at 450 nm ($OD_{450}$ value) was measured by spectrophotometer (Molecular Devices (Sunnyvale, Calif.), VERSAmax microplate reader). The mean of the triplicates was obtained and background (medium control) was subtracted. The resultant $OD_{450}$ values were then used to calculate % inhibition according to the following formula: $[OD_{450}$ solvent$-OD_{450}$ sample$]/[OD_{450}$ solvent$]*100$.

ADC Treatment in Cancer Xenograft Model

To establish a subcutaneous xenograft model, $5 \times 10^6$ SNU-16 cells were implanted into the right flank of C.B-17 SCID mice (Lasco, Taipei, Taiwan). The ADC treatment initiated when average tumor volume reached 110-120 $mm^3$ (marked as Day 1). h5F1Ca.1/Tap18H or h5F1Ca.1/Tap18Hr1 was injected intravenously at 1 or 2 mg/kg in 100 μL. Tumor volume was measured twice weekly with a caliper in two perpendicular dimensions, and calculated according to the formula (0.52*length*width*width).

Results

Analysis of ADCs by Reversed-Phase HPLC

Reducing and denaturing reversed-phase HPLC was used to separate and characterize light and heavy chains with different drugs. In this method, pretreatment of the ADC with 3M guanidine hydrochloride and excess of DTT at 80° C. denature antibody and break the interchain and intrachain disulfides allow separation of light chain with 0 or 1 drugs (L0 and L1) and heavy chain with 0, 1, 2, 3 drugs (H0, H1, H2, H3) (FIG. 1). In general, the dolastatin-10 is more hydrophobic than MMAE. However, the data shows that heavy and light chain with dolastatin-10 drug eluted earlier than monomethyl auristatin E (MMAE) drug in L1, H1, H2, and H3 peaks. This shows that the extra piperazine group in the dolastatin-10 based drug reduces the hydrophobicity of molecule. This characteristic of the piperazine group may reduce the possible aggregation in high drug loading ADC cause by the hydrophobicity of dolastation-10.

FIG. 1 shows the reversed-phase HPLC characterization of ADCs. FIG. 1(A) shows the chromatogram for h5F1Ca.1/Tap-18H. FIG. 1(B) shows the chromatogram for h5F1Ca.1/MMAE. Light chain with 0 or 1 drugs (L0 and L1) and heavy chain with 0, 1, 2, 3 drugs (H0, H1, H2, H3) are shown.

In Vitro Cytotoxicity

The in vitro cytotoxic activity of the h5F1Ca.1/Tap18H was evaluated in the h5F1Ca.1 antigen positive cancer cell lines (SNU-16, COLO 205 and Panc02.03B) and antigen negative cell line (SW480). Cytotoxicity by the naked h5F1Ca.1 antibody was also tested in parallel. As shown in Table 3, while h5F1Ca.1 alone was not able to induce cytotoxicity at tested concentrations (3 and 1 μg/mL), h5F1Ca.1/Tap18H effectively inhibited the growth of cancer cell lines, SNU-16, COLO 205 and Panc02.03B. No toxicity was observed in the antigen negative cell line SW480, indicating ADC killing was via a specific targeting mechanism. These results demonstrate that the ADC delivered cytotoxic drug to the target cancer cells with antigen specificity.

TABLE 3

In vitro cytotoxic activity by h5F1Ca.1/Tap18H

| (% inhibition) | | 3 μg/mL | 1 μg/mL |
|---|---|---|---|
| SNU-16 | h5F1Ca.1/Tap18H | 95.7 | 90.6 |
| | h5F1Ca.1 | −13.7 | −0.1 |
| COLO 205 | h5F1Ca.1/Tap18H | 90.1 | 82.4 |
| | h5F1Ca.1 | −11.0 | −7.2 |
| Panc 02.03B | h5F1Ca.1/Tap18H | 81.0 | 78.4 |
| | h5F1Ca.1 | −12.5 | −6.4 |
| SW480 | h5F1Ca.1/Tap18H | −20.9 | −12.4 |
| | h5F1Ca.1 | −9.2 | −3.8 |

Note:
Negative values indicate no inhibition observed in the tested wells.

The cytotoxic activity of the h5F1Ca.1/Tap18Hr1 was also evaluated in a separate experiment. Similarly, effective inhibition was induced by h5F1Ca.1/Tap18Hr1 in binding-positive gastric cancer cell line SNU-16, but not in the binding-negative colorectal cell line SW480 (Table 4).

TABLE 4

In vitro cytotoxic activity by h5F1Ca.1/Tap18Hr1

| (% inhibition) | | 3 μg/mL | 1 μg/mL |
|---|---|---|---|
| SNU-16 | h5F1Ca.1/Tap18Hr1 | 98.2 | 97.0 |
| | h5F1Ca.1 | 4.0 | 3.3 |
| SW480 | h5F1Ca.1/Tap18Hr1 | 5.4 | 1.9 |
| | h5F1Ca.1 | −3.0 | 1.2 |

Note:
Inhibition below 10% is considered background value of the assay. Negative values indicate no inhibition observed in the tested wells.

In Vivo Evaluation of ADC

Figure 2:
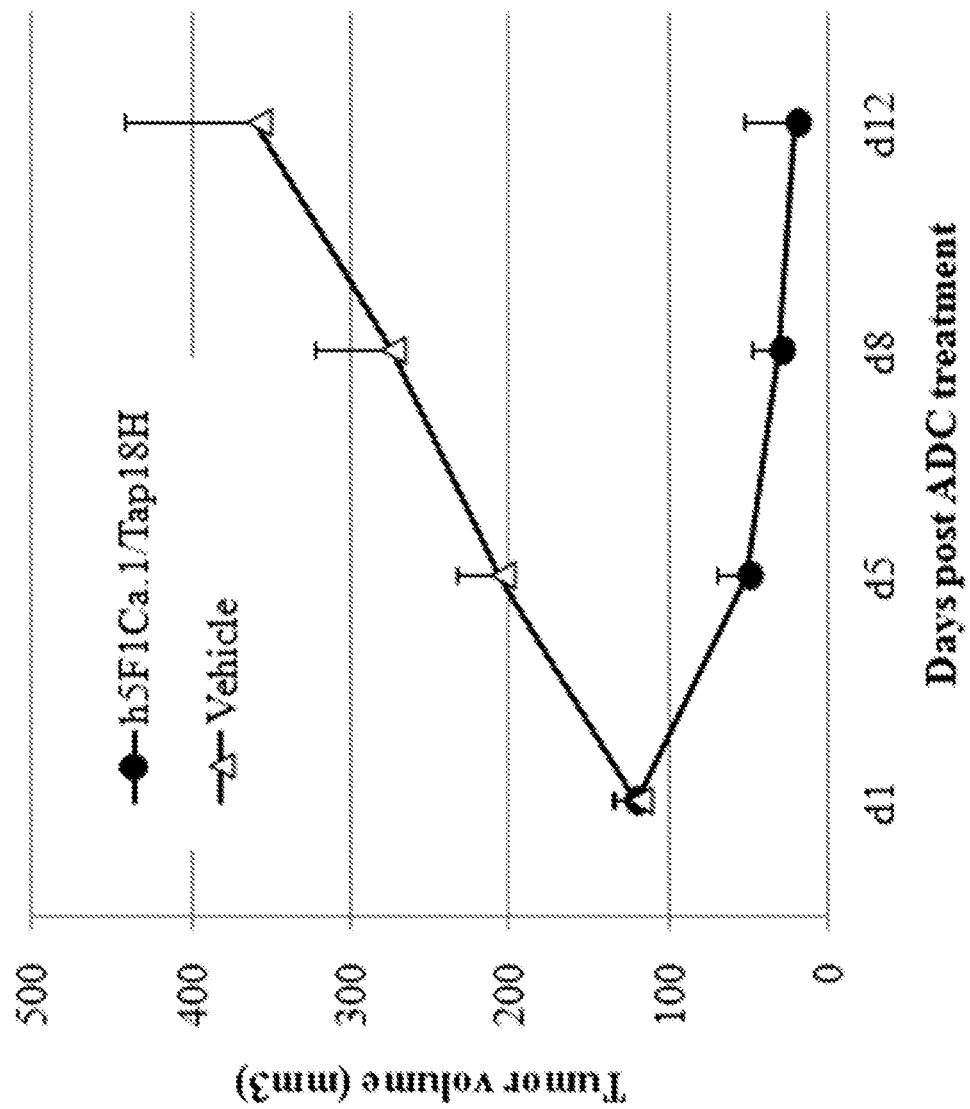
FIG. 2 shows in vivo anti-tumor activity by h5F1Ca.1/Tap18H against gastric cancer SNU-16.

Potency of ADC h5F1Ca.1/Tap18H was evaluated in vivo against the gastric cancer cells SNU-16. When inoculated tumor size reached 120 $mm^3$ (marked as Day 1), mice were treated with a single dose of ADC or vehicle at 2 mg/kg. Compared to the vehicle group in which tumor rapidly grew and approached 400 $mm^3$ at day 12, h5F1Ca.1/Tap18H group displayed remission at Day 5, and mean tumor sizes were further suppressed down to <20 $mm^3$ at day 12 (FIG. 2). Body weight of these mice remained unchanged in both treatment and vehicle groups. Therefore, the data show that h5F1Ca.1/Tap18H can effectively inhibit growth of antigen positive tumor in SCID mice.

FIG. 2 shows a graph of in vivo anti-tumor activity by h5F1Ca.1/Tap18H against gastric cancer SNU-16.

Figure 3:
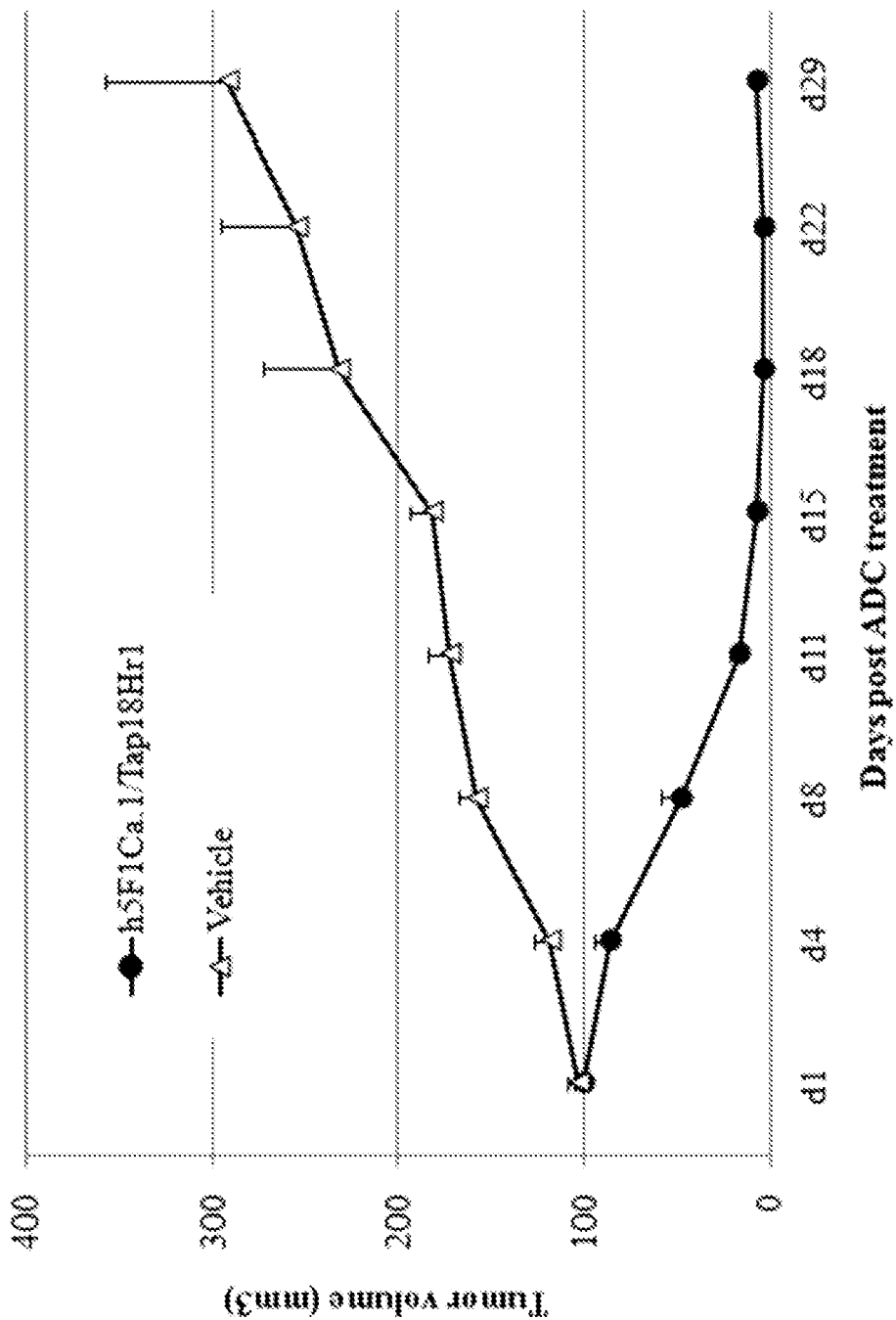
FIG. 3 shows in vivo anti-tumor activity of h5F1Ca.1-conjugated ADC against gastric cellos SNU-16.

Potency of ADC h5F1Ca.1/Tap18Hr1 was evaluated in vivo against the gastric cancer cells SNU-16. When inoculated tumor size reached 100 $mm^3$ (marked as day 1), mice were treated with 2 weekly doses of vehicle or ADC at 1 mg/kg. As shown in FIG. 3, administration of h5F1Ca.1/Tap18Hr1 caused tumor regression, in which mean tumor size was suppressed down to <10 $mm^3$. Body weight of these mice remained unchanged in both treatment and vehicle groups. Therefore, our data show that h5F1Ca.1/Tap18Hr1 can effectively inhibit growth of antigen-positive tumor in SCID mice.

Example 2

Effects of Anti-TfR Antibody Based Antibody Drug Conjugate (ADC) in Inhibiting Tumor Growth Preparation of Antibody Drug Conjugates (ADCs)

Chimeric 5D7-54.17 (c5D7) was produced from Flp-In CHO cells transfected with expression vector, pcDNA5-FRThIgG1, containing the heavy and light chain variable region genes of murine 5D7-54.17. The c5D7 antibody was then conjugated to the cytotoxic drug monomethyl dolastatin 10 to evaluate its anti-tumor effect in vivo via a piperazin containing linker (see Table 5 for structure). In one example, purified c5D7 was firstly reduced with 3.0 equivalents of TCEP (or tris(2-carboxyethyl)phosphine) in 0.025 M sodium borate pH 8, 0.025 M NaCl, 1 mM DTPA (or Pentetic acid or diethylene triamine pentaacetic acid) for 2 h at 37° C. The protein concentration was quantified using an absorbance value of 1.346 at 280 nm for a 1.0 mg/mL solution, and the molar concentration determined using a molecular weight of 145,194 g/mol. The concentration of mAb-cysteine thiols produced was determined by titrating with DTNB (or 5,5'-dithiobis-(2-nitrobenzoic acid)). Typically 4.0 to 4.5 thiols/mAb was produced when 3.0 molar equivalents of TCEP were used. Partially reduced c5D7 was alkylated with 2.4 molar of maleimidocaproyl-monomethyl dolastatin 10/mAb-cysteine thiol. The alkylation reaction was performed at 10° C. for 30 min. Cysteine (1 mM final) was used to quench any unreacted, excess maleimidocaproyl-monomethyl dolastatin 10 drug. The resultant ADCs were changed to phosphate buffered saline by dialysis overnight at 4° C.

Tap-18Hr1 was synthesized with the formula shown below. FIG. 5 shows NMR spectrum of Tap-18Hr1.

TABLE 6-continued

| In vitro cytotoxic activity by c5D7/Tap18Hr1 | | | |
|---|---|---|---|
| (% inhibition) | | 0.3 µg/mL | 0.1 µg/mL |
| PANC-1 | c5D7/Tap18Hr1 | 1.4 | 2.9 |
| | c5D7 | 4.5 | 4.6 |

Note:
Inhibition below 10% is considered background value of the assay. Negative values indicate no inhibition observed in the tested wells.

ADC Treatment in Cancer Xenograft Model

To establish a subcutaneous xenograft model, $5 \times 10^6$ DLD-1 colorectal cancer cells were implanted into the right flank of C.B-17 SCID mice (Lasco, Taipei, Taiwan). Drug-conjugated c5D7 ADC was administered intravenously at 3 mg/kg at days 1 and 5 post tumor inoculation. Tumor volume was measured twice weekly with a caliper in two perpendicular dimensions, and calculated according to the formula $(0.52 \times length \times width \times width)$.

Results

The chimeric 5D7-54.17 antibody (c5D7) was used in preparing an antibody drug conjugate (ADC), c5D7/Tap18Hr1 (see above for the methods of making the ADC). The anti-tumor activity of c5D7/Tap18Hr1 was evaluated in vivo on DLD-1 transplanted SCID mice. Treatment was initiated at

TABLE 5

The Linker-Drug portion of the Antibody-Drug conjugate.

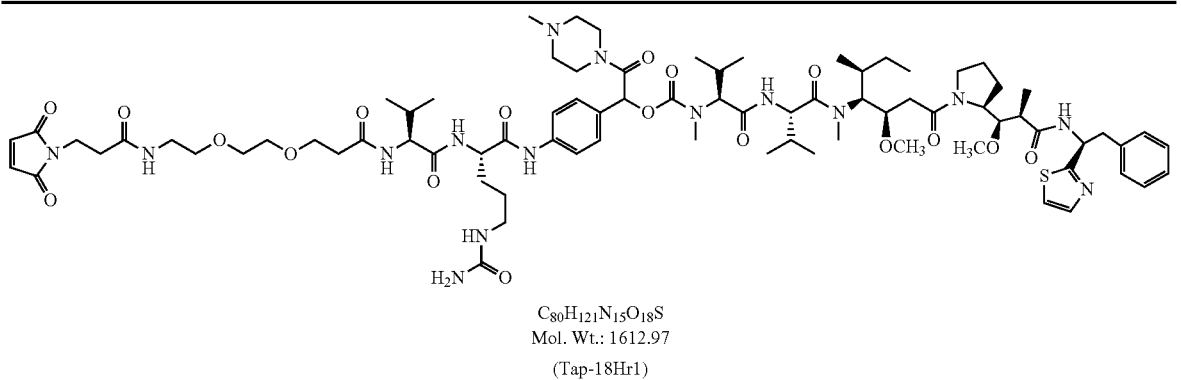

$C_{80}H_{121}N_{15}O_{18}S$
Mol. Wt.: 1612.97

(Tap-18Hr1)

We further examined the in vitro cytotoxic activity of the c5D7/Tap18Hr1 in the binding-positive colorectal cancer cell line DLD-1, and binding-negative pancreatic cell line PANC-1. Consistent with data presented above, effective growth inhibition in DLD-1 cells was induced by c5D7/Tap18Hr1 but not by c5D7 antibody alone (Table 6). Nor inhibition was observed in the binding-negative cell line PANC-1 at the indicated doses. Taken together, these results demonstrate that our ADC delivered cytotoxic drug only to the target cancer cells expressing the specific antigen.

TABLE 6

Figure 4:
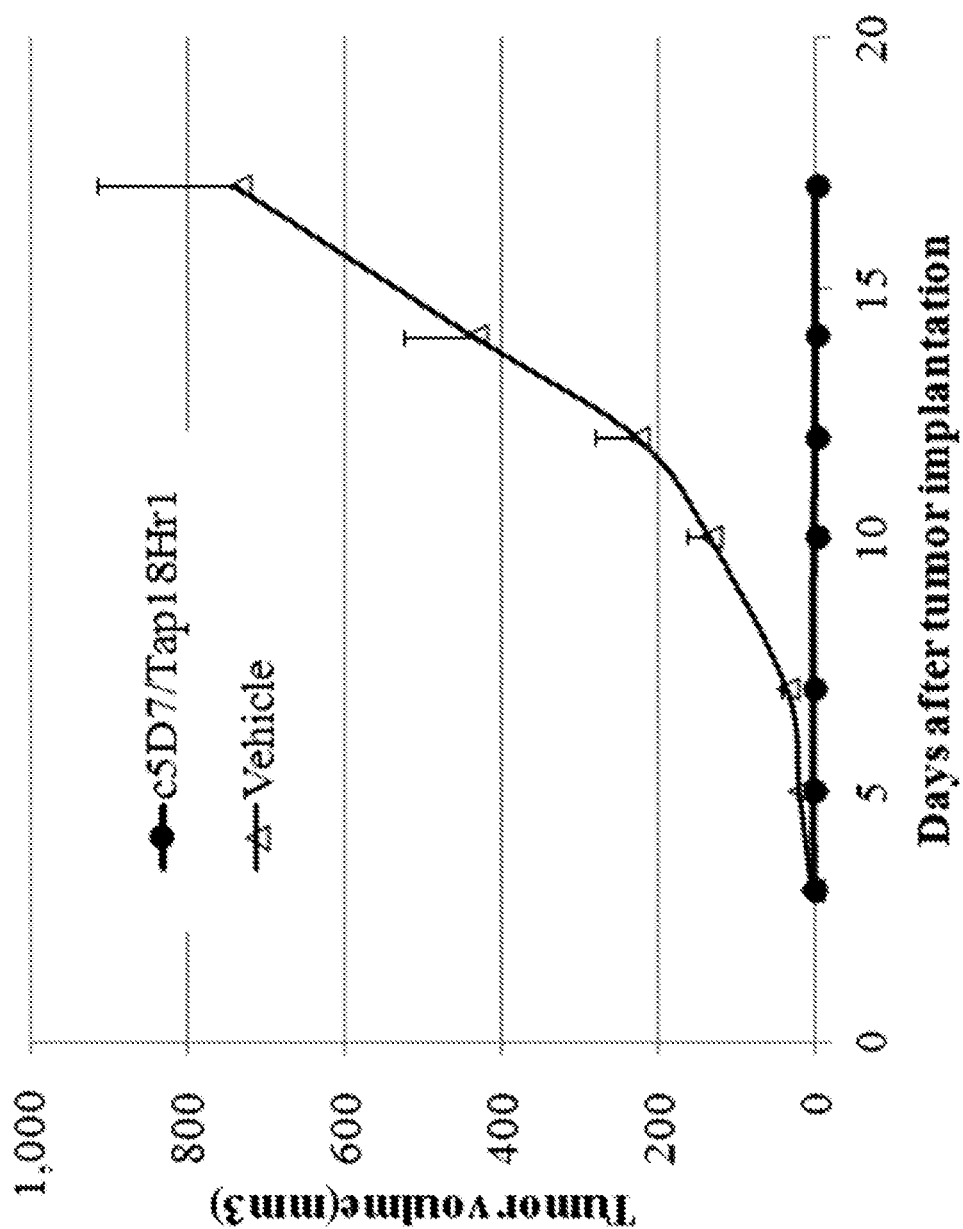
FIG. 4 shows in vivo anti-tumor activity of c5D7-conjugated ADC against colorectal cancer DLD-1.

| In vitro cytotoxic activity by c5D7/Tap18Hr1 | | | |
|---|---|---|---|
| (% inhibition) | | 0.3 µg/mL | 0.1 µg/mL |
| DLD-1 | c5D7/Tap18Hr1 | 62.0 | 35.4 |
| | c5D7 | -0.3 | 0.6 | days 1 and 5 following tumor inoculation with vehicle or ADC at 3 mg/kg. Compared to the vehicle group in which tumor approached 500 mm³ at day 14, c5D7/Tap18Hr1 completely suppressed tumor growth throughout the study period (FIG. 4). Body weight of mice from either group remained unchanged after treatment (25 g on average). The data shows that cancer targeting delivery of cytotoxic drug by the anti-transferrin receptor c5D7 was able to effectively inhibit tumor growth in vivo.

REFERENCES

1. Carter, P J and Senter, P D. Antibody-drug conjugates for cancer therapy. Cancer J. 2008; 14: 154-169)
2. Teicher, B A. Antibody-drug conjugate targets. Current cancer Drug Targets 2009, 9: 982-1004.
3. Ducry, L and Stump, B. Antibody-drug conjugates: linking cytotoxic payloads to monoclonal antibodies. Bioconjugate chem., 2010, 21: 5-13.
4. Koblinski, J E., Ahram, M and Sloane, B F. Unraveling the role of proteases in cancer. Clin. Chem. Acta 2000; 291: 113-135.

What is claimed is:

1. A compound of the formula (I):

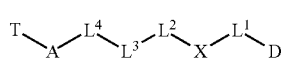

(I)

or a salt or solvate or stereoisomer thereof;
wherein:
T is a targeting moiety selected from the group consisting of: (a) an antibody comprising a heavy chain variable region comprising three CDRs from SEQ ID NO: 1 and a light chain variable region comprising three CDRs from SEQ ID NO: 2; and (b) an antibody comprising a heavy chain variable region comprising three CDRs from SEQ ID NO: 3 and a light chain variable region comprising three CDRs from SEQ ID NO: 4; and -A-L$^4$-L$^3$-L$^2$-X-L$^1$-D is selected from the group consisting of:

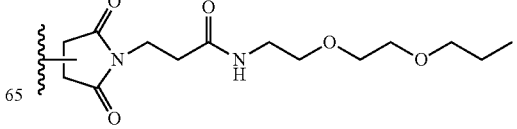

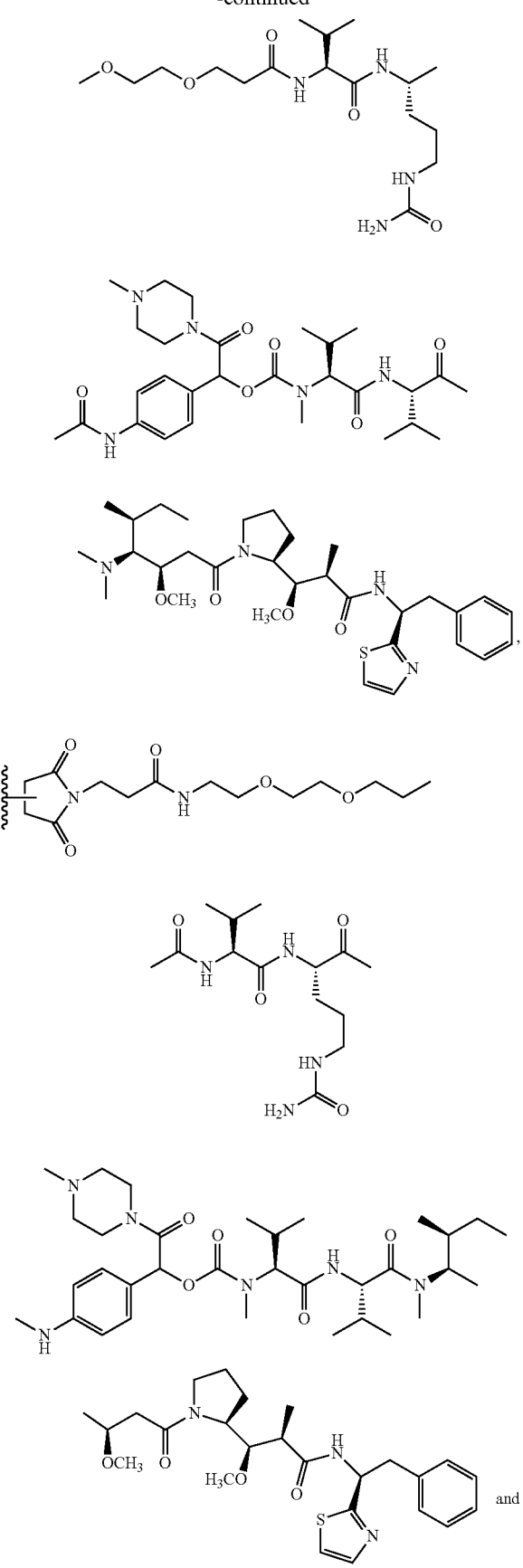

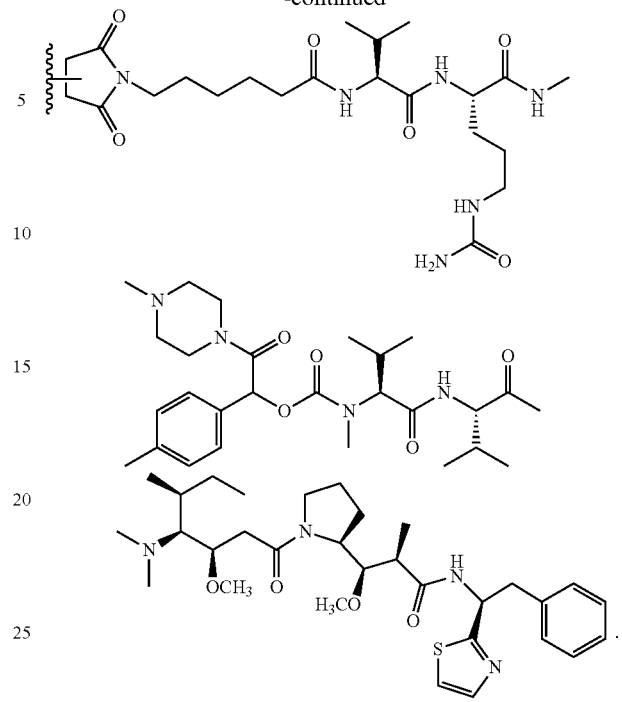

, and

2. The compound of claim 1, wherein T is an antibody comprising a heavy chain variable region comprising amino acids 1-118 of SEQ ID NO: 1 and/or a light chain variable region comprising amino acids 1-113 of SEQ ID NO: 2.

3. The compound of claim 1, wherein T is an antibody comprising a heavy chain variable region comprising amino acids 1-119 of SEQ ID NO: 3 and/or a light chain variable region comprising amino acids 1-108 of SEQ ID NO: 4.

4. A pharmaceutical composition comprising a compound of claim 1, or a salt or solvate or stereoisomer thereof; and a pharmaceutically acceptable carrier.

5. A method of killing a cell, comprising administering to the cell an amount of the compound of claim 1, or a salt or solvate or stereoisomer thereof, sufficient to kill the cell.

6. The method of claim 5, wherein the cell is a cancer cell selected from a gastric cancer cell, pancreatic cancer cell, colorectal cancer cell, lung cancer cell, esophageal cancer cell, gallbladder cancer cell, head and neck cancer cell, liver cancer cell, endometrial carcinoma cell, salivary gland carcinoma cell, lymphoma cell, breast cancer cell, cervical cancer cell and ovarian cancer cell.

7. A method of treating cancer in an individual in need thereof comprising administering to the individual an effective amount of a compound of claim 1, or a salt or solvate or stereoisomer thereof.

8. The method of claim 7, wherein the cancer is gastric cancer, pancreatic cancer, colorectal cancer, lung cancer, esophageal cancer, gallbladder cancer, head and neck cancer, liver cancer, endometrial carcinoma, salivary gland carcinoma, lymphoma, breast cancer, cervical cancer or ovarian cancer.

9. A kit comprising a compound of claim 1, or a salt or solvate or stereoisomer thereof.

10. The kit of claim 9, further comprising instructions for use in the treatment of cancer.

11. A compound of the formula (IV):
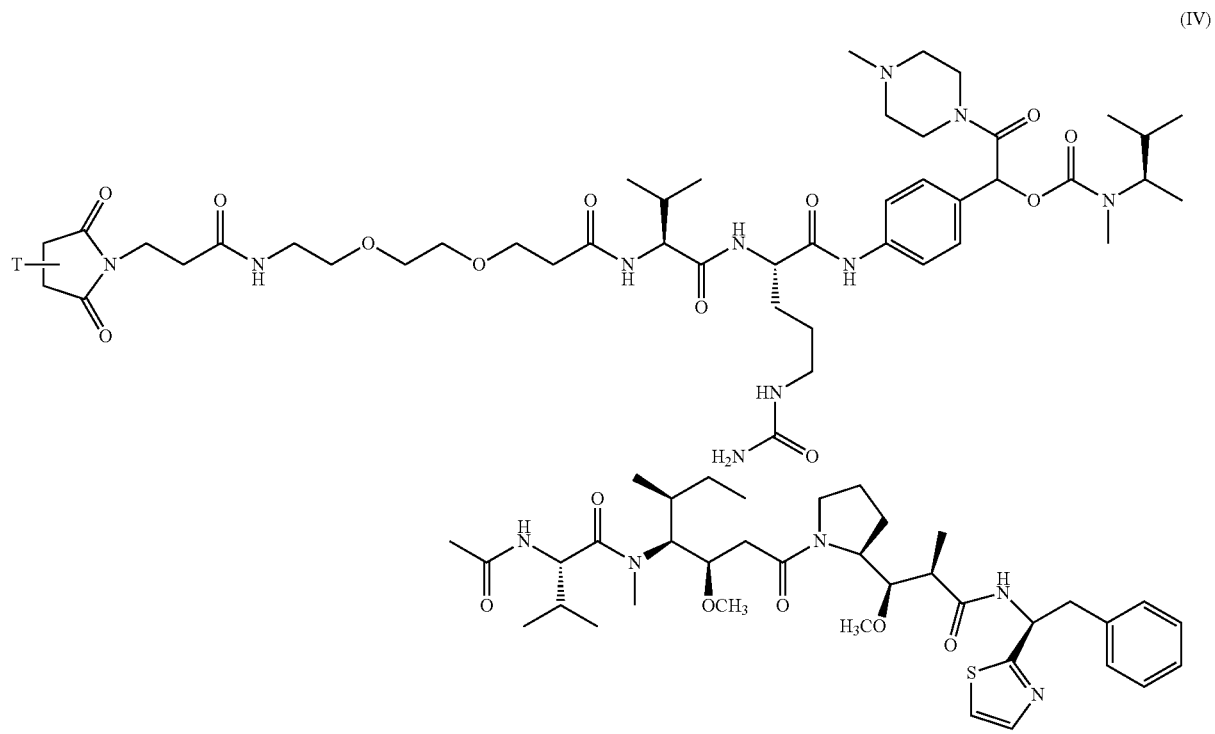
or a salt or solvate or stereoisomer thereof; wherein T is an antibody comprising a heavy chain amino acid sequence of SEQ ID NO:1 and a light chain amino acid sequence of SEQ ID NO:2.
12. The compound of claim 1, or a salt or solvate or stereoisomer thereof, wherein the compound is of the formula (IV):
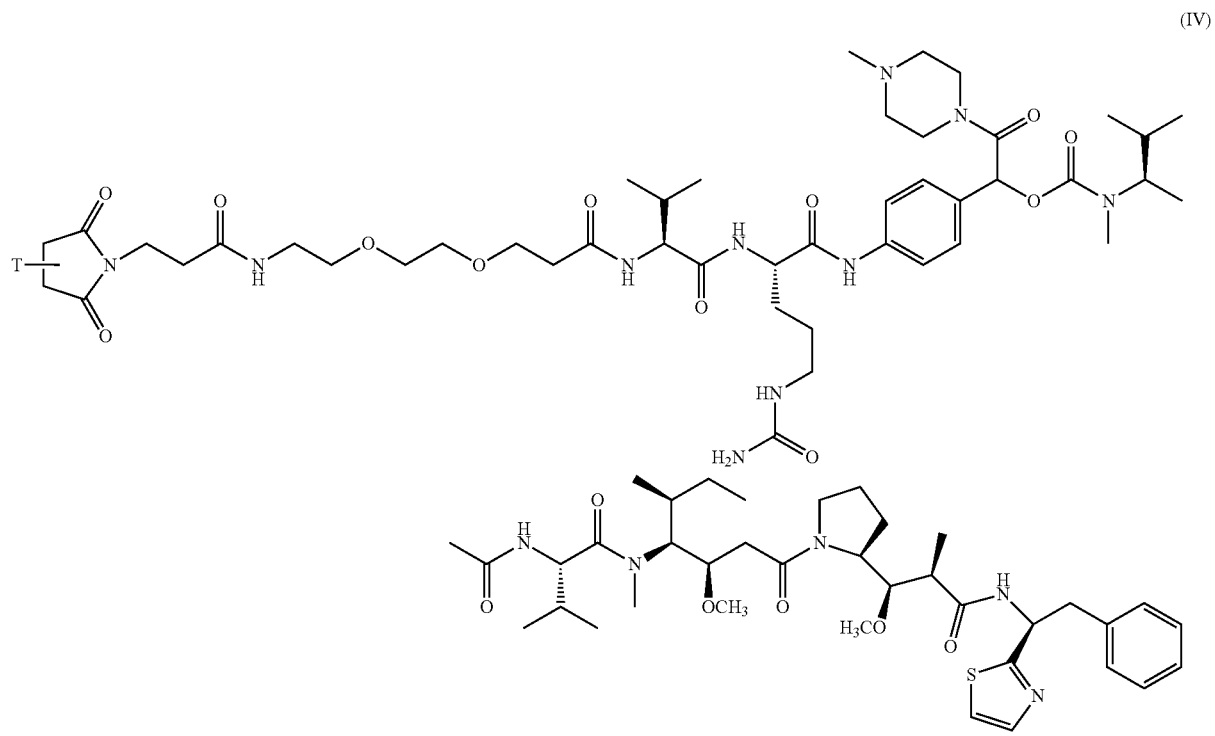

wherein T is an antibody comprising a heavy chain amino acid sequence of SEQ ID NO:3 and a light chain amino acid sequence of SEQ ID NO:4.

13. The compound of claim 1, or a salt or solvate or stereoisomer thereof, wherein the compound is of the formula (III):

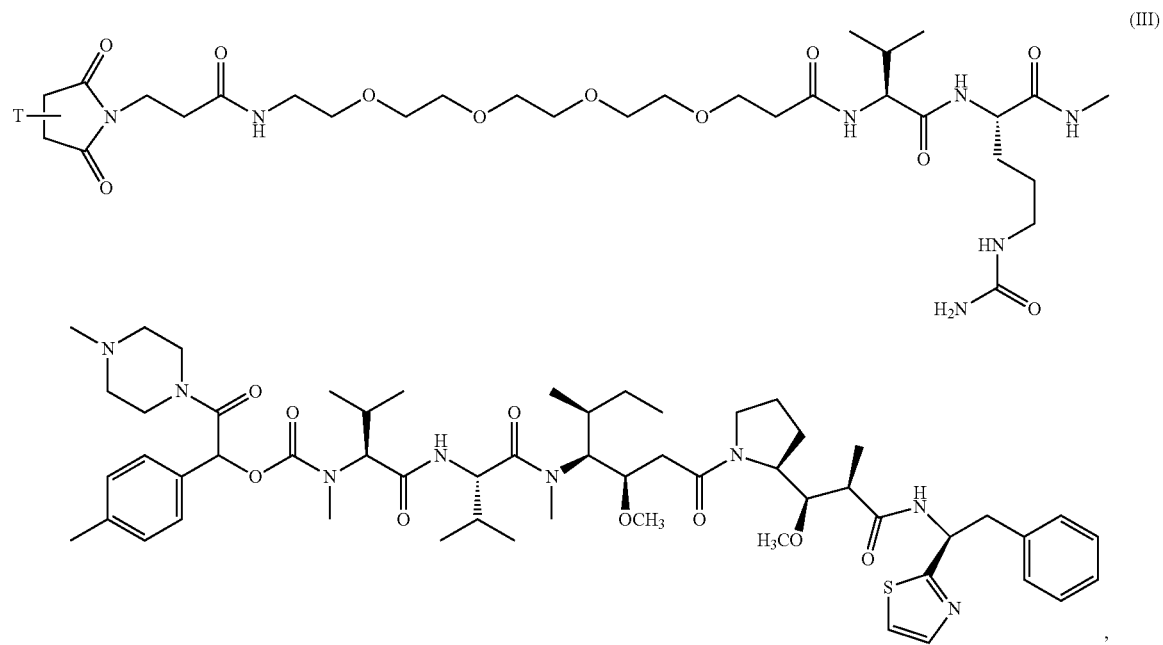

wherein T is an antibody comprising a heavy chain amino acid sequence of SEQ ID NO:1 and a light chain amino acid sequence of SEQ ID NO:2.

14. The compound of claim 1, or a salt or solvate or stereoisomer thereof, wherein the compound is of the formula (III):

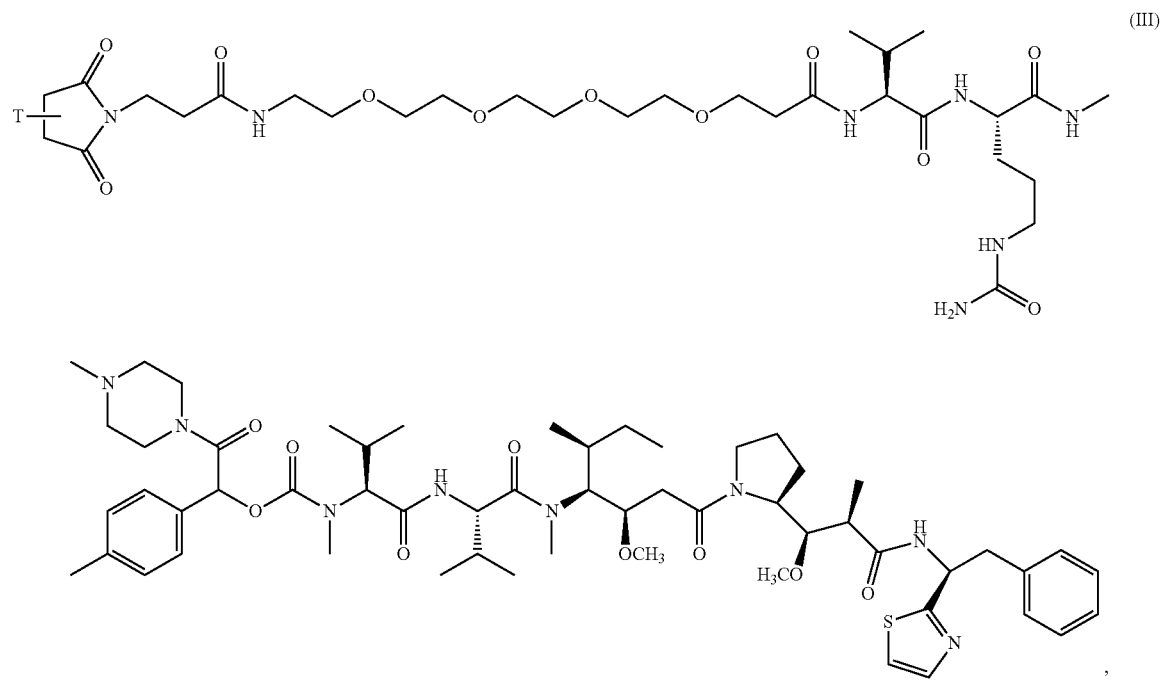

wherein T is an antibody comprising a heavy chain amino acid sequence of SEQ ID NO:3 and a light chain amino acid sequence of SEQ ID NO:4.

15. The compound of claim 1, or a salt or solvate or stereoisomer thereof, wherein the compound is of the formula (V):

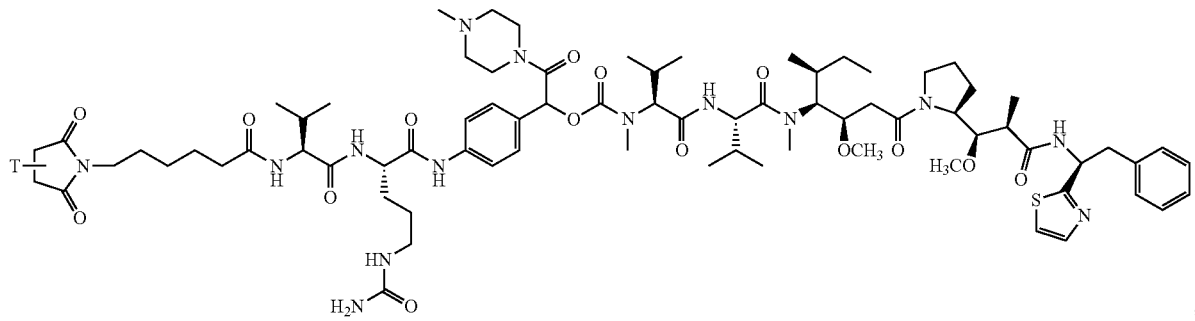

wherein T is an antibody comprising a heavy chain amino acid sequence of SEQ ID NO:1 and a light chain amino acid sequence of SEQ ID NO:2.

16. The compound of claim 1, or a salt or solvate or stereoisomer thereof, wherein the compound is of the formula (V):

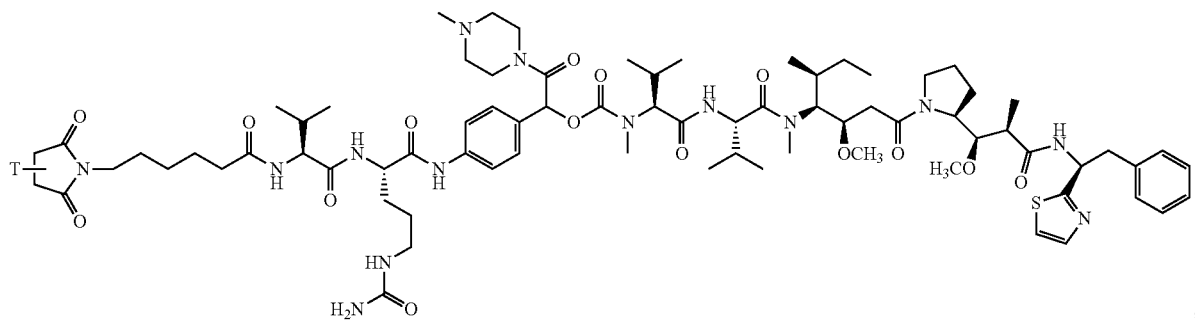

wherein T is an antibody comprising a heavy chain amino acid sequence of SEQ ID NO:3 and a light chain amino acid sequence of SEQ ID NO:4.

17. A pharmaceutical composition comprising the compound of claim 11, or a salt or solvate or stereoisomer thereof; and a pharmaceutically acceptable carrier.

18. A method of killing a cell, comprising administering to the cell an amount of the compound of claim 11, or a salt or solvate or stereoisomer thereof, sufficient to kill the cell.

19. A method of treating cancer in an individual in need thereof comprising administering to the individual an effective amount of the compound of claim 11, or a salt or solvate or stereoisomer thereof.

20. A kit comprising the compound of claim 11, or a salt or solvate or stereoisomer thereof.

* * * * *